(12) United States Patent
Uzawa

(10) Patent No.: US 11,395,578 B2
(45) Date of Patent: Jul. 26, 2022

(54) OPTICAL SYSTEM FOR RIGID ENDOSCOPE AND RIGID ENDOSCOPE

(71) Applicant: OLYMPUS CORPORATION, Hachioji (JP)

(72) Inventor: Tsutomu Uzawa, Hidaka (JP)

(73) Assignee: OLYMPUS CORPORATION, Tokyo (JP)

(*) Notice: Subject to any disclaimer, the term of this patent is extended or adjusted under 35 U.S.C. 154(b) by 163 days.

(21) Appl. No.: 16/670,973

(22) Filed: Oct. 31, 2019

(65) Prior Publication Data
US 2020/0069159 A1  Mar. 5, 2020

Related U.S. Application Data

(63) Continuation of application No. PCT/JP2017/021536, filed on Jun. 9, 2017.

(51) Int. Cl.
G02B 9/58 (2006.01)
A61B 1/00 (2006.01)
G02B 13/18 (2006.01)
G02B 23/24 (2006.01)

(52) U.S. Cl.
CPC ............ *A61B 1/00195* (2013.01); *G02B 9/58* (2013.01); *G02B 13/18* (2013.01); *G02B 23/2407* (2013.01)

(58) Field of Classification Search
USPC ........................................................ 359/782
See application file for complete search history.

(56) References Cited

U.S. PATENT DOCUMENTS 6,043,941 A * 3/2000 Yamada ................... G02B 9/58
359/753
6,081,384 A   6/2000 Mori
(Continued)

FOREIGN PATENT DOCUMENTS

JP   H10115788 A   5/1998
JP   H10133102 A   5/1998
(Continued)

OTHER PUBLICATIONS

International Search Report (ISR) dated Aug. 29, 2017 (and English translation thereof), issued in International Application No. PCT/JP2017/021536.
(Continued)

*Primary Examiner* — Darryl J Collins
(74) *Attorney, Agent, or Firm* — Holtz, Holtz & Volek PC

(57) ABSTRACT

An optical system for rigid endoscope includes an objective optical system, an eyepiece optical system, and a relay optical system which is disposed between the objective optical system and the eyepiece optical system. The objective optical system includes in order from an object side, a first lens having a negative refractive power, a second lens having a positive refractive power, a third lens having a positive refractive power, and a fourth lens having a negative refractive power. The following conditional expressions (1) and (2) are satisfied:

$$-3 < (RL1i + RL1o)/(RL1i - RL1o) < -1.3 \quad (1)$$

$$30 < vdL1 \quad (2)$$

where,
RL1o denotes a radius of curvature of an object-side surface of the first lens,
(Continued)

RL1i denotes a radius of curvature of an image-side surface of the first lens, and vdL1 denotes Abbe number for the first lens.

8 Claims, 47 Drawing Sheets

(56) References Cited

U.S. PATENT DOCUMENTS

| | | | |
|---|---|---|---|
| 7,548,385 B2* | 6/2009 | Hirano | G02B 9/58 |
| | | | 359/771 |
| 8,384,996 B2 | 2/2013 | Ando et al. | |
| 8,780,445 B2 | 7/2014 | Inoue | |
| 8,982,479 B2* | 3/2015 | Hsieh | G02B 13/04 |
| | | | 359/715 |
| 9,304,302 B2 | 4/2016 | Komiyama | |
| 9,678,327 B2 | 6/2017 | Harada | |
| 2004/0240081 A1* | 12/2004 | Saito | G02B 23/243 |
| | | | 359/754 |
| 2009/0097137 A1* | 4/2009 | Cheng | G02B 13/04 |
| | | | 359/782 |
| 2011/0096400 A1 | 4/2011 | Ando et al. | |
| 2013/0194667 A1 | 8/2013 | Inoue | |
| 2014/0293456 A1 | 10/2014 | Komiyama | |
| 2016/0004064 A1 | 1/2016 | Harada | |

FOREIGN PATENT DOCUMENTS

| | | |
|---|---|---|
| JP | 5307952 B2 | 7/2013 |
| JP | 2014209190 A | 11/2014 |
| JP | 2016014754 A | 1/2016 |
| WO | 2009153953 A1 | 12/2009 |

OTHER PUBLICATIONS

Written Opinion of the International Searching Authority dated Aug. 29, 2017 issued in International Application No. PCT/JP2017/021536.

International Preliminary Report on Patentability (IPRP) (and English translation thereof) dated Dec. 19, 2019, issued in counterpart International Application No. PCT/JP2017/021536.

* cited by examiner

FIG. 1A

Coefficient chart

|  | Aspherical | Spherical |
|---|---|---|
| r | 1.2172 | 1.2172 |
| K | -0.7490 | 0 |
| AC4 | -2.4988.E-01 | 0.0000.E+00 |
| AC6 | 7.7207.E-02 | 0.0000.E+00 |
| AC8 | 0.0000.E+00 | 0.0000.E+00 |
| AC10 | 0.0000.E+00 | 0.0000.E+00 |

FIG. 1B

Surface Shape

| Y | Aspherical | Spherical | difference |
|---|---|---|---|
| 0.0 | 0.00000 | 0.00000 | 0.00000 |
| 0.1 | 0.00408 | 0.00411 | -0.00003 |
| 0.2 | 0.01606 | 0.01654 | -0.00048 |
| 0.3 | 0.03514 | 0.03755 | -0.00240 |
| 0.4 | 0.06010 | 0.06760 | -0.00751 |
| 0.5 | 0.08939 | 0.10744 | -0.01804 |
| 0.6 | 0.12142 | 0.15816 | -0.03673 |
| 0.7 | 0.15473 | 0.22142 | -0.06669 |
| 0.8 | 0.17152 | 0.25852 | -0.08699 |
| 0.9 | 0.22209 | 0.39770 | -0.17561 |
| 1.0 | 0.25715 | 0.52324 | -0.26609 |
| 1.1 | 0.29644 | 0.69607 | -0.39963 |
| 1.2 | 0.34520 | 1.01330 | -0.66810 |

Aspherical Lens Shape (Left surface)

Aspherical - Spherical

FIG. 3A

Coefficient chart

|      | Aspherical   | Spherical  |
|------|--------------|------------|
| r    | 0.3121       | 0.3121     |
| K    | -0.8100      | 0          |
| AC4  | -1.4912.E-01 | 0.0000.E+00 |
| AC6  | -1.7424.E+00 | 0.0000.E+00 |
| AC8  | 0.0000.E+00  | 0.0000.E+00 |
| AC10 | 0.0000.E+00  | 0.0000.E+00 |

FIG. 3B

Surface Shape

| Y    | Aspherical | Spherical | difference |
|------|-----------|-----------|------------|
| 0.00 | 0.00000   | 0.00000   | 0.00000    |
| 0.05 | 0.00401   | 0.00403   | -0.00002   |
| 0.10 | 0.01608   | 0.01645   | -0.00037   |
| 0.15 | 0.03636   | 0.03841   | -0.00205   |
| 0.20 | 0.06503   | 0.07250   | -0.00747   |
| 0.25 | 0.10237   | 0.12527   | -0.02289   |
| 0.30 | 0.14866   | 0.22604   | -0.07738   |
| 0.35 | 0.20419   | -         | -          |
| 0.40 | 0.26928   | -         | -          |
| 0.45 | 0.34437   | -         | -          |
| 0.50 | 0.43031   | -         | -          |

Aspherical Lens Shape (Right surface)

Aspherical - Spherical

FIG. 5A

Coefficient chart

|      | Aspherical   | Spherical   |
|------|--------------|-------------|
| r    | -2.1882      | -2.1882     |
| K    | -0.3490      | 0           |
| AC4  | 5.4623.E-03  | 0.0000.E+00 |
| AC6  | 0.0000.E+00  | 0.0000.E+00 |
| AC8  | 0.0000.E+00  | 0.0000.E+00 |
| AC10 | 0.0000.E+00  | 0.0000.E+00 |

FIG. 5B

Surface Shape

| Y   | Aspherical | Spherical | difference |
|-----|------------|-----------|------------|
| 0.0 | 0.00000    | 0.00000   | 0.00000    |
| 0.1 | -0.00229   | -0.00229  | 0.00000    |
| 0.2 | -0.00914   | -0.00916  | 0.00002    |
| 0.3 | -0.02058   | -0.02066  | 0.00008    |
| 0.4 | -0.03662   | -0.03687  | 0.00025    |
| 0.5 | -0.05728   | -0.05789  | 0.00061    |
| 0.6 | -0.08258   | -0.08387  | 0.00128    |
| 0.7 | -0.11258   | -0.11499  | 0.00240    |
| 0.8 | -0.14733   | -0.15148  | 0.00415    |
| 0.9 | -0.18690   | -0.19365  | 0.00676    |
| 1.0 | -0.23138   | -0.24187  | 0.01048    |
| 1.1 | -0.28090   | -0.29658  | 0.01568    |
| 1.2 | -0.33562   | -0.35839  | 0.02277    |
| 1.3 | -0.39573   | -0.42802  | 0.03230    |
| 1.4 | -0.46150   | -0.50648  | 0.04497    |
| 1.5 | -0.53327   | -0.59502  | 0.06175    |
| 1.6 | -0.61148   | -0.69548  | 0.08400    |

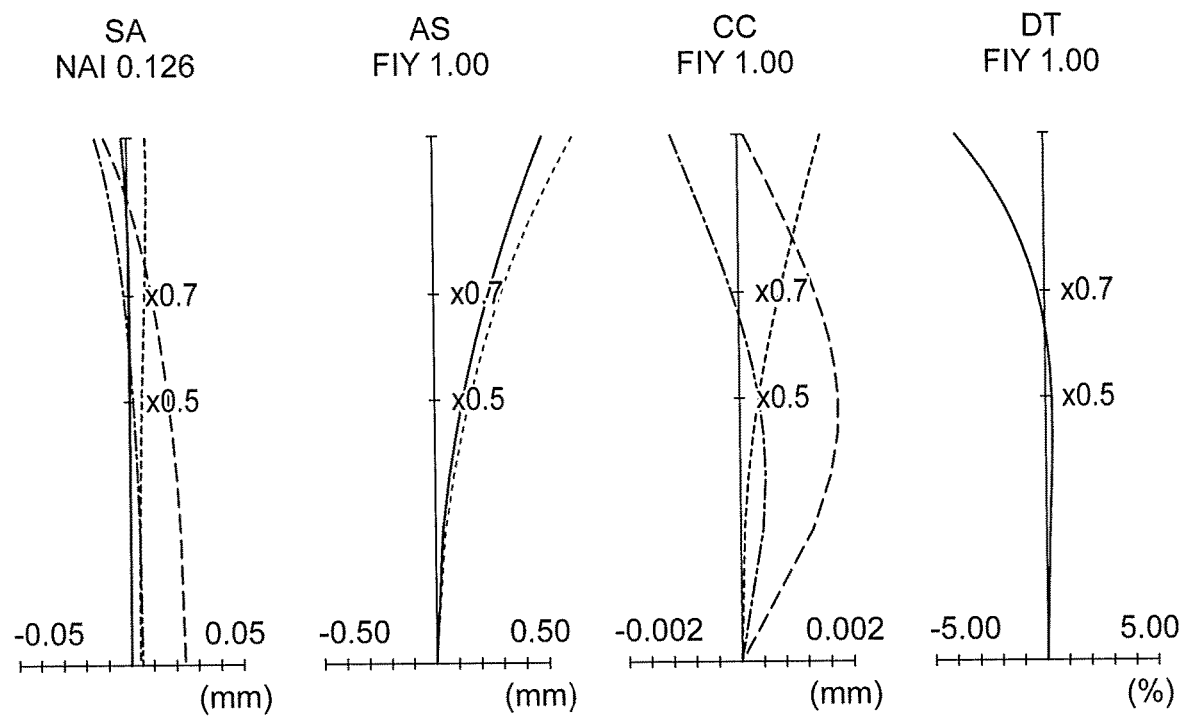

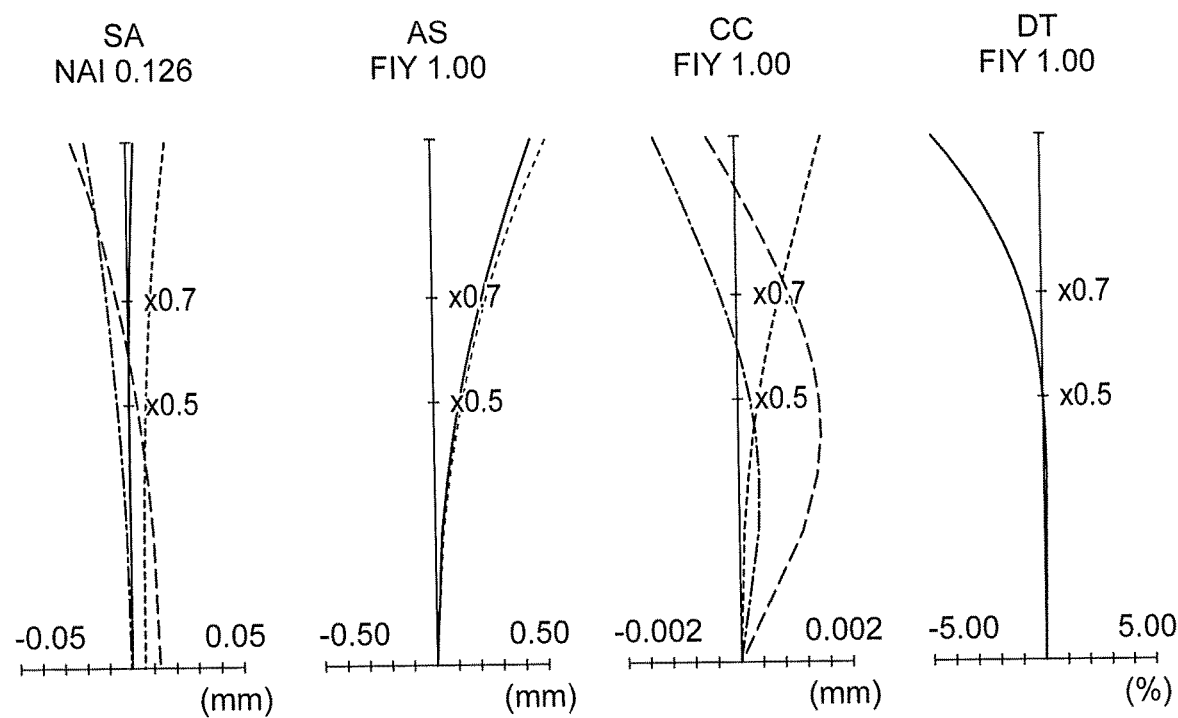

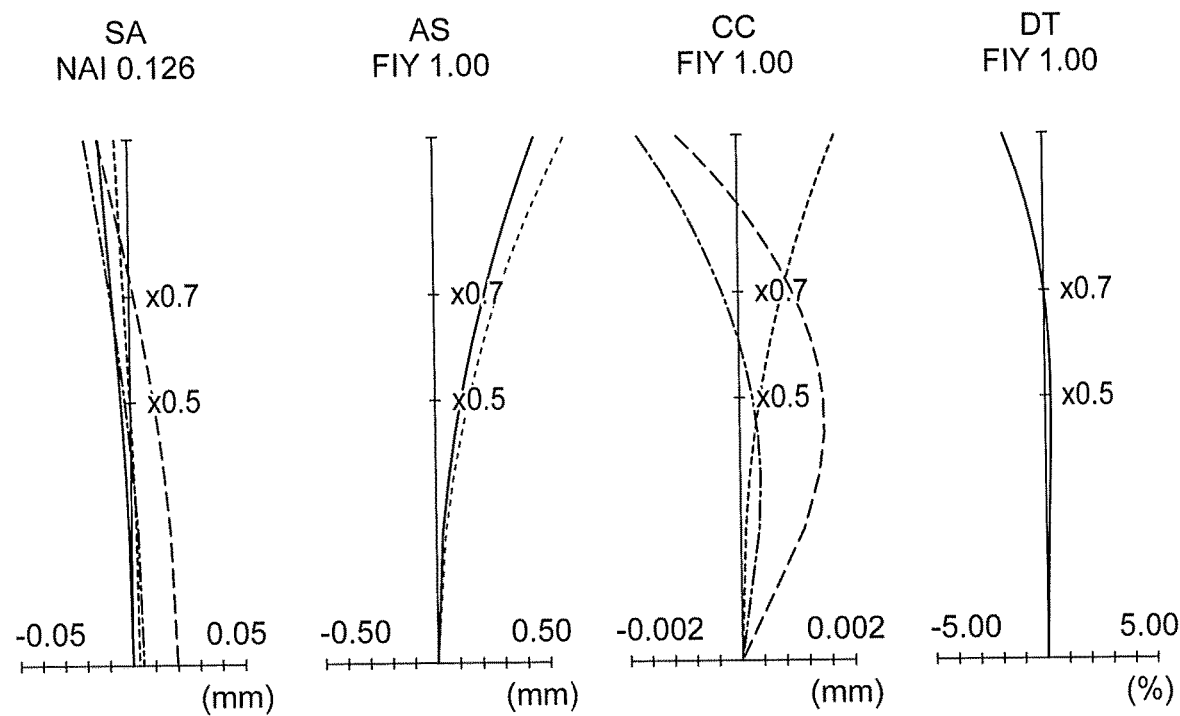

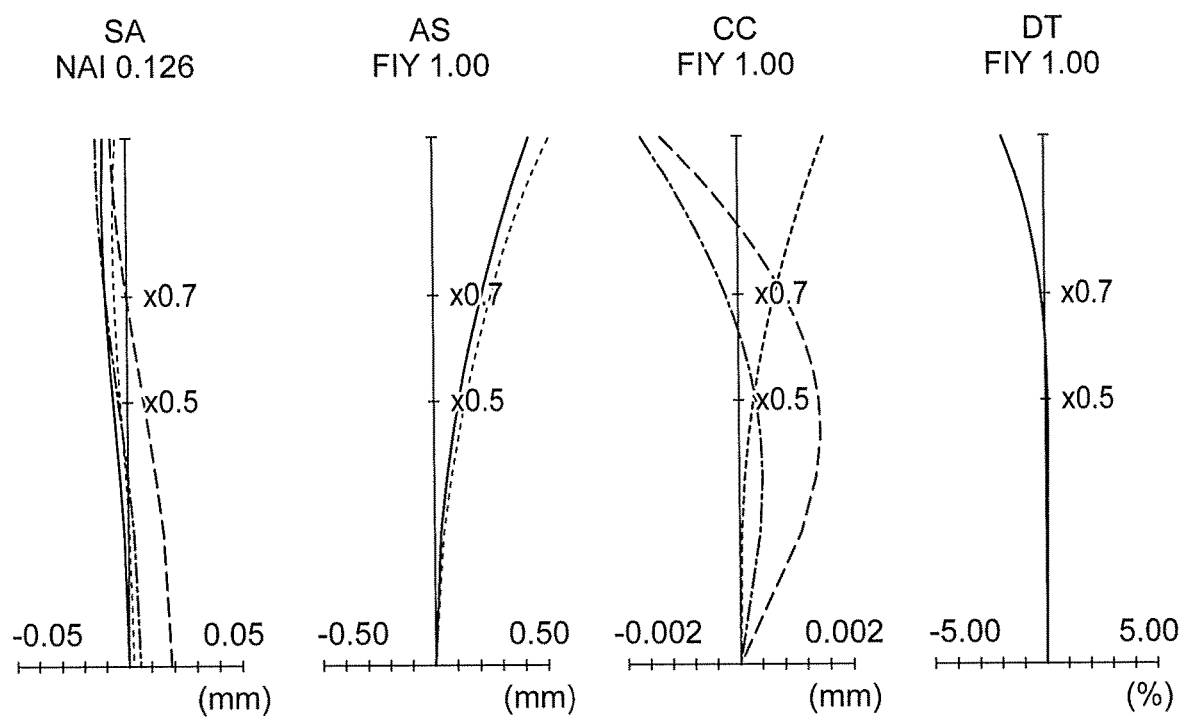

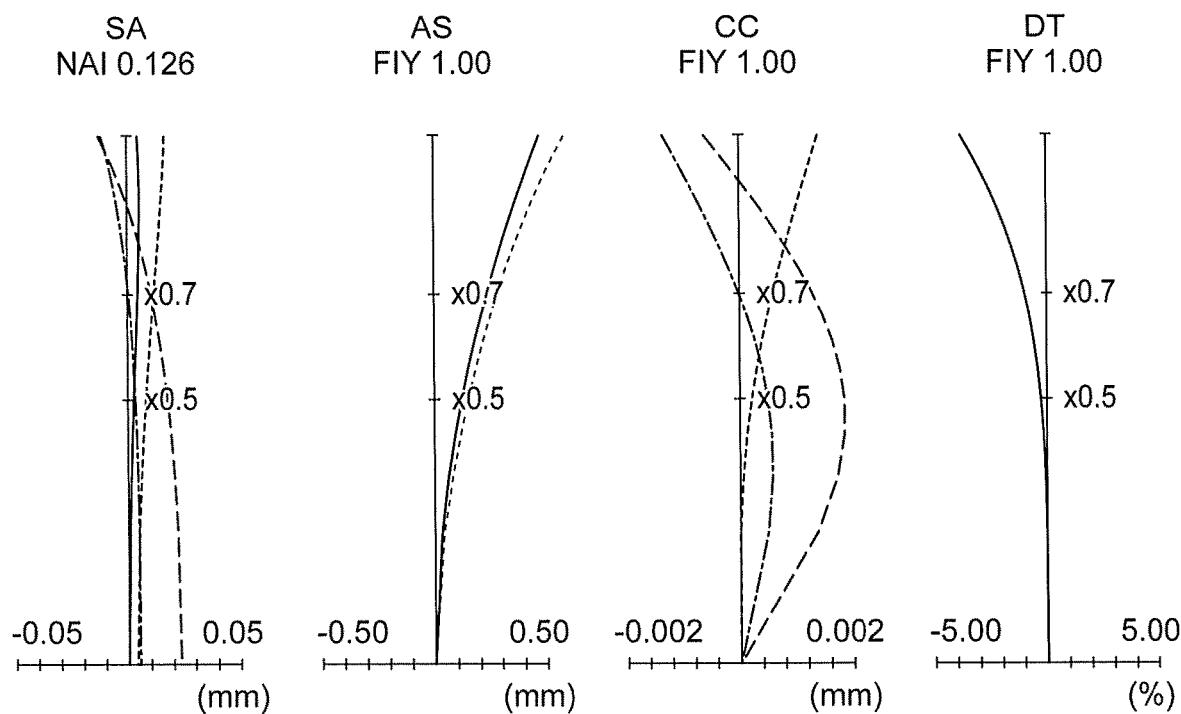

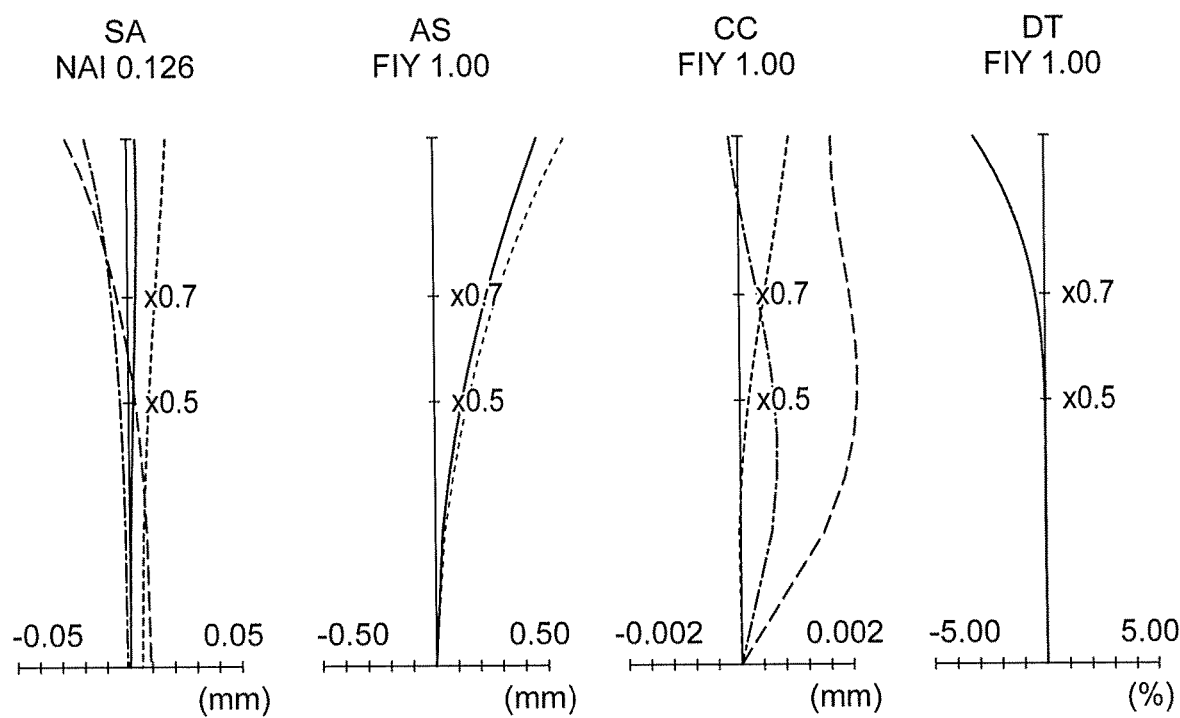

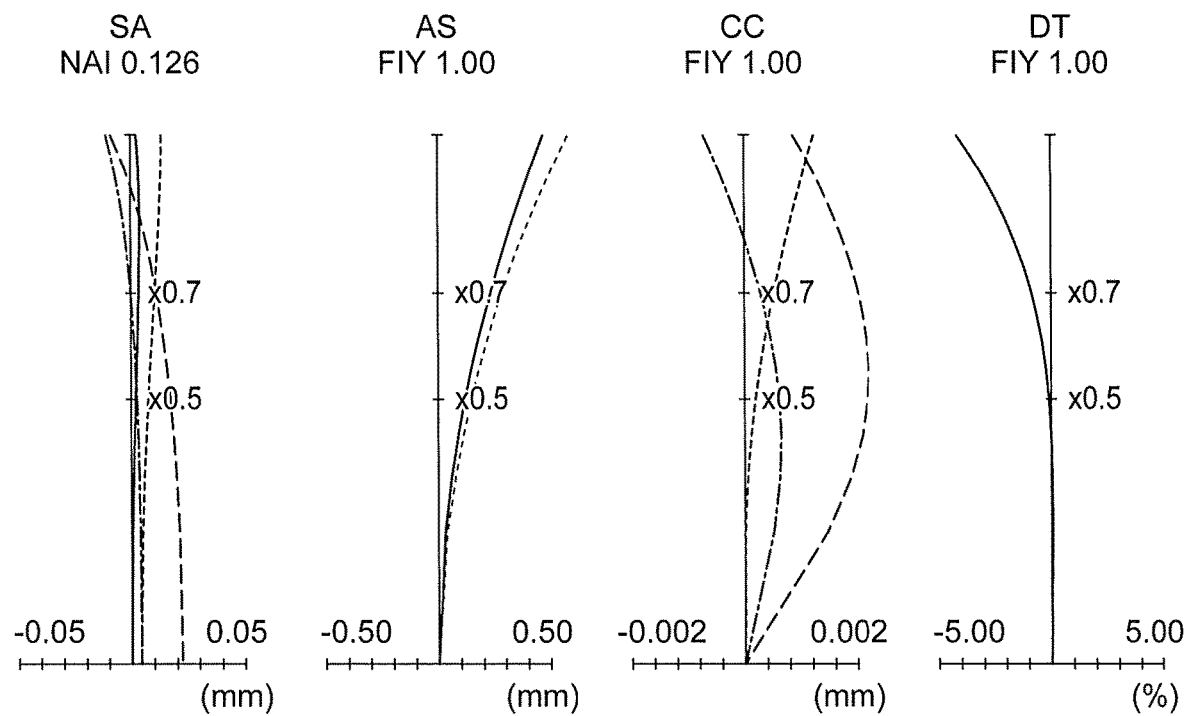

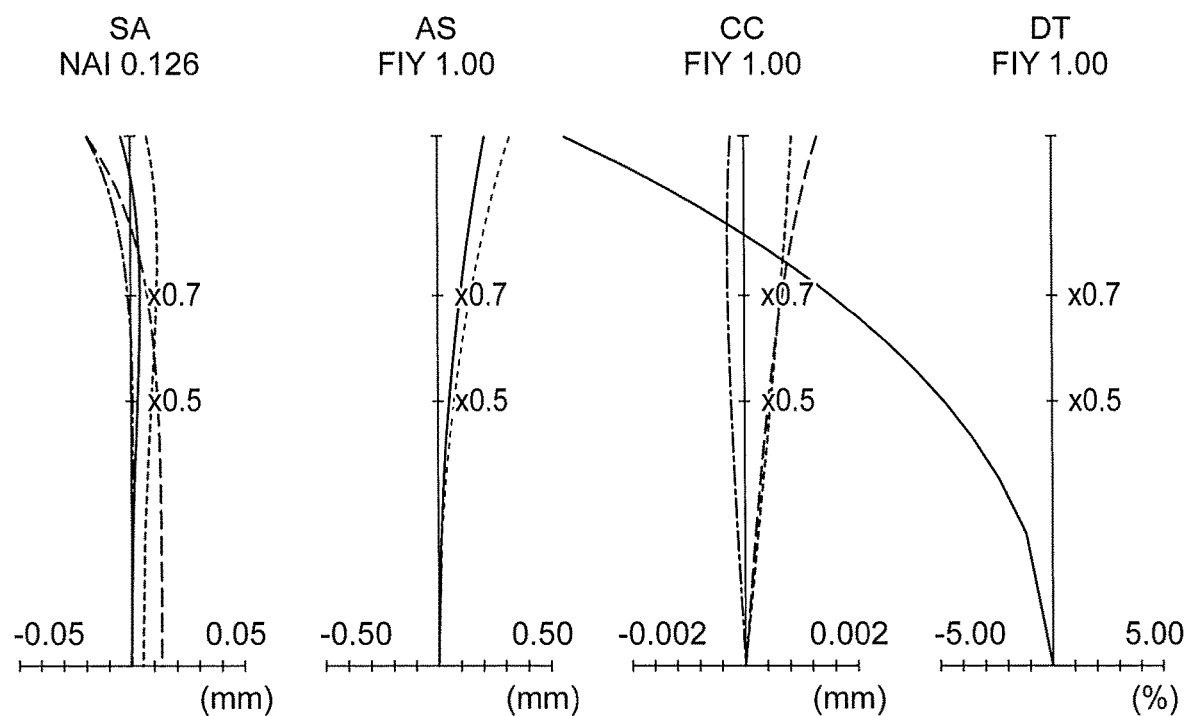

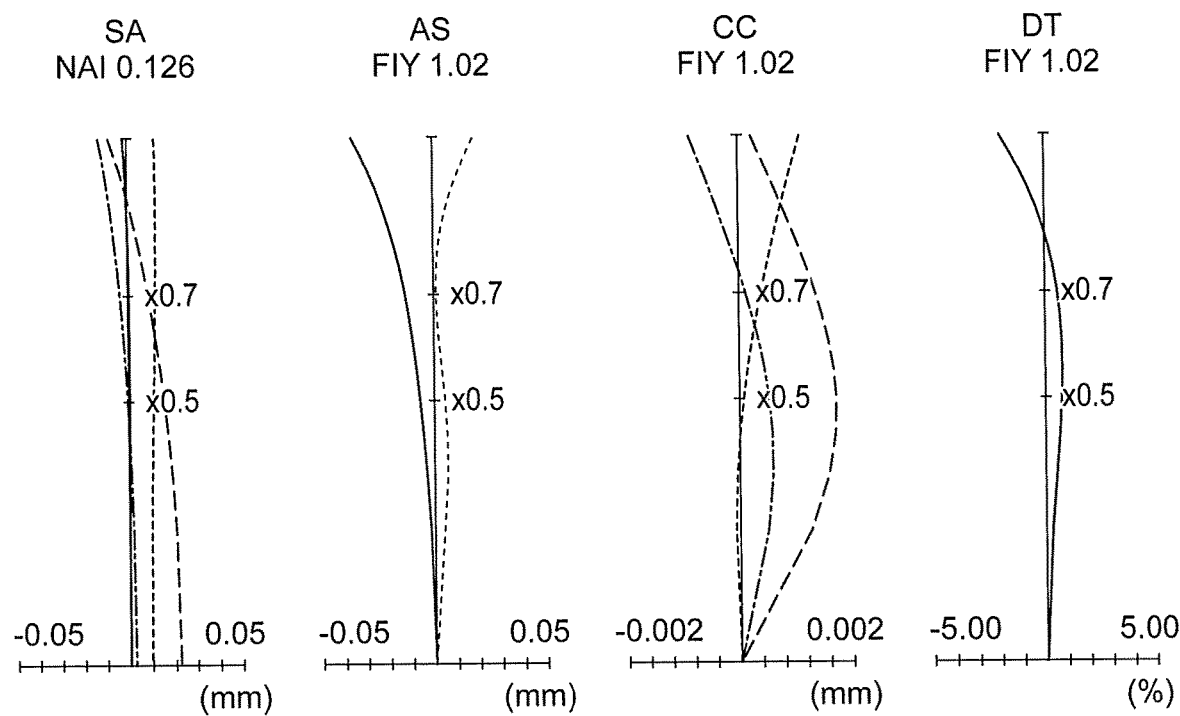

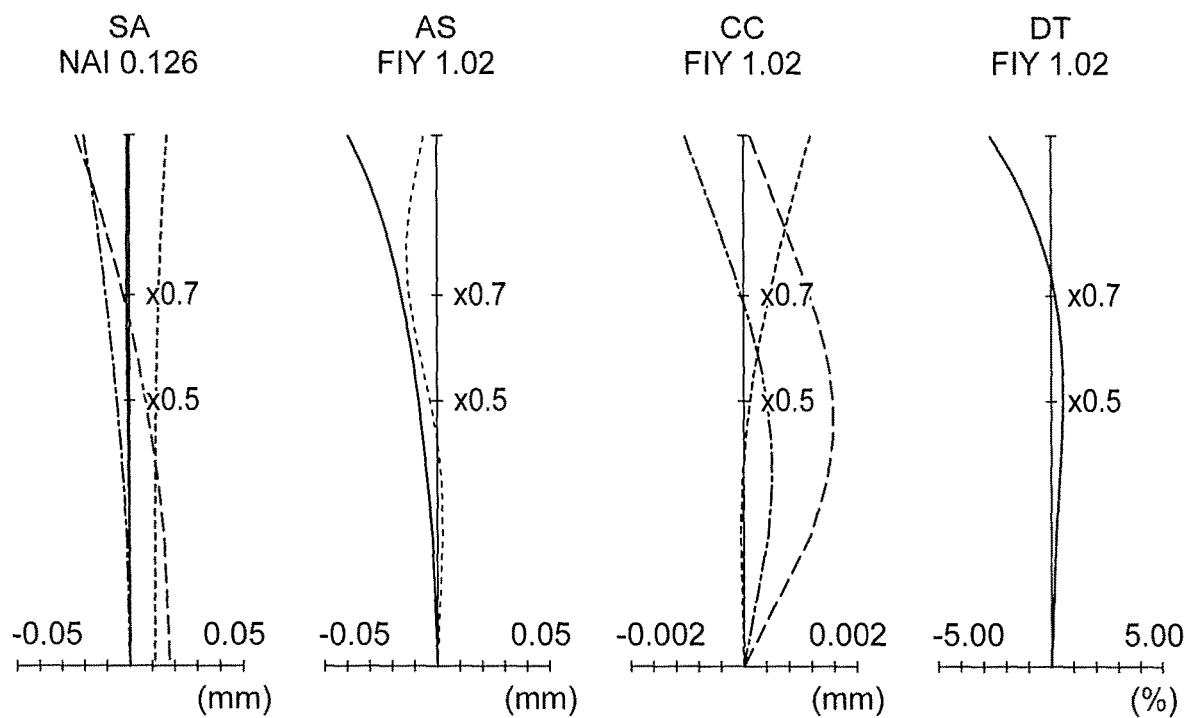

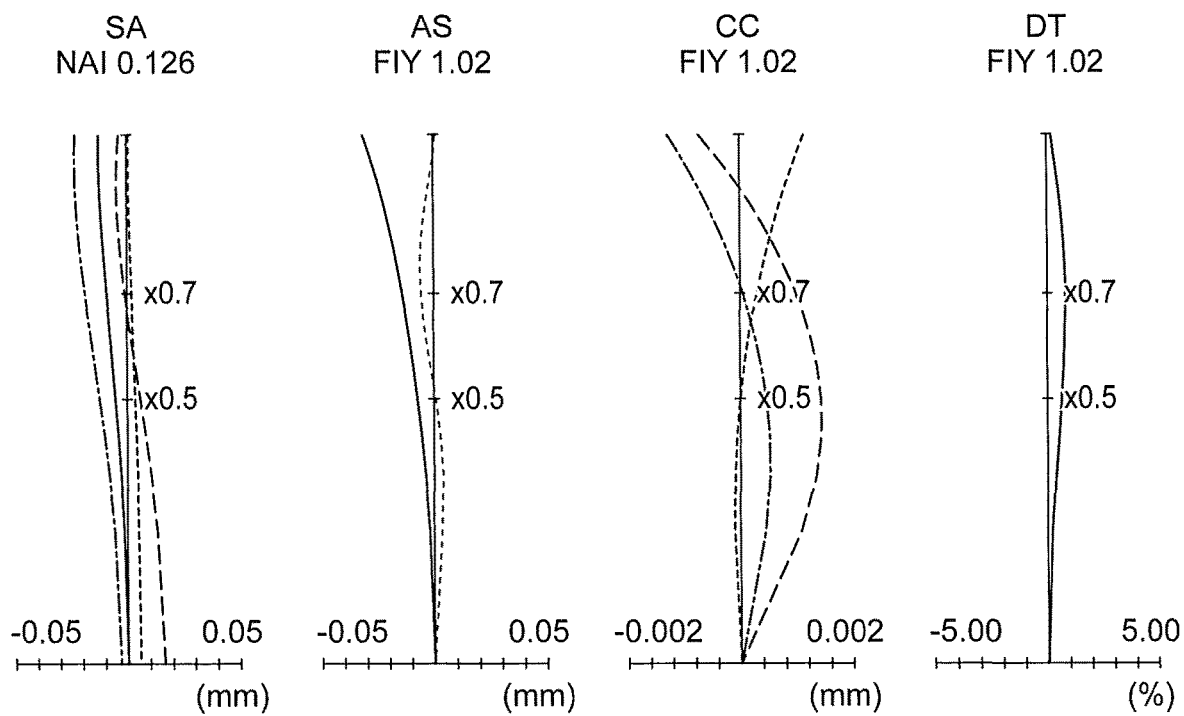

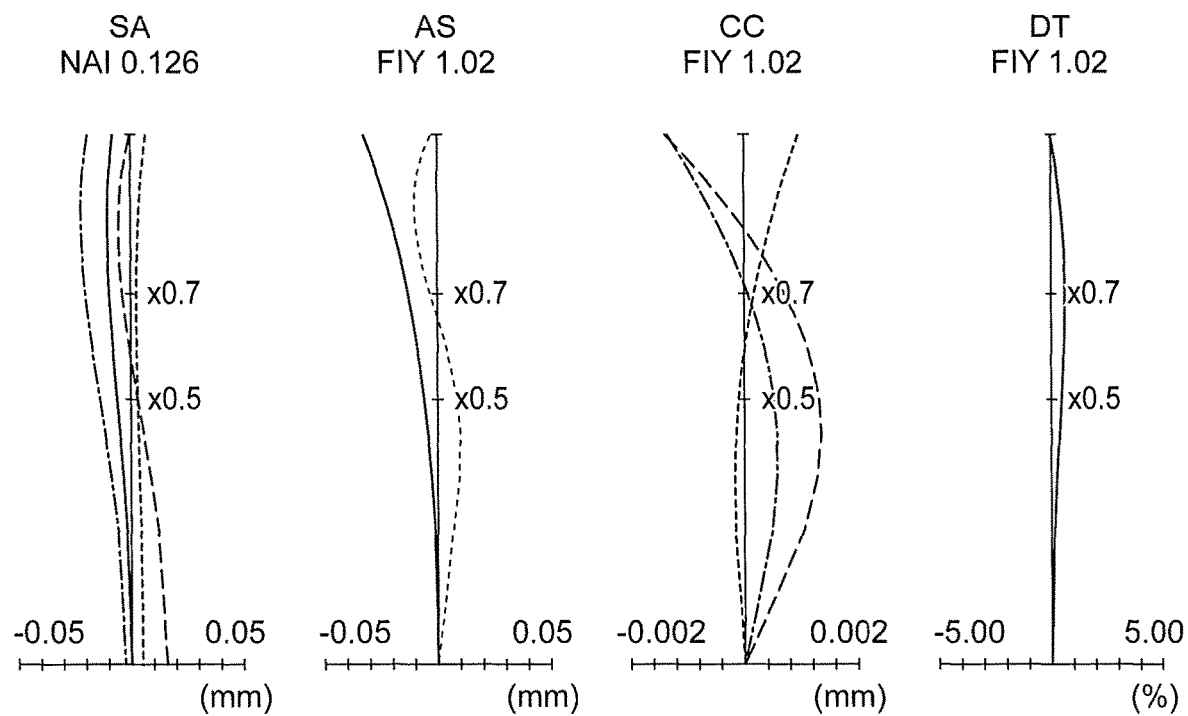

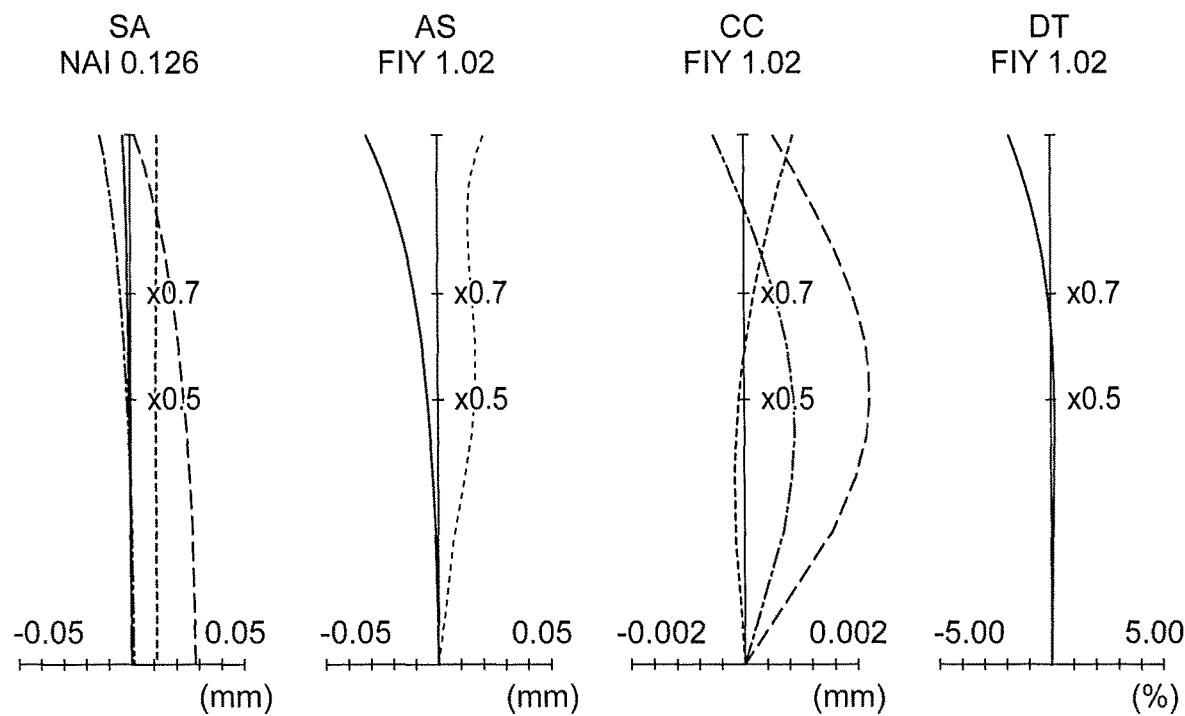

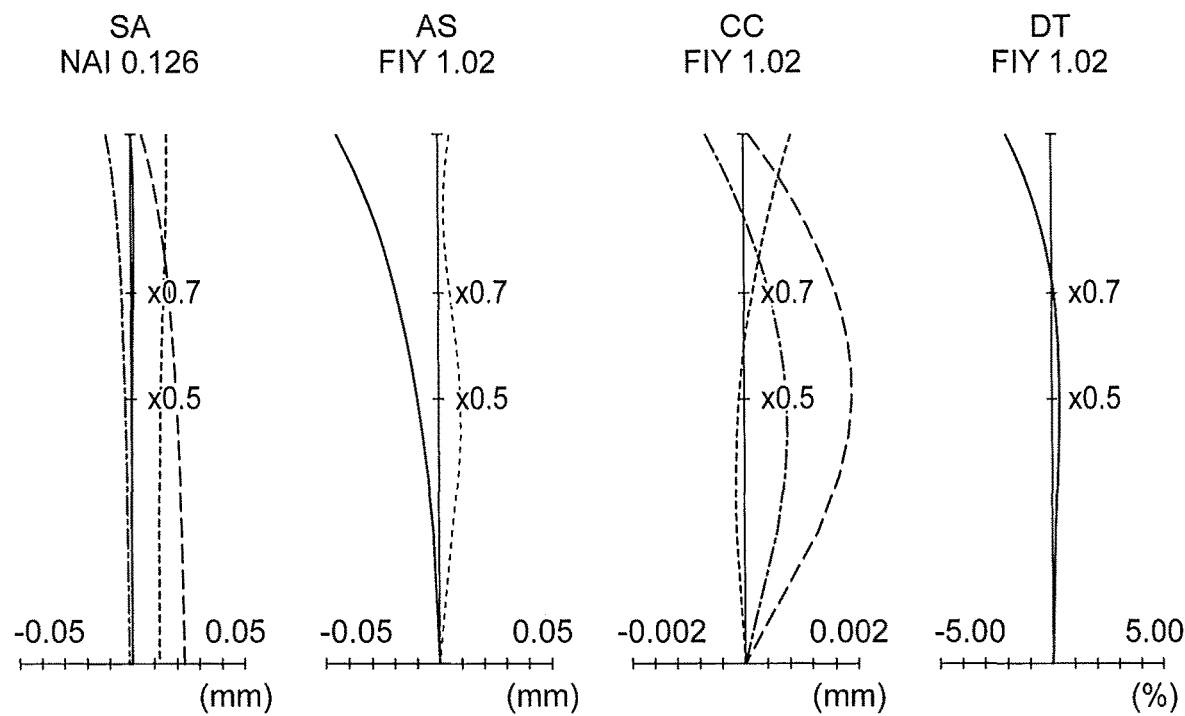

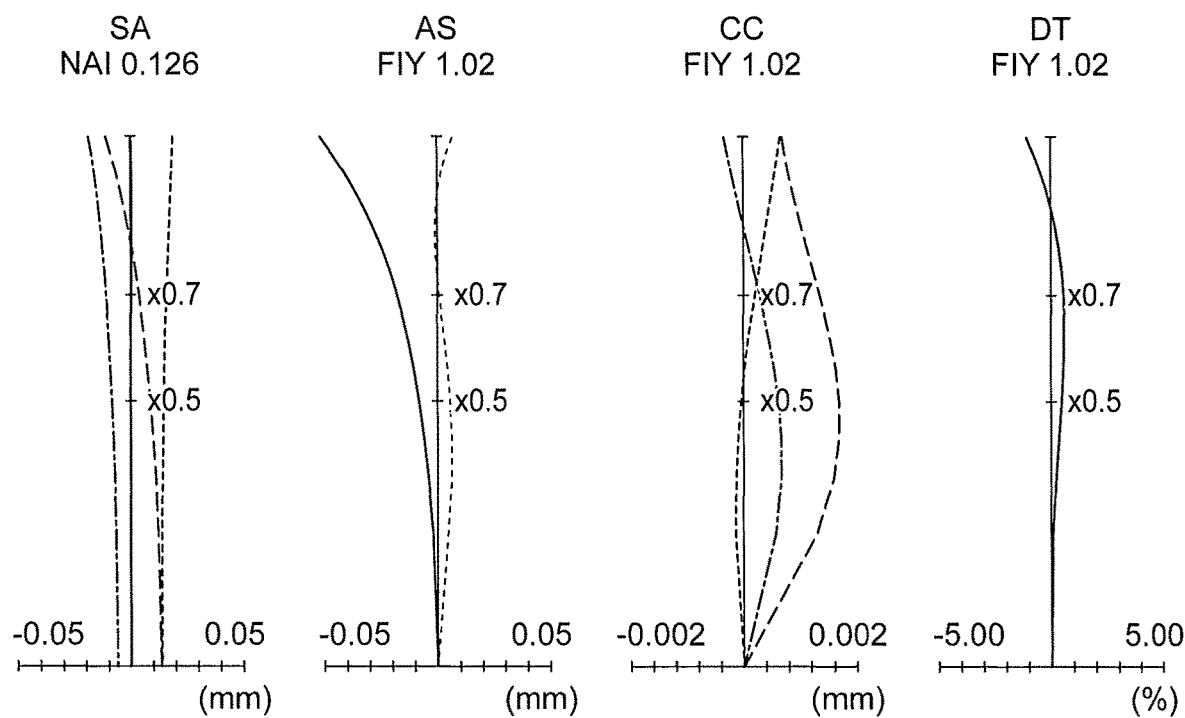

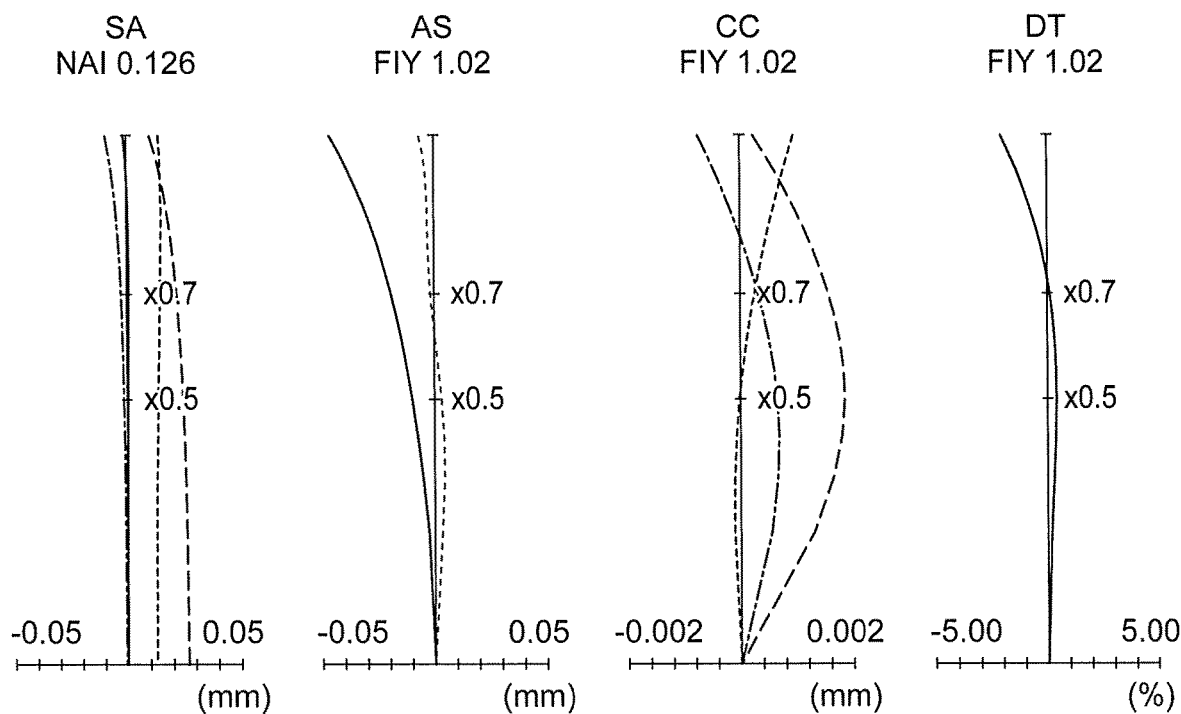

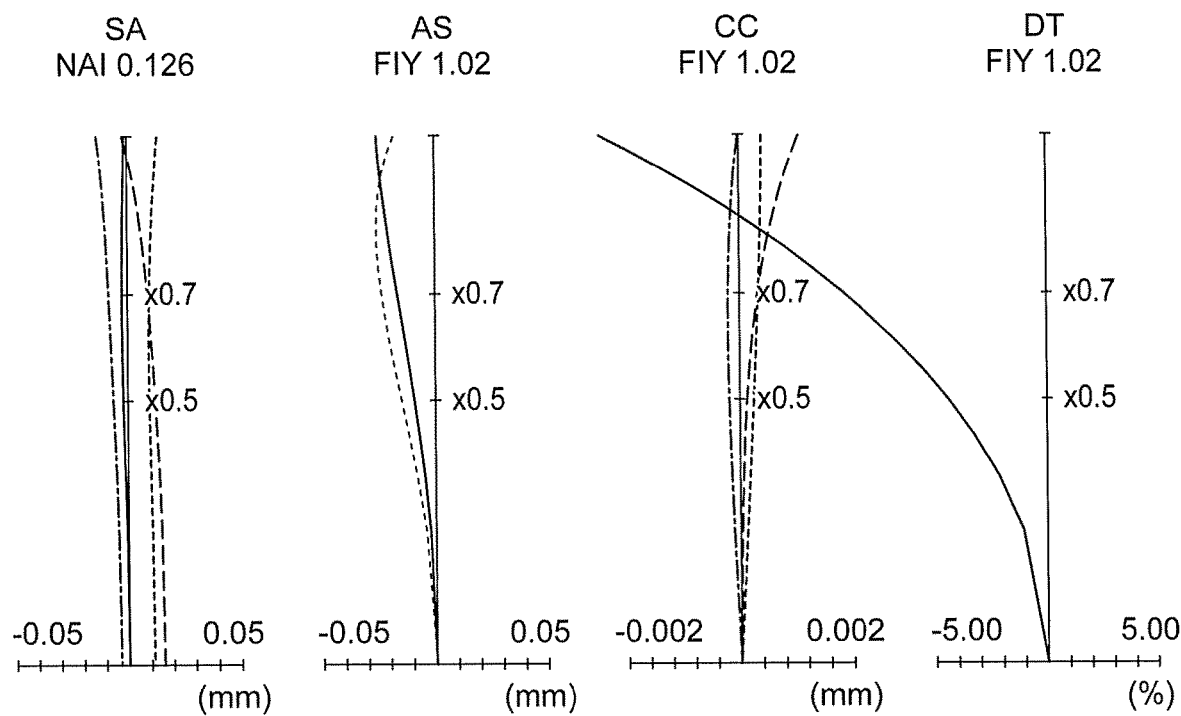

OPTICAL SYSTEM FOR RIGID ENDOSCOPE AND RIGID ENDOSCOPE

CROSS-REFERENCE TO RELATED APPLICATION

The present application is a continuation application of International Application No. PCT/JP2017/021536 filed on Jun. 9, 2017, the entire contents of which are incorporated herein by reference.

BACKGROUND OF THE INVENTION

Field of the Invention

The present invention relates to an optical system for rigid endoscope and a rigid endoscope.

Description of the Related Art

In recent years, in a diagnosis using a rigid endoscope, an improvement in diagnostic accuracy has been sought. In order to fulfill this requirement, an ability to observe an object (a subject) with a high resolution and an ability to acquire an image of an object with a high quality have been sought.

More specifically, acquiring an image by an endoscope system suitable for an HDTV (High-Definition Television) and acquiring an image by an endoscope system suitable for 4K have been sought.

An endoscope system includes a rigid endoscope, a TV camera head, a camera control unit, and a display. Requirements for an optical system for making a high-definition image quality are having a high numerical aperture, and a chromatic aberration, particularly, a secondary spectrum, being corrected favorably. Furthermore, as a requirement for an optical system for achieving an easily viewable field of view is that a distortion is being corrected favorably.

An observation of an object or an acquisition of an image of an object are carried out via an optical system for rigid endoscope disposed in a rigid endoscope. In the acquisition of an image of an object, a camera head is connected to the optical system for rigid endoscope. In the camera head, a device such as a CCD (Charge Coupled Device) or a C-MOS (Complementary Metal Oxide Semiconductor) is used as an imager.

The optical system for rigid endoscope includes an objective lens, an eyepiece, and a plurality of relay optical systems. The plurality of relay optical systems is disposed between the objective lens and the eyepiece.

As an optical system for rigid endoscope, an optical system for rigid endoscope described in Japanese Patent Application Laid-open Publication No. Hei 10-115788 and an optical system for rigid endoscope described in Japanese Patent No. 5307952 are available.

In Japanese Patent Application Laid-open Publication No. Hei 10-115788, an optical system for rigid endoscope having an image quality that may be suitable for an HDTV camera is disclosed. In this optical system for rigid endoscope, 9 to 11 lenses are used in an objective optical system.

In Japanese Patent No. 5307952, an optical system for rigid endoscope in which the secondary spectrum is corrected favorably is disclosed. In this optical system for rigid endoscope, a diffractive optical element is used in a relay optical system.

SUMMARY OF THE INVENTION

An optical system for rigid endoscope according to at least some embodiments of the present invention includes:

an objective optical system,
an eyepiece optical system, and
a relay optical system which is disposed between the objective optical system and the eyepiece optical system,
wherein
the objective optical system includes in order from an object side,
a first lens having a negative refractive power,
a second lens having a positive refractive power,
a third lens having a positive refractive power, and
a fourth lens having a negative refractive power, and
the following conditional expressions (1) and (2) are satisfied:

$$-3 < (RL1i + RL1o)/(RL1i - RL1o) < -1.3 \quad (1)$$

$$30 < vdL1 \quad (2)$$

where,
RL1o denotes a radius of curvature of an object-side surface of the first lens,
RL1i denotes a radius of curvature of an image-side surface of the first lens, and
vdL1 denotes Abbe number for the first lens.

A rigid endoscope according to at least some embodiments of the present invention includes:
the abovementioned optical system for rigid endoscope, and
an illumination optical system.

BRIEF DESCRIPTION OF THE DRAWINGS

FIG. 1A is data related to an aspherical surface of an object-side surface of a first lens;
FIG. 1B is data related to the aspherical surface of the object-side surface of the first lens;
FIG. 3A is data related to an aspherical surface of an image-side surface of the first lens;
FIG. 3B is data related to the aspherical surface of the image-side surface of the first lens;
FIG. 5A is data related to an aspherical surface of an image-side surface of a second lens;
FIG. 5B is data related to the aspherical surface of the image-side surface of the second lens.

FIG. 18A, FIG. 18B, FIG. 18C, and FIG. 18D are aberration diagrams of the objective optical system of the example 2;

FIG. 19A, FIG. 19B, FIG. 19C, and FIG. 19D are aberration diagrams of the objective optical system of the example 3;

FIG. 20A, FIG. 20B, FIG. 20C, and FIG. 20D are aberration diagrams of the objective optical system of the example 4;

FIG. 21A, FIG. 21B, FIG. 21C, and FIG. 21D are aberration diagrams of the objective optical system of the example 5;

FIG. 22A, FIG. 22B, FIG. 22C, and FIG. 22D are aberration diagrams of the objective optical system of the example 6;

FIG. 24A, FIG. 24B, FIG. 24C, and FIG. 24D are aberration diagrams of the objective optical system of the example 8;

FIG. 25A, FIG. 25B, FIG. 25C, and FIG. 25D are aberration diagrams of the objective optical system of the example 9;

FIG. 26A, FIG. 26B, FIG. 26C, and FIG. 26D are aberration diagrams of the objective optical system of the reference example;

FIG. 38A, FIG. 38B, FIG. 38C, and FIG. 38D are aberration diagrams of the optical system for rigid endoscope of the example 2;

FIG. 39A, FIG. 39B, FIG. 39C, and FIG. 39D are aberration diagrams of the optical system for rigid endoscope of the example 3;

FIG. 40A, FIG. 40B, FIG. 40C, and FIG. 40D are aberration diagrams of the optical system for rigid endoscope of the example 4;

FIG. 41A, FIG. 41B, FIG. 41C, and FIG. 41D are aberration diagrams of the optical system for rigid endoscope of the example 5;

FIG. 42A, FIG. 42B, FIG. 42C, and FIG. 42D are aberration diagrams of the optical system for rigid endoscope of the example 6;

FIG. 43A, FIG. 43B, FIG. 43C, and FIG. 43D are aberration diagrams of the optical system for rigid endoscope of the example 7;

FIG. 44A, FIG. 44B, FIG. 44C, and FIG. 44D are aberration diagrams of the optical system for rigid endoscope of the example 8;

FIG. 45A, FIG. 45B, FIG. 45C, and FIG. 45D are aberration diagrams of the optical system for rigid endoscope of the example 9;

FIG. 46A, FIG. 46B, FIG. 46C, and FIG. 46D are aberration diagrams of the optical system for rigid endoscope of the reference example.

DETAILED DESCRIPTION OF THE INVENTION

Figure 2A:
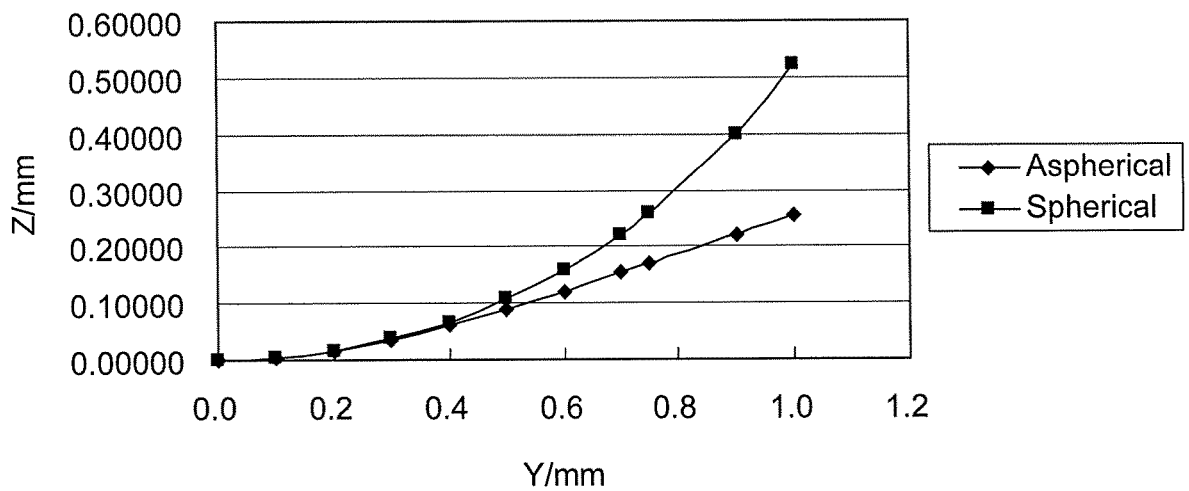
FIG. 2A is a graph indicating an aspherical amount of the object-side surface of the first lens.

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

An objective optical system of the present embodiment includes in order from an object side, a first lens having a negative refractive power and a second lens having a positive refractive power, and the following conditional expressions (1) and (2) are satisfied:

$$-3 < (RL1i + RL1o)/(RL1i - RL1o) < -1.3 \qquad (1)$$

$$30 < vdL1 \qquad (2)$$

where,

RL1o denotes a radius of curvature of an object-side surface of the first lens,

RL1i denotes a radius of curvature of an image-side surface of the first lens, and vdL1 denotes Abbe number for the first lens.

The objective optical system of the present embodiment includes in order from the object side, the first lens having a negative refractive power and the second lens having a positive refractive power. By disposing a lens having a negative refractive power on the object side, it is possible to secure a wide angle of view.

In the objective optical system of the present embodiment, a pupil is positioned in the optical system. By making such arrangement, it is possible to make the optical system small-sized.

For securing the wide angle of view and small-sizing the optical system, it is preferable to make the negative refractive power of the first lens as large as possible. However, when the negative refractive power is made large, both a distortion and a chromatic aberration in particular, are susceptible to become large.

An aberration occurred in the first lens is to be corrected by the second lens. In a case in which it is not possible to carry out the correction adequately, lenses are to be disposed on an image side of the second lens, and the aberration is to be corrected by these lenses.

When an aberration occurs largely at the first lens, since the number of lenses positioned on the image side of the first lens becomes large, the optical system becomes large in size. Therefore, it becomes significant to suppress both an occurrence of the distortion and an occurrence of the chromatic aberration at the first lens.

As mentioned above, particularly the distortion and the chromatic aberration are susceptible to become large at the first lens. For suppressing the occurrence of these aberrations, it is necessary to make appropriate a shape of the first lens and Abbe number for the first lens.

The conditional expression (1) is a conditional expression regulating the shape of the first lens. The shape of the first lens has an effect on the occurrence of the distortion. Therefore, the conditional expression (1) can be said to be a conditional expression related to the distortion occurring at the first lens.

By satisfying the conditional expression (1), the shape of the first lens becomes a meniscus shape having a convex surface directed toward the object side. As a result, it is possible to suppress the occurrence of the distortion at the first lens.

In a case of exceeding an upper limit value of the conditional expression (1), an angle of deviation of an off-axis principal light ray on the object-side surface of the first lens becomes large. Consequently, it becomes difficult to suppress the occurrence of the distortion. Exceeding the upper limit value of the conditional expression (1) is disadvantageous for suppressing the occurrence of the distortion.

In a case of falling below a lower limit value of the conditional expression (1), an angle of deviation of an axial marginal light ray on an image-side surface of the first lens becomes large. In this case, it is possible to suppress the occurrence of the distortion, but correction of a spherical aberration is susceptible to become excessive. Moreover, a spherical aberration of higher order is susceptible to occur. Therefore, falling below the lower limit value of the conditional expression (1) is not preferable.

When the conditional expression (1) is satisfied, it is possible to suppress the occurrence of the distortion and the occurrence of the spherical aberration. Consequently, it is possible to make a numerical aperture of the objective optical system large. As a result, it is possible to realize an objective optical system having a high resolution.

It is possible to capture an image formed by the objective optical system of the present embodiment by an imager. As mentioned above, the objective optical system of the present embodiment has a high resolution. Therefore, by capturing an image formed by the objective optical system by an imager, it is possible to acquire a high-definition image.

The conditional expression (2) is a conditional expression regulating Abbe number for the first lens. Abbe number for the first lens has an effect on the occurrence of the chromatic aberration. Therefore, the conditional expression (2) can be said to be a conditional expression related to the chromatic aberration occurring at the first lens.

In a case of falling below a lower limit value of the conditional expression (2), the chromatic aberration occurring at the first lens becomes large. For correcting the chromatic aberration, it is necessary to dispose a large number of lenses on the image side of the first lens. Consequently, the optical system becomes large in size.

By satisfying the conditional expressions (1) and (2), it is possible to suppress both the occurrence of the distortion and the occurrence of the chromatic aberration even when the negative refractive power of the first lens is made large. As a result, it is possible to achieve both securing of a wide angle of view and small-sizing of the optical system.

It is possible to capture an image formed by the objective optical system of the present embodiment by an imager. In the objective optical system of the present embodiment, the occurrence of the chromatic aberration is suppressed. In this case, chromatic blurring in an image is small. Therefore, by capturing an image formed by the objective optical system of the present embodiment by an imager, it is possible to acquire a high-definition image.

In the objective optical system of the present embodiment, it is preferable that the following conditional expressions (3) and (4) be satisfied:

$$\{\Delta ASPL1i/(ndL1-1)\}/IH < -0.005 \quad (3)$$

$$\{\Delta ASPL1o/(ndL1-1)\}/IH < -0.01 \quad (4)$$

where, $\Delta ASPL1o$ denotes an amount of aspherical displacement at a first height on an object-side surface of the first lens, $\Delta ASPL1i$ denotes an amount of aspherical displacement at a second height on an image-side surface of the first lens, the first height is a height 0.75 times of the maximum image height, the second height is a height 0.25 times of the maximum image height, $ndL1$ denotes a refractive index for a d-line of the first lens, and IH denotes the maximum image height.

As mentioned above, it is possible to capture an image formed by the objective optical system of the present embodiment by an imager. It is preferable that the image acquired by picking up be a high-definition image. For making the image a high-definition image, it is necessary to make the resolution of the optical system high.

It is possible to make the resolution of the optical system high by making the numerical aperture on the object side large. However, when the numerical aperture on the object side is made large, the spherical aberration occurs largely. Therefore, it is necessary to suppress the occurrence of the spherical aberration.

The conditional expression (3) is a conditional expression regulating the amount of aspherical displacement of the image-side surface of the first lens. The conditional expression (4) is a conditional expression regulating the amount of aspherical displacement of the object-side surface of the first lens. A shape of both surfaces of the first lens has an effect on the occurrence of the spherical aberration. Therefore, both the conditional expression (3) and the conditional expression (4) can be said to be conditional expressions related to the spherical aberration occurring at the first lens.

It is possible to express the amount of aspherical displacement with reference to a paraxial spherical surface or a virtual plane provided to an apex of lens. The amount of aspherical displacement is a distance between two points in a direction parallel to an optical axis. One of the points is a point of intersection of a predetermined straight line and the aspherical surface. The other point is a point of intersection of the predetermined straight line and a spherical surface.

The predetermined straight line is a straight line parallel to the optical axis. It is possible to express a distance between the optical axis and the predetermined straight line by using the maximum image height. The amount of aspherical displacement on the object-side surface of the first lens is the amount of aspherical displacement at the first height. The first height is a height 0.75 times of the maximum image height. The amount of aspherical displacement on the image-side surface of the first lens is the amount of aspherical displacement at the second height. The second height is a height 0.25 times of the maximum image height.

In a case of expressing the amount of aspherical displacement with reference to the virtual plane, the amount of aspherical displacement is a difference between an amount of aspherical sag and an amount of spherical sag. The amount of aspherical sag is expressed as a distance between the virtual plane and the aspherical surface. The amount of spherical sag is expressed as a distance between the virtual plane and the spherical surface. In a case of expressing the amount of aspherical displacement with reference to the paraxial spherical surface, the amount of aspherical displacement is expressed as a distance between the paraxial spherical surface and the aspherical surface.

In the objective optical system of the present embodiment, both the object-side surface of the first lens and the image-side surface of the first lens are aspherical surfaces having a shape such that a refractive power becomes smaller from a center toward a periphery. In other words, the image-side surface of the first lens is an aspherical surface having a shape such that the negative refractive power becomes smaller from the center toward the periphery. The object-side surface of the first lens is an aspherical surface having a shape such that the positive refractive power becomes smaller from the center toward the periphery.

An example of the shape of the aspherical surface will be shown. Here, an objective optical system of an example 1 to be described later will be used. FIG. 1A and FIG. 1B are data related to the aspherical surface of the object-side surface of the first lens.

In FIG. 1A, values of a radius of curvature, values of a conical coefficient, and values of an aspherical coefficient are indicated. In the objective optical system of the example 1, the object-side surface of the first lens is an aspherical surface having a fourth-order aspherical coefficient and a sixth-order aspherical coefficient. In a spherical surface, the value of the conical coefficient and the values of the aspherical coefficients are zero.

In FIG. 1B, values of the amount of sag of the aspherical surface are shown in a column of 'Aspherical', values of the amount of sag of the spherical surface are shown in a column of 'Spherical', and values of the amount of aspherical displacement are shown in a column of 'Difference'. Moreover, Y indicates a distance between the optical axis and the predetermined straight line.

Figure 2B:
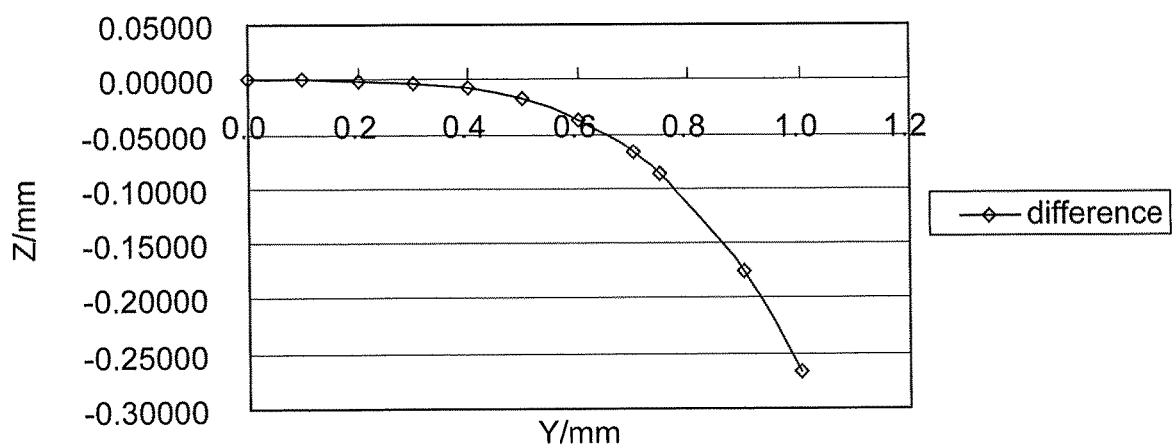
FIG. 2B is a graph indicating an aspherical amount of the object-side surface of the first lens.

FIG. 2A and FIG. 2B are graphs showing an aspherical amount of the object-side surface of the first lens. In FIG. 2A, a curve indicating an amount of sag of the aspherical surface and a curve indicating an amount of sag of the spherical surface are shown. In FIG. 2B, a curve indicating an amount of aspherical displacement is shown.

The two curves shown in FIG. 2A are curves drawn on the basis of values in the column of 'Aspherical' and values in the column of 'Spherical' in FIG. 1B. The curve shown in FIG. 2B is a curve drawn on the basis of the values in the column of 'Difference'.

From the two curves shown in FIG. 2A, it is easily revealed that in the objective optical system of the present embodiment, the object-side surface of the first lens is an aspherical surface having a shape such that the positive refractive power becomes smaller from a center toward a periphery.

Figure 4A:
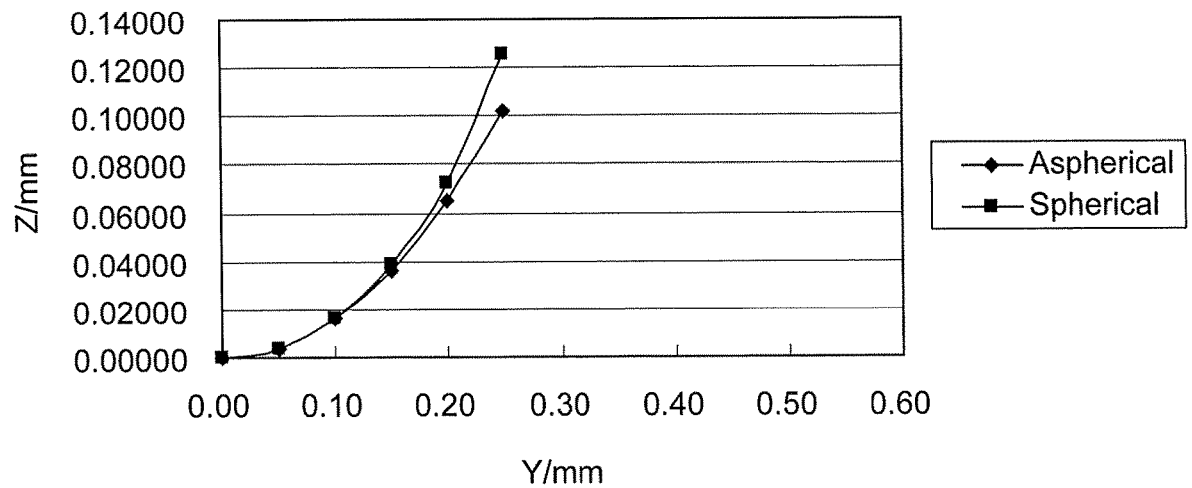
FIG. 4A is a graph indicating an aspherical amount of the image-side surface of the first lens.
Figure 4B:
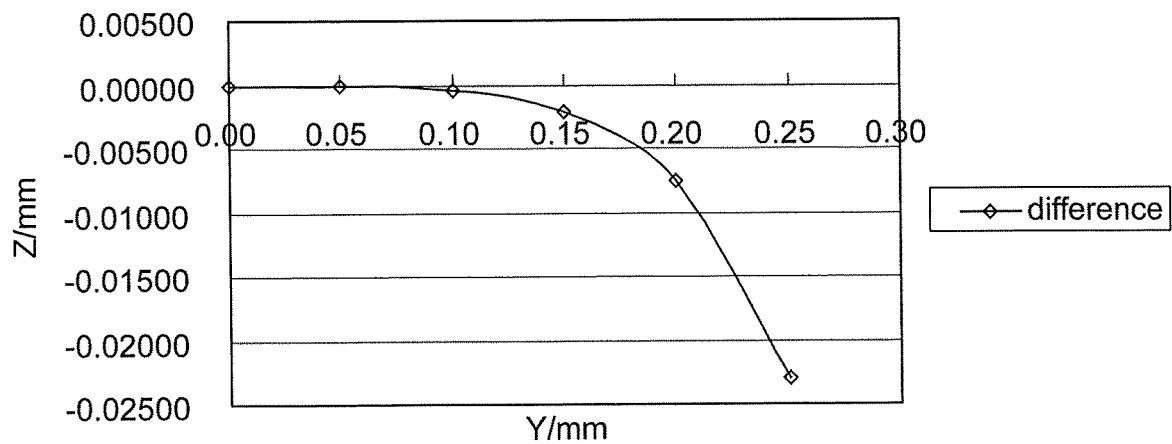
FIG. 4B is a graph indicating an aspherical amount of the image-side surface of the first lens.

FIG. 3A and FIG. 3B are data related to the aspherical surface of the image-side surface of the first lens. Both FIG. 4A and FIG. 4B are graphs indicating an aspherical amount of the image-side surface of the first lens. In FIG. 4A, a curve indicating an amount of sag of the aspherical surface and a curve indicating an amount of sag of the spherical surface are shown. In FIG. 4B, a curve indicating an amount of aspherical displacement is shown. Description in detail of each diagram is omitted here.

From the two curves shown in FIG. 4A, it is easily revealed that in the objective optical system of the present embodiment, the image-side surface of the first lens is an aspherical surface having a shape such that the negative refractive power becomes smaller from a center toward a periphery.

In a case of satisfying the conditional expression (3), it is possible to make the image-side surface of the first lens an aspherical surface having a shape which enables both the suppression of the occurrence of the spherical aberration and a favorable correction of the distortion. In a case of satisfying the conditional expression (4), it is possible to make the object-side surface of the first lens an aspherical surface having a shape which enables to suppress the occurrence of the spherical aberration. In the case of satisfying the conditional expression (4), it is not possible to achieve an effect of correction of the distortion.

In a case of exceeding an upper limit value of the conditional expression (3), the amount of aspherical displacement becomes inadequate. In this case, the spherical aberration occurring at the first lens is susceptible to become large. Moreover, suppression of the occurrence of the distortion also becomes difficult. Exceeding the upper limit value of the conditional expression (3) is disadvantageous for the correction of the distortion.

In a case of exceeding an upper limit value of the conditional expression (4), the amount of aspherical displacement becomes inadequate. In this case, the spherical aberration occurring at the first lens is susceptible to become large.

By satisfying conditional expressions (3) and (4) simultaneously, it is possible to make small the spherical aberration occurring at the first lens while correcting the distortion favorably. By making the spherical aberration occurring at the first lens small, it is possible to make the number of lenses to be disposed on the image side of the first lens small. As a result, it is possible to make the optical system small-sized.

At a time of manufacturing and assembling an optical system, lenses are decentered due to a manufacturing error and an assembling error. When the spherical aberration occurring at the first lens is small, it is possible make small an aberration occurring due to decentration of the lenses. For instance, it is possible to suppress an occurrence of a decentration coma. Consequently, it is possible to suppress a degradation of an imaging performance.

Moreover, when the spherical aberration occurring in the first lens is small, it is possible to make a manufacturing error sensitivity low. Consequently, it is possible to make small a variation in aberration for each product. In such manner, the small spherical aberration occurring in the first lens is advantageous for a quality of product.

By satisfying conditional expressions (3) and (4) simultaneously, it is possible to suppress the occurrence of the spherical aberration. Consequently, it is possible to make the numerical aperture of the objective optical system large. As a result, it is possible to realize an objective optical system having a high resolution.

It is possible to capture an image formed by the objective optical system of the present invention by an imager. The objective optical system of the present embodiment has a high resolution. Therefore, by capturing an image formed by the objective optical system of the present embodiment by an imager, it is possible to acquire a high-definition image.

The amount of aspherical displacement RASP is expressed by the following expression, including reference numerals as well. A direction of the optical axis is z, a direction orthogonal to the optical axis is y, a paraxial radius of curvature is RDY, the conical coefficient is K, and the aspherical coefficients are AC4, AC6, AC8, and AC10. In the following expression '·' denotes multiplication.

$$\Delta ASP = Z\_ASP - Z\_SPH$$

$$Z\_ASP = \frac{\left(\frac{1}{RDY}\right) \cdot Y^2}{1 + \sqrt{1 - (K+1) \cdot \left(\frac{1}{RDY}\right)^2 \cdot Y^2}} + AC2 \cdot Y^2 + AC4 \cdot Y^4 +$$

$$AC6 \cdot Y^6 + AC8 \cdot Y^8 + AC10 \cdot Y^{10}$$

$$Z\_SHP = \frac{\left(\frac{1}{RDY}\right) \cdot Y^2}{1 + \sqrt{1 - \left(\frac{1}{RDY}\right)^2 \cdot Y^2}}$$

In the objective optical system of the present embodiment, it is preferable that the following conditional expression (5) be satisfied.

$$0.005 < \{\Delta ASPL2i/(ndL2-1)\}/IH \qquad (5)$$

where, $\Delta ASPL2i$ denotes an amount of aspherical displacement at a third height on an image-side surface of the second lens, the third height is a height 1 times of the maximum image height, ndL2 denotes a refractive index for a d-line of the second lens, and IH denotes the maximum image height.

Figure 6A:
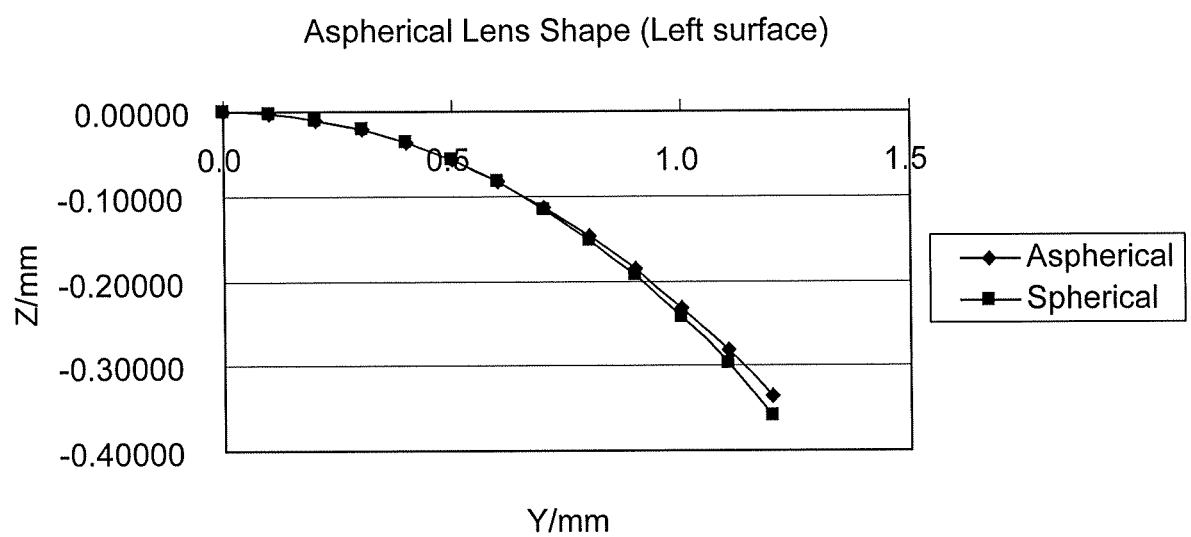
FIG. 6A is a graph indicating an aspherical amount of the image-side surface of the second lens.
Figure 6B:
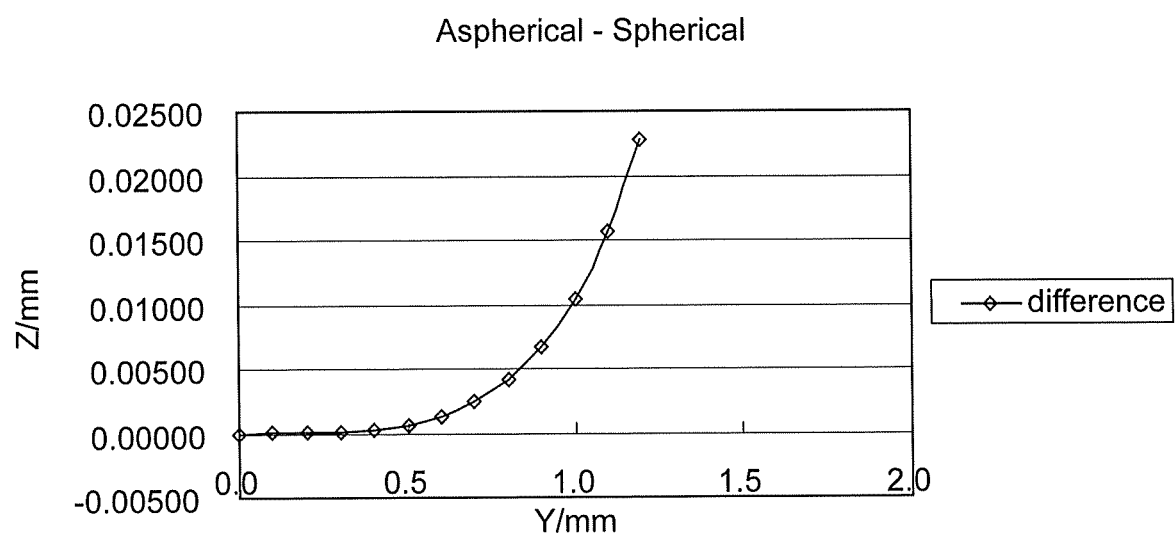
FIG. 6B is a graph indicating an aspherical amount of the image-side surface of the second lens.
Figure 7:
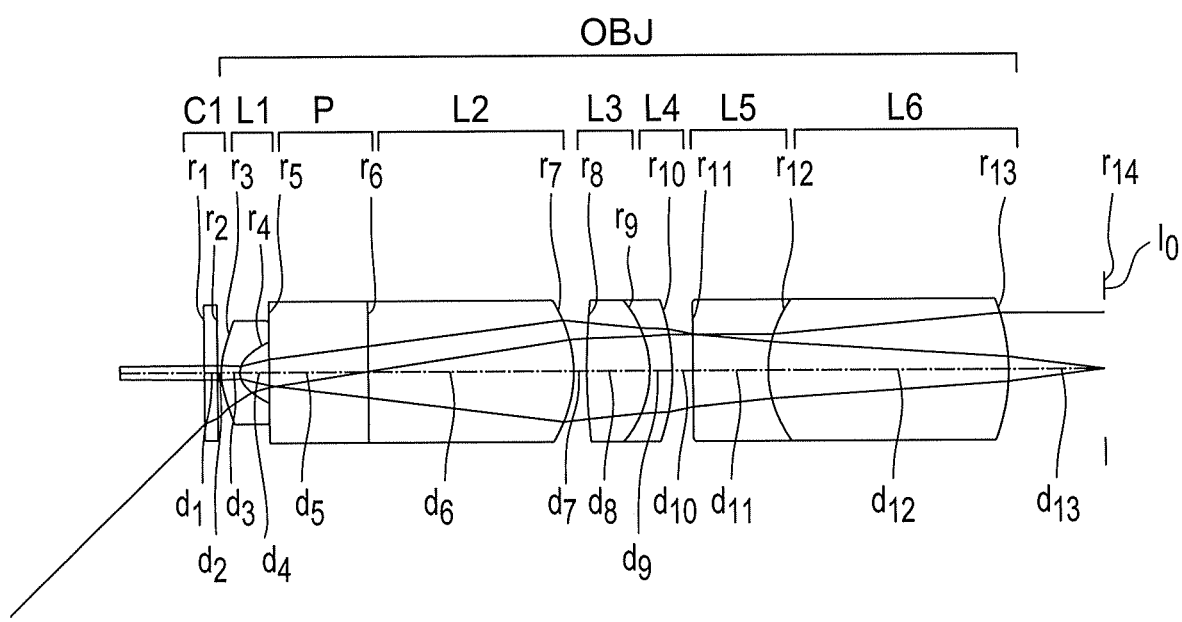
FIG. 7 is a lens cross-sectional view of an objective optical system of an example 1.
Figure 8:
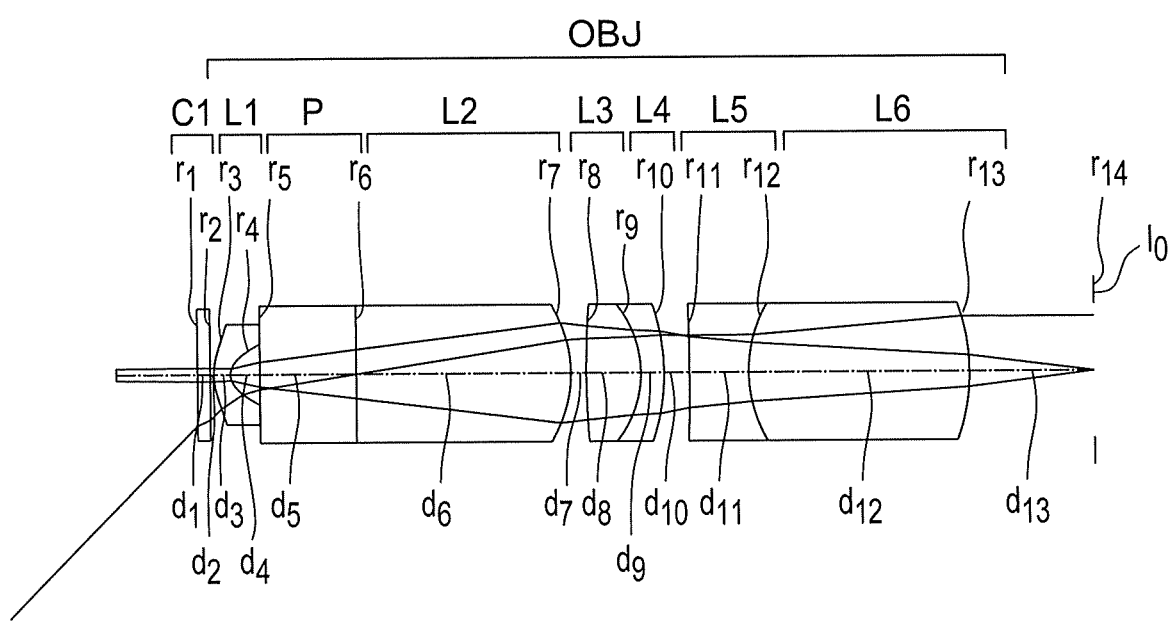
FIG. 8 is a lens cross-sectional view of an objective optical system of an example 2.
Figure 9:
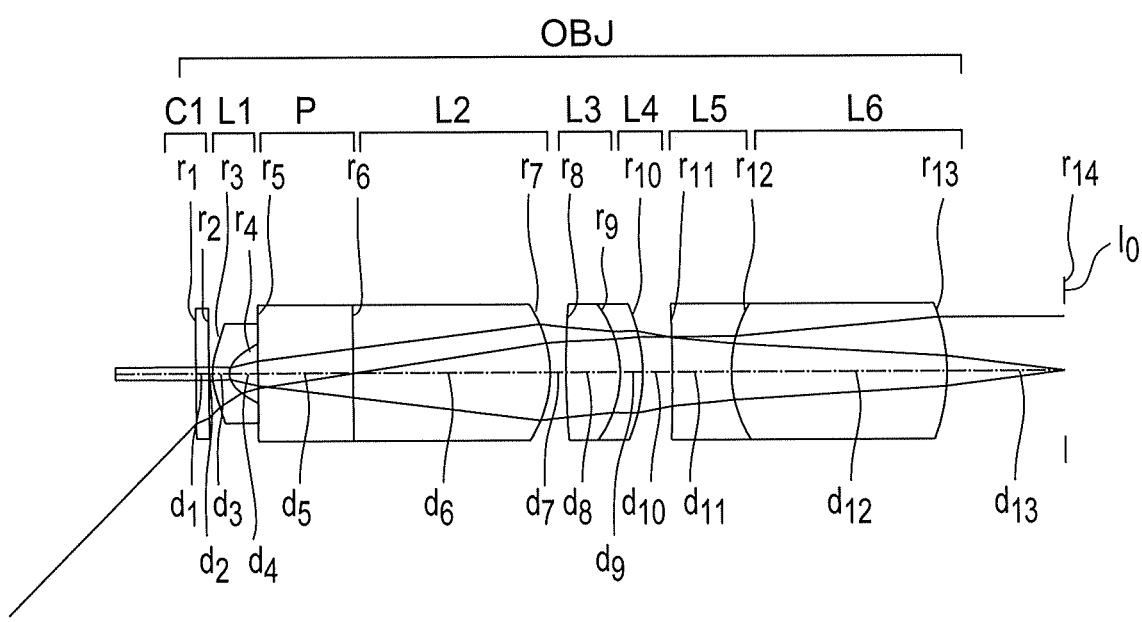
FIG. 9 is a lens cross-sectional view of an objective optical system of an example 3.
Figure 10:
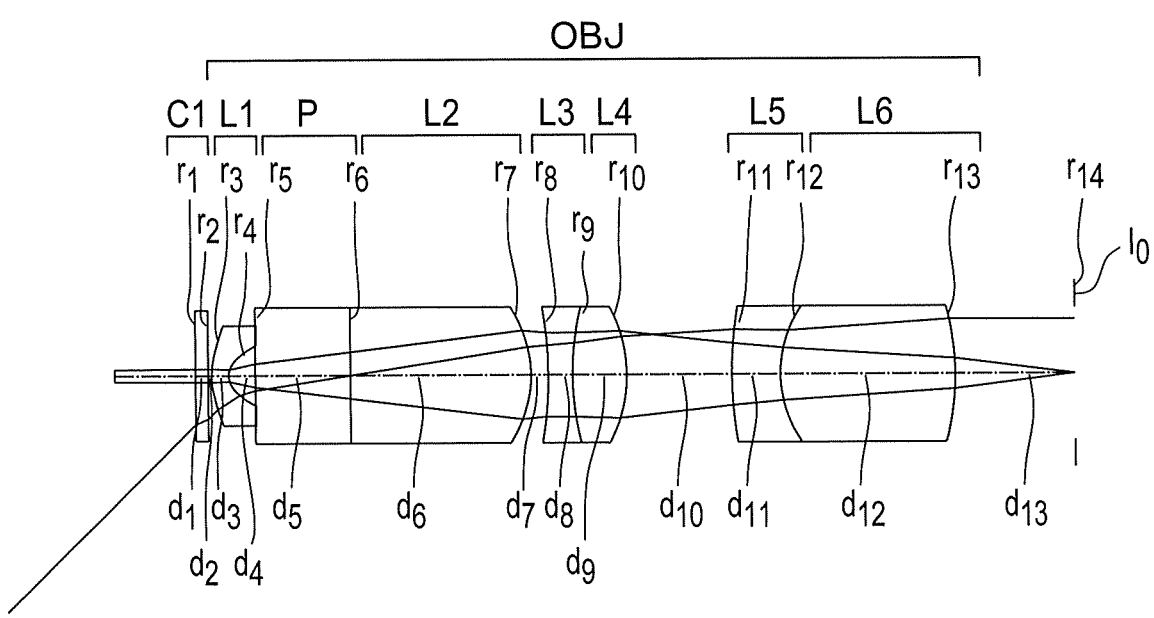
FIG. 10 is a lens cross-sectional view of an objective optical system of an example 4.
Figure 11:
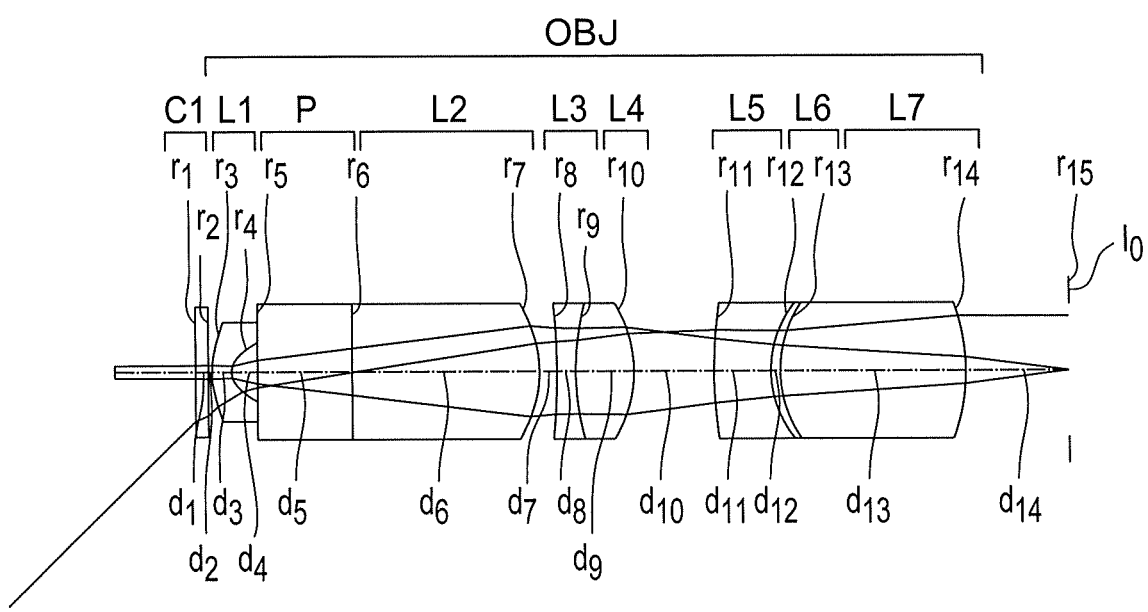
FIG. 11 is a lens cross-sectional view of an objective optical system of an example 5.
Figure 12:
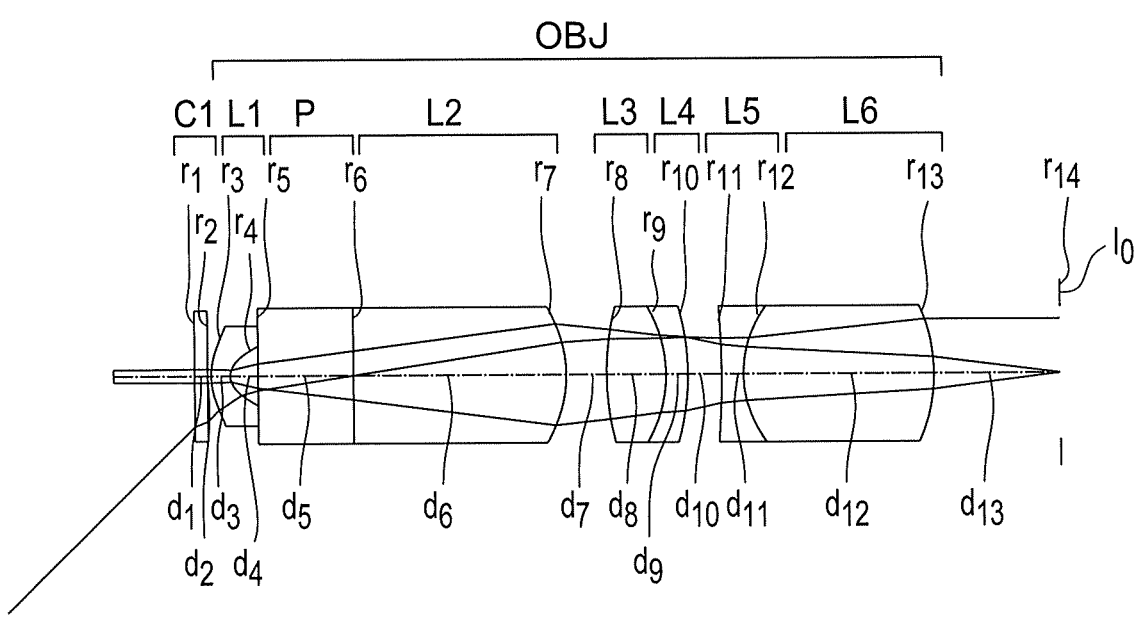
FIG. 12 is a lens cross-sectional view of an objective optical system of an example 6.
Figure 13:
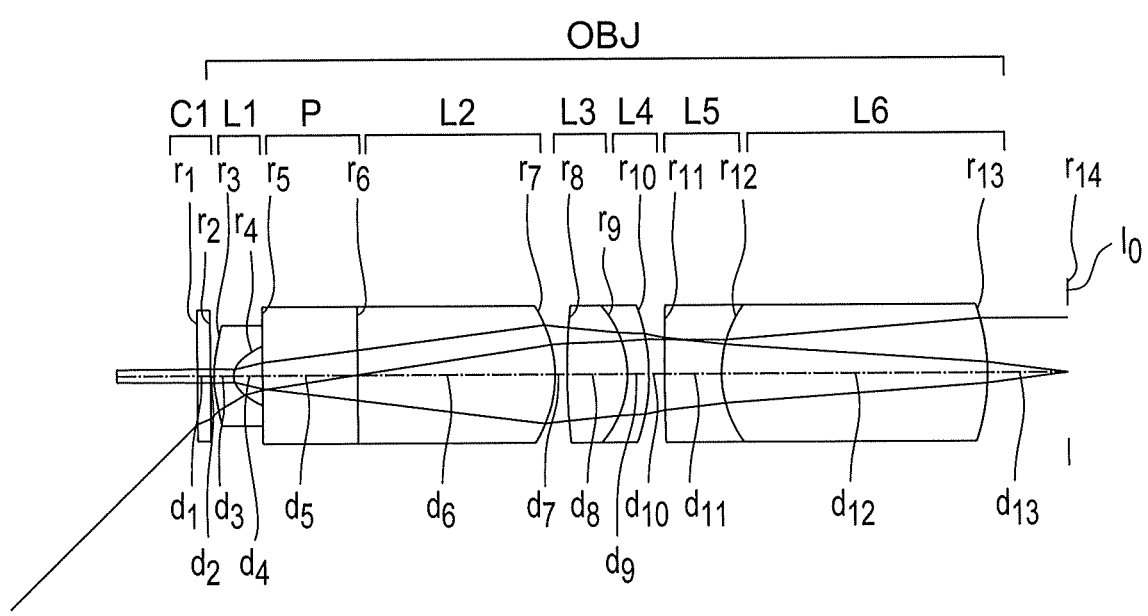
FIG. 13 is a lens cross-sectional view of an objective optical system of an example 7.
Figure 14:
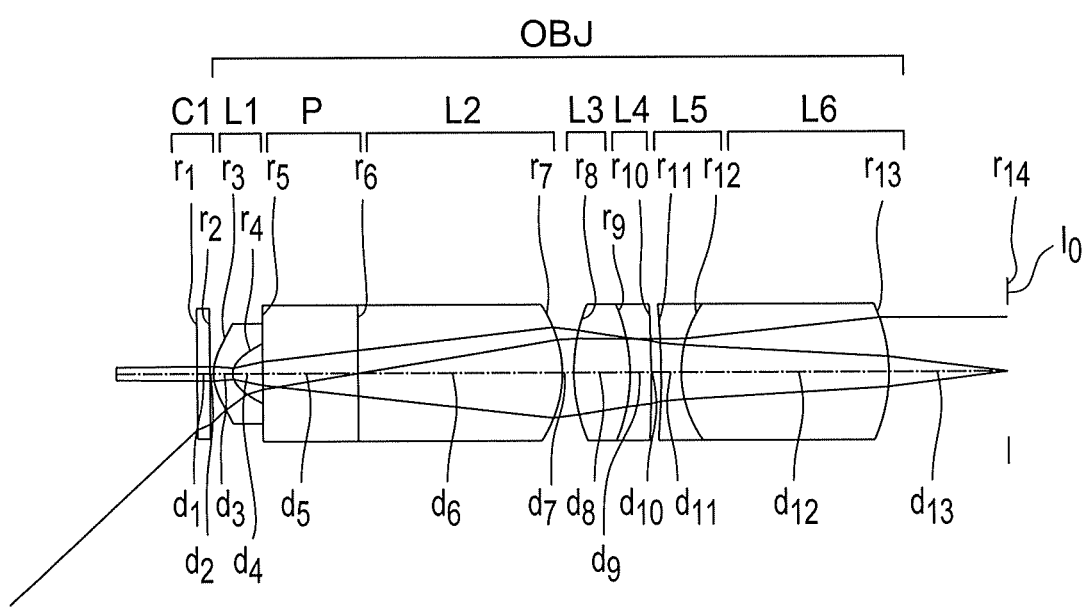
FIG. 14 is a lens cross-sectional view of an objective optical system of an example 8.
Figure 15:
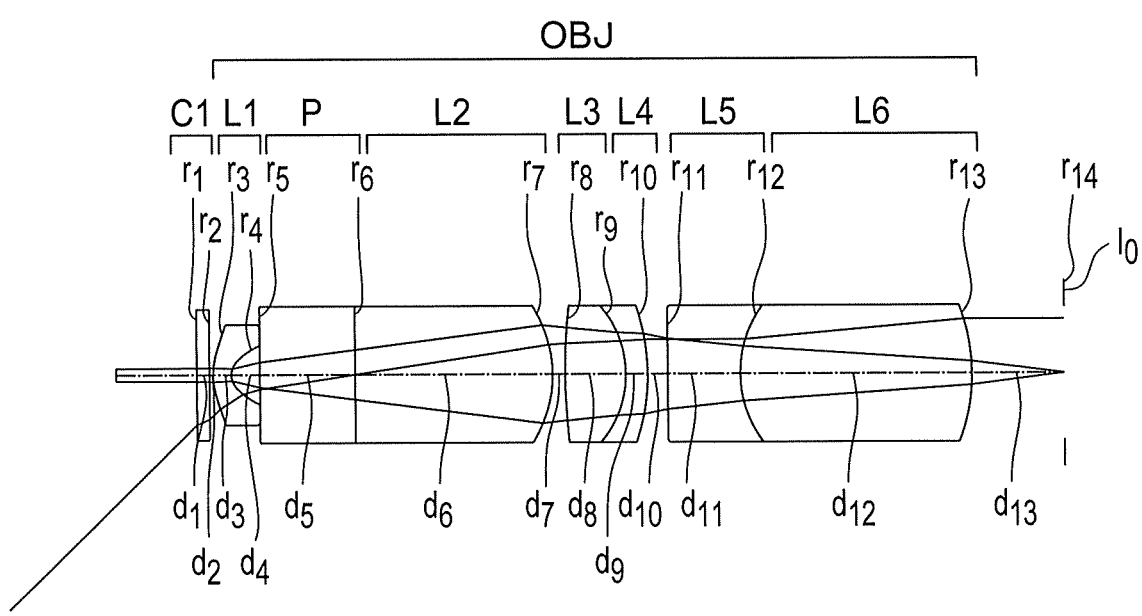
FIG. 15 is a lens cross-sectional view of an objective optical system of an example 9.

FIG. 5A and FIG. 5B are data related to the aspherical surface of an image-side surface of the second lens. Both FIG. 6A and FIG. 6B are graphs indicating an aspherical amount of the image-side surface of the second lens. In FIG. 6A, a curve indicating an amount of sag of the aspherical surface and a curve indicating an amount of sag of the spherical surface are shown. In FIG. 6B, a curve indicating an amount of aspherical displacement is shown. Description in detail of each diagram is omitted here.

From the two curves shown in FIG. 6A, it is easily revealed that in the objective optical system of the present embodiment, the image-side surface of the second lens is an aspherical surface having a shape such that the positive refractive power becomes smaller from a center toward a periphery.

The conditional expression (5) is a conditional expression regulating the amount of aspherical displacement of the image-side surface of the second lens. A shape of the image-side surface of the second lens has an effect on the occurrence of the spherical aberration. The conditional expression (5) can be said to be a conditional expression related to the spherical aberration occurring at the second lens.

In the objective optical system of the present embodiment, the image-side surface of the second lens is an aspherical surface having a shape such that the refractive power becomes smaller from the center toward the periphery. In other words, the image-side surface of the second lens is an aspherical surface having a shape such that the positive refractive power becomes smaller from the center toward the periphery.

By satisfying the conditional expression (5), it is possible to make small the spherical aberration occurring in the second lens. When the spherical aberration occurring in the second lens is small, it is possible to make small an aberration due to a decentration of lens. For instance, it is possible to suppress the occurrence of the decentration coma. Consequently, it is possible to suppress a degradation of imaging performance.

Moreover, when the spherical aberration occurring in the second lens is small, it is possible to make the manufacturing error sensitivity small. Consequently, it is possible to make small the variation in aberration for each product. In such manner, the small spherical aberration occurring in the second lens is advantageous for the quality of product.

In a case of falling below a lower limit value of the conditional expression (5), the amount of aspherical displacement becomes inadequate. In this case, the spherical aberration occurring in the second lens is susceptible to become large.

By satisfying conditional expressions (3), (4), and (5) simultaneously, an aberration due to a relative decentration of the first lens and the second lens also becomes small. Consequently, it is possible to suppress the degradation of imaging performance. Moreover, it is possible to make the manufacturing error sensitivity low. Consequently, it is possible to make small the variation in aberration for each product. Satisfying conditional expressions (3), (4), and (5) simultaneously is preferable for the quality of product.

As it will be described later, it is possible to use the objective optical system of the present embodiment with a relay optical system. In this case, an image formed by the objective optical system of the present embodiment is relayed by the relay optical system. An image captured by an imager is an image formed by the relay optical system.

A size of the image formed by the relay optical system may differ from a size of the image formed by the objective optical system of the present embodiment. Here, IH in conditional expressions (3), (4), and (5) is the maximum image height for the image formed by the objective optical system of the present embodiment.

It is preferable that the objective optical system of the present embodiment include a third lens, the third lens be a cemented lens having a positive lens and a negative lens, and the following conditional expressions (6) and (7) be satisfied:

$$0 < ndL3n - ndL3p < 0.2 \qquad (6)$$

$$\theta gFL3n - \theta gFL3p < 0.06 \qquad (7)$$

where, ndL3p denotes a refractive index for a d-line of the positive lens, ndL3n denotes a refractive index for a d-line of the negative lens, θgFL3p denotes a partial dispersion ratio of the positive lens, θgFL3n denotes a partial dispersion ratio of the negative lens, $$\theta gFL3p=(ngL3p-nFL3p)/(nFL3p-nCL3p),$$

$$\theta gFL3n=(ngL3n-nFL3n)/(nFL3n-nCL3n),$$

each of ngL3p, nFL3p, nCL3p denotes a refractive index of the positive lens for a g-line, an F-line, and a C-line respectively, and each of ngL3n, nFL3n, and nCL3n denotes a refractive index of the negative lens for a g-line, an F-line, and a C-line respectively.

The conditional expression (6) is a conditional expression regulating the refractive index of the positive lens and the refractive index of the negative lens. A shape of a lens surface varies according to the refractive index of the lens. As mentioned above, the shape of the lens has an effect on the occurrence of the spherical aberration. Therefore, the conditional expression (6) can be said to be a conditional expression related to a spherical aberration occurring in the third lens.

In a case of exceeding an upper limit value of the conditional expression (6), a positive spherical aberration occurring at a cemented surface becomes large. Moreover, in a case of falling below a lower limit value of the conditional expression (6), a negative spherical aberration occurring at the cemented surface becomes large. In both the cases, it becomes difficult to prevent the degradation of imaging performance. Moreover, it becomes difficult to make low the manufacturing error sensitivity. Consequently, it becomes difficult to make small the variation in aberration for each product.

The conditional expression (7) is a conditional expression regulating the partial dispersion ratio of the positive lens and the partial dispersion ratio of the negative lens. It is possible to correct the chromatic aberration by the positive lens and the negative lens. Consequently, the conditional expression (7) can be said to be a conditional expression related to the chromatic aberration occurring in the objective optical system.

In the third lens, a height of an axial marginal light ray is high. Therefore, the third lens is appropriate for correction of a secondary spectrum which is a longitudinal chromatic aberration. By satisfying the conditional expression (7), it is possible to correct the secondary spectrum favorably.

In a case of exceeding an upper limit value of the conditional expression (7), correction of the secondary spectrum is susceptible to be inadequate.

The objective optical system of the present embodiment includes in order from an object side, a first lens having a negative refractive power, a second lens having a positive refractive power, and a third lens, the third lens is a cemented lens having a positive lens and a negative lens, and the following conditional expressions (1), (2), (3), (4), (5), (6), and (7) are satisfied:

$$-3<(RL1i+RL1o)/(RL1i-RL1o)<-1.3 \quad (1)$$

$$30<vdL1 \quad (2)$$

$$\{\Delta ASPL1i/(ndL1-1)\}/IH<-0.005 \quad (3)$$

$$\{\Delta ASPL1o/(ndL1-1)\}/IH<-0.01 \quad (4)$$

$$0.005<\{\Delta ASPL2i/(ndL2-1)\}/IH \quad (5)$$

$$0<ndL3n-ndL3p<0.2 \quad (6)$$

$$\theta gFL3n-\theta gFL3p<0.06 \quad (7)$$

where,

RL1o denotes the radius of curvature of the object-side surface of the first lens, RL1i denotes the radius of curvature of the image-side surface of the first lens, vdL1 denotes the Abbe number for the first lens, ΔASPL1o denotes the amount of aspherical displacement at the first height on the object-side surface of the first lens, ΔASPL1i denotes the amount of aspherical displacement at the second height on the image-side surface of the first lens, ΔASPL2i denotes the amount of aspherical displacement at the third height on the image-side surface of the second lens, the first height is a height 0.75 times of the maximum image height, the second height is a height 0.25 times of the maximum image height, the third height is a height 1 times of the maximum image height, ndL1 denotes the refractive index for the d-line of the first lens, ndL2 denotes the refractive index for the d-line of the second lens IH denotes the maximum image height, ndL3p denotes the refractive index for the d-line of the positive lens, ndL3n denotes the refractive index for the d-line of the negative lens, θgFL3p denotes the partial dispersion ratio of the positive lens, θgFL3n denotes the partial dispersion ratio of the negative lens, $$\theta gFL3p=(ngL3p-nFL3p)/(nFL3p-nCL3p),$$

$$\theta gFL3n=(ngL3n-nFL3n)/(nFL3n-nCL3n),$$

each of ngL3p, nFL3p, nCL3p denotes the refractive index of the positive lens for the g-line, the F-line, and the C-line respectively, and each of ngL3n, nFL3n, and nCL3n denotes the refractive index of the negative lens for the g-line, the F-line, and the C-line respectively.

According to the objective optical system of the present embodiment, it is possible to correct both the distortion and the chromatic aberration favorably, while being small-sized and having a wide angle of view and a high resolution.

It is preferable that the objective optical system of the present embodiment include a resin lens.

By using the resin lens, it is possible to correct the secondary spectrum favorably.

It is preferable that the objective optical system of the present embodiment include a cemented lens, and the cemented lens include a resin lens.

When one of the lenses to be cemented is made to be a resin lens which is thin in thickness, by using the method of curing the resin that will be described later, it is possible to fix the thin resin lens and the other lens. In this method, a cementing material may not be interposed between the two lenses. A cementing material may be interposed between the two lenses, and the thin resin lens and the other lens may be fixed.

By making such arrangement, it is possible to make small the decentering which occurs between the two lenses. Moreover, it is possible to make the lenses further thinner.

In a case in which one of the lenses of the cemented lens is a resin lens, it is possible to use the method of fixing two lenses by curing a resin. In this method, the resin lens is cured upon bringing in close contact with a surface of other lens.

In curing upon bringing in close contact, a liquid resin such as an ultraviolet cure resin is to be used. As a lens material of the resin lens, a material such as an ultraviolet cure resin is available. A desired amount of the ultraviolet cure resin is to be discharged on to a refractive surface of the other lens. Accordingly, the ultraviolet cure resin is in a state of making a contact with the refractive surface of the other lens. Of surfaces of the ultraviolet cure resin, a surface in contact with the refracting surface of the other lens is one refracting surface of the resin lens.

A mold is disposed at a position facing the other lens, sandwiching the ultraviolet cure resin. The mold is pressed against the ultraviolet cure resin. The ultraviolet cure resin assumes a state of being sandwiched between the mold and the other lens. In this state, ultraviolet rays are irradiated from a other lens side. Accordingly, the ultraviolet cure resin is cured.

The mold has a molding surface. The molding surface is a surface in contact with the ultraviolet cure resin. A shape of the molded surface is same as a shape of the other refracting surface of the resin lens. Of the surfaces of the ultraviolet cure resin, a surface in contact with the molded surface is the other refracting surface of the resin lens.

In such manner, in curing up on bringing in close contact, the one refracting surface of the resin lens is formed by the refracting surface of the other lens, and the other refracting surface of the resin lens is formed by the molded surface of the mold.

A material of the resin lens is not restricted to the ultraviolet cure resin. The method of curing is also not restricted to a method in which the ultraviolet rays are irradiated.

By curing upon bringing in close contact, it is possible to make small a surface-shape error and a decentering error. Furthermore, it is possible to make the lens thin.

An optical system for rigid endoscope of the present embodiment includes the objective optical system of the present embodiment, a relay optical system, and an eyepiece optical system.

According to the optical system for rigid endoscope of the present embodiment, it is possible to realize an optical system for rigid endoscope which, while being small-sized, has a wide angle of view and a high resolution, and in which both the distortion and the chromatic aberration are corrected favorably.

It is possible to capture an image formed by the optical system for rigid endoscope of the present embodiment by an imager for example. The optical system for rigid endoscope of the present embodiment has a high resolution, and also the occurrence of the chromatic aberration is suppressed. Therefore, by capturing an image formed by the optical system for rigid endoscope of the present embodiment by an imager, it is possible to acquire a high-definition image.

In the optical system for rigid endoscope of the present embodiment, it is preferable that at least one of the objective optical system and the relay optical system include a resin lens.

By using the resin lens, it is possible to correct the secondary spectrum favorably.

In the optical system for rigid endoscope of the present embodiment, it is preferable that the relay optical system include an object-side lens, an image-side lens, a plurality of cemented lenses, and a diffractive optical element.

Abbe number in a visible range of the diffraction optical element is −3.453. In such manner, the diffraction optical element has extremely strong negative dispersion characteristics. Whereas, Abbe number of an ordinary glass material is approximately 20 to 95. Therefore, it is evident that the diffractive optical element has extremely strong dispersion characteristics opposite to a normal glass material. Moreover, by a similar calculation, it is evident that the diffractive optical element has an abnormal dispersibility.

In the relay optical system, the diffractive optical element is disposed between the object-side lens and the image-side lens. By using the diffractive optical element, an aberration correction in which the dispersion characteristics opposite to that of a glass material are used, is possible. In other words, it is possible to cancel the longitudinal chromatic aberration occurred at the cemented lens by the diffractive optical element.

However, in a normal glass and resin, the dispersion is nonlinear with respect to wavelength. Whereas, in a diffractive optical element, the dispersion is linear with respect to wavelength. Consequently, in a case in which the number of lenses in an optical system is small, only by using just a diffractive optical element, the chromatic aberration is not corrected adequately in a wavelength range of white light.

The relay optical system, as a dioptric system, includes an object-side lens, a plurality of cemented lenses, and an image-side lens. By using a plurality of lenses in the dioptric system in such manner, it is possible to bring the dispersion in the dioptric system closer to linear dispersion. As a result, it is possible to carry out the correction of the chromatic aberration effectively by the diffractive optical element.

Moreover, by disposing the diffractive optical element between an object-side lens and an image-side lens, it is possible to make a light ray incident on the diffractive optical element to be almost perpendicular. As a result, it is possible to improve a diffraction efficiency.

A rigid endoscope of the present embodiment includes the optical system for rigid endoscope of the present embodiment and an illumination optical system.

According to the rigid endoscope of the present embodiment, it is possible to observe an optical image in which the distortion and the chromatic aberration are corrected favorably, while being small-sized and having a wide angle of view and a high resolution.

It is possible to combine the rigid endoscope of the present embodiment with an image pickup apparatus for example. In this case, it is possible to capture an image formed by the optical system for rigid endoscope by an imager. The optical system for rigid endoscope of the present embodiment has a high resolution, and in which the occurrence of the chromatic aberration is suppressed. Therefore, by capturing an image formed by the optical system for rigid endoscope of the present embodiment by an imager, it is possible to acquire a high-definition image.

Examples of the objective optical system, the optical system for rigid endoscope, and the rigid endoscope will be described below in detail by referring to the accompanying diagrams. However, the present invention is not restricted to the examples described below.

A reference example of the objective optical system and a reference example of the optical system for rigid endoscope will also be described below in detail by referring to the accompanying diagrams. The optical system of the reference example is an optical system not satisfying conditional expression (1). In a case of not satisfying conditional expression (1), it is difficult to achieve both of the correction of the distortion and the correction of the spherical aberration. Consequently, in the optical system of the reference example, the correction of the distortion is inadequate.

Figure 16:
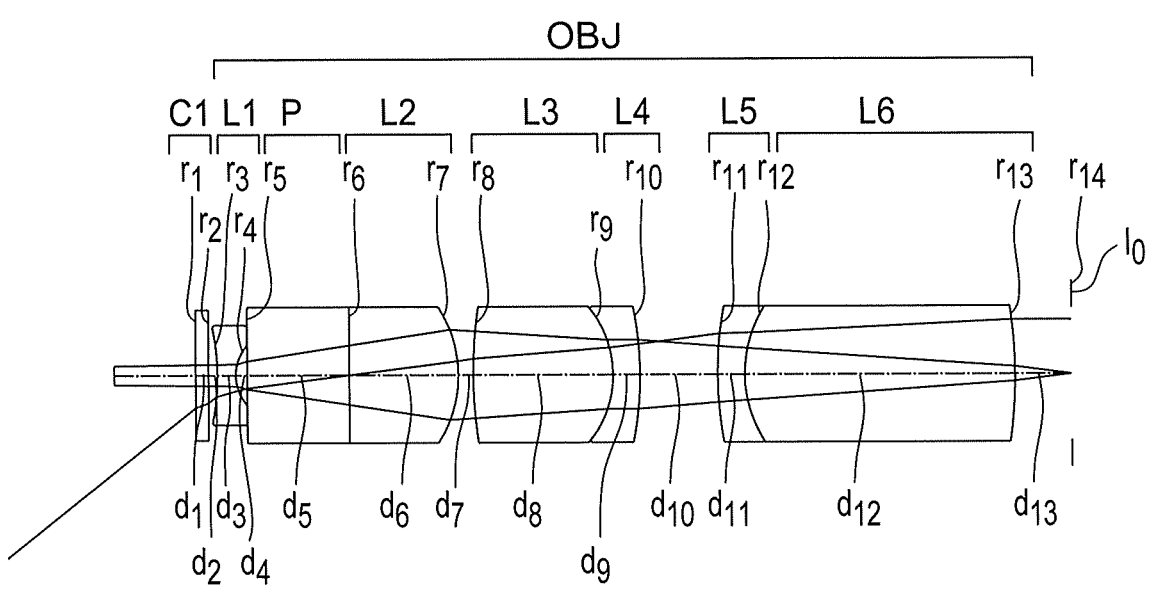
FIG. 16 is a lens cross-sectional view of an objective optical system of a reference example.
Figures 17A, 17B, 17C, 17D:
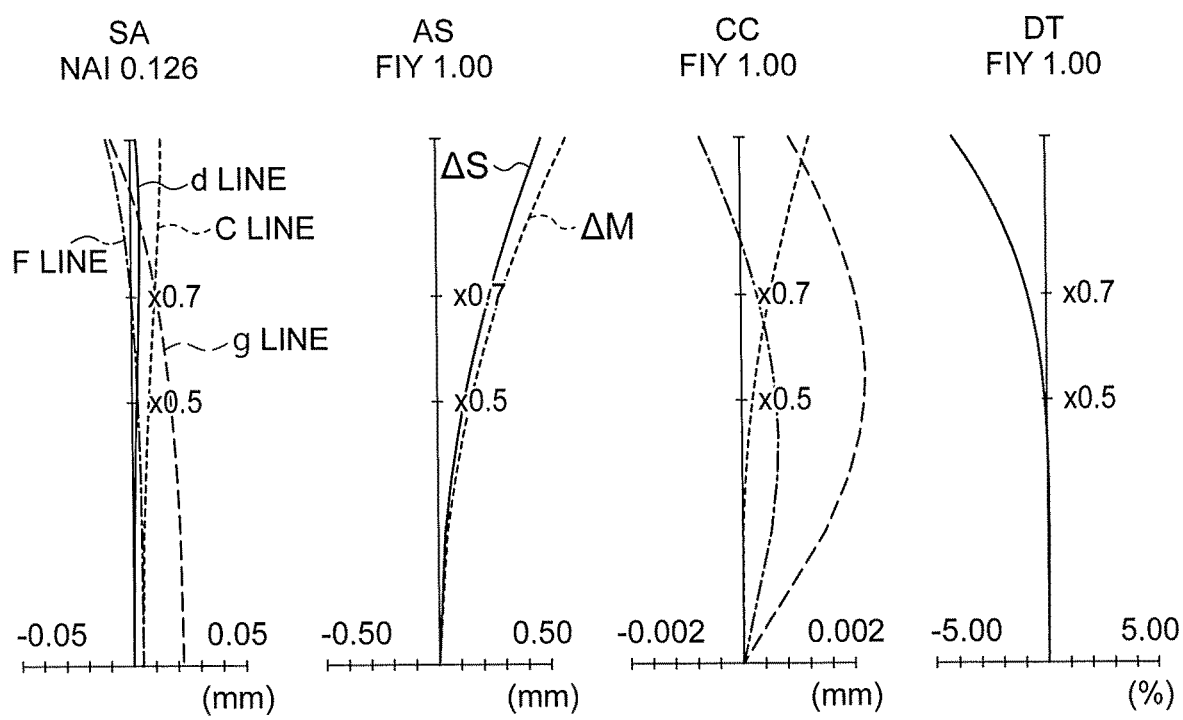
FIG. 17A, FIG. 17B, FIG. 17C, and FIG. 17D are aberration diagrams of the objective optical system of the example 1.
Figures 23A, 23B, 23C, 23D:
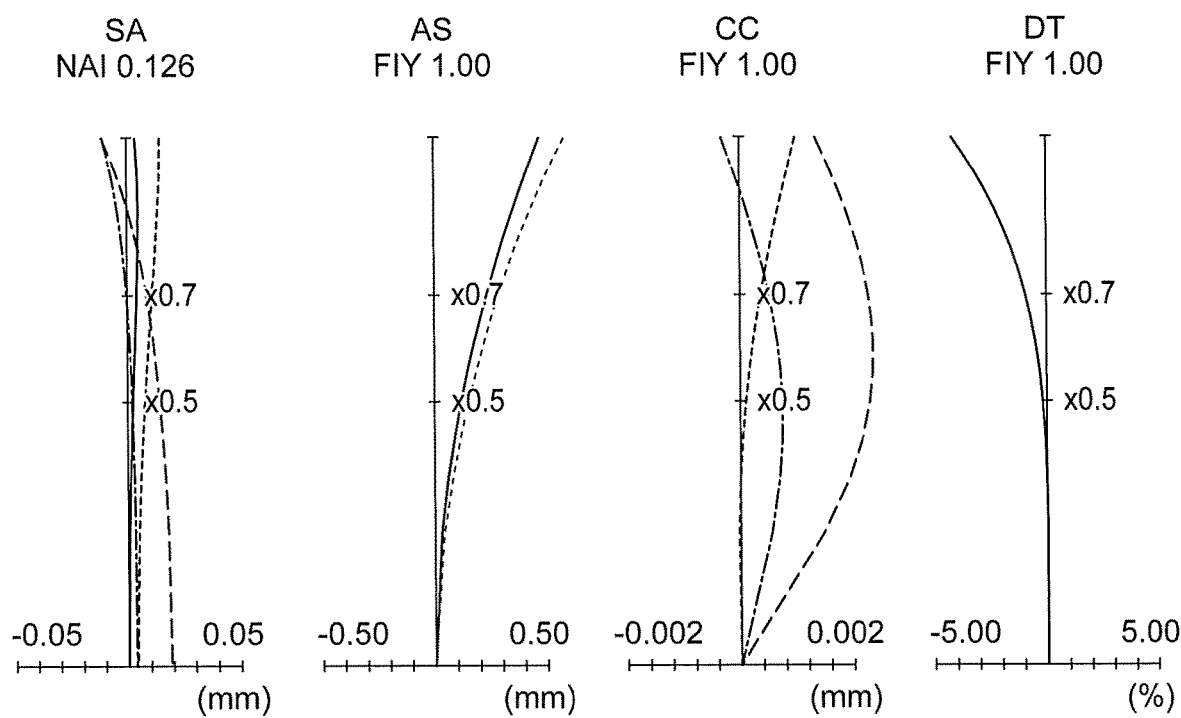
FIG. 23A, FIG. 23B, FIG. 23C, and FIG. 23D are aberration diagrams of the objective optical system of the example 7.

Examples of the objective optical system will be described below. FIG. 7, FIG. 8, FIG. 9, FIG. 10, FIG. 11, FIG. 12, FIG. 13, FIG. 14, and FIG. 15 are lens cross-sectional views of objective optical systems of the examples. FIG. 16 is a lens cross-sectional view of an objective optical system of a reference example.

In lens cross-sectional views of the examples and lens cross-sectional view of the reference example, an axial marginal light ray and a principal light ray at the maximum image height are shown. Here, Io denotes an image of an object. As it will be described later, in a case of using the objective optical system together with the relay optical system, Io is a primary image. IH is the maximum image height of the primary image Io.

Aberration diagrams of the objective optical system of each example will be described below.

FIG. 17A, FIG. 18A, FIG. 19A, FIG. 20A, FIG. 21A, FIG. 22A, FIG. 23A, FIG. 24A, and FIG. 25A show a spherical aberration (SA) of the objective optical systems of the examples.

FIG. 17B, FIG. 18B, FIG. 19B, FIG. 20B, FIG. 21B, FIG. 22B, FIG. 23B, FIG. 24B, and FIG. 25B show an astigmatism (AS) of the objective optical systems of the examples.

FIG. 17C, FIG. 18C, FIG. 19C, FIG. 20C, FIG. 21C, FIG. 22C, FIG. 23C, FIG. 24C, and FIG. 25C show a chromatic aberration of magnification (CC) of the objective optical systems of the examples.

FIG. 17D, FIG. 18D, FIG. 19D, FIG. 20D, FIG. 21D, FIG. 22D, FIG. 23D, FIG. 24D, and FIG. 25D show a distortion (DT) of the objective optical systems of the examples.

FIG. 26A, FIG. 26B, FIG. 26C, and FIG. 26D are aberration diagrams of the objective optical system of the reference example. In the aberration diagrams of the reference example, FIG. 26A shows a spherical aberration (SA), FIG. 26B shows an astigmatism (AS), FIG. 26C shows a chromatic aberration of magnification (CC), and FIG. 26D shows a distortion (DT).

An objective optical system of an example 1 includes in order from an object side, a negative meniscus lens L1 having a convex surface directed toward the object side, a planoconvex positive lens L2, a biconvex positive lens L3, a negative meniscus lens L4 having a convex surface directed toward an image side, a planoconcave negative lens L5, and a biconvex positive lens L6.

The biconvex positive lens L3 and the negative meniscus lens L4 are cemented. The planoconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 2 includes in order from an object side, a negative meniscus lens L1 having a convex surface directed toward the object side, a planoconvex positive lens L2, a biconvex positive lens L3, a negative meniscus lens L4 having a convex surface directed toward an image side, a biconcave negative lens L5, and a biconvex positive lens L6.

The biconvex positive lens L3 and the negative meniscus lens L4 are cemented. The biconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 3 includes in order from an object side, a negative meniscus lens L1 having a convex surface directed toward the object side, a planoconvex positive lens L2, a biconvex positive lens L3, a negative meniscus lens L4 having a convex surface directed toward an image side, a biconcave negative lens L5, and a biconvex positive lens L6.

The biconvex positive lens L3 and the negative meniscus lens L4 are cemented. The biconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 4 includes in order from an object side, a negative meniscus lens L1 having a convex surface directed toward the object side, a planoconvex positive lens L2, a biconcave negative lens L3, a biconvex positive lens L4, a negative meniscus lens L5 having a convex surface directed toward the object side, and a biconvex positive lens L6.

The biconcave negative lens L3 and the biconvex positive lens L4 are cemented. The negative meniscus lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 5 includes in order from an object side, a negative meniscus lens L1 having a convex surface directed toward the object side, a planoconvex positive lens L2, a biconcave negative lens L3, a biconvex positive lens L4, a negative meniscus lens L5 having a convex surface directed toward the object side, a positive meniscus lens L6 having a convex surface directed toward the object side, and a biconvex positive lens L7.

The biconcave negative lens L3 and the biconvex positive lens L4 are cemented. The negative meniscus lens L5, the positive meniscus lens L6, and the biconvex positive lens L7 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 6 includes in order from an object side, a negative meniscus lens L1 having a convex surface directed toward the object side, a planoconvex positive lens L2, a biconvex positive lens L3, a negative meniscus lens L4 having a convex surface directed toward an image side, a biconcave negative lens L5, and a biconvex positive lens L6.

The biconvex positive lens L3 and the negative meniscus lens L4 are cemented. The biconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 7 includes in order from an object side, a negative meniscus lens L1 having a convex surface directed toward the object side, a planoconvex positive lens L2, a biconvex positive lens L3, a negative meniscus lens L4 having a convex surface directed toward an image side, a negative meniscus lens L5 having a convex surface directed toward the object side, and a biconvex positive lens L6.

The biconvex positive lens L3 and the negative meniscus lens L4 are cemented. The negative meniscus lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 8 includes in order from an object side, a negative meniscus lens L1 having a convex surface directed toward the object side, a planoconvex positive lens L2, a biconvex positive lens L3, a negative meniscus lens L4 having a convex surface directed toward an image side, a biconcave negative lens L5, and a biconvex positive lens L6.

The biconvex positive lens L3 and the negative meniscus lens L4 are cemented. The biconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

An objective optical system of an example 9 includes in order from an object side, a negative meniscus lens L1 having a convex surface directed toward the object side, a planoconvex positive lens L2, a biconvex positive lens L3, a negative meniscus lens L4 having a convex surface directed toward an image side, a planoconcave negative lens L5, and a biconvex positive lens L6.

The biconvex positive lens L3 and the negative meniscus lens L4 are cemented. The planoconcave negative lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

An aspherical surface is provided to a total of three surfaces, which are both surfaces of the negative meniscus lens L1 and an image-side surface of the planoconvex positive lens L2.

The objective optical system of the reference example includes in order from an object side, a biconcave negative lens L1, a planoconvex positive lens L2, a biconvex positive lens L3, a negative meniscus lens L4 having a convex surface directed toward an image side, a negative meniscus lens L5 having a convex surface directed toward the object side, and a biconvex positive lens L6.

The biconvex positive lens L3 and the negative meniscus lens L4 are cemented. The negative meniscus lens L5 and the biconvex positive lens L6 are cemented.

A plane parallel plate C1 is disposed on the object side of the negative meniscus lens L1. A prism P is disposed on the object side of the planoconvex positive lens L2. The prism P is cemented to the planoconvex positive lens L2.

In the objective optical systems of the examples and the objective optical system of the reference example, the plane parallel plate C1 is used as a cover glass. It is possible to use sapphire for the plane parallel plate C1. Moreover, the plane parallel plate C1 may be imparted a refractive power. By making such arrangement, it is possible to use the plane parallel plate C1 as an auxiliary lens. For imparting a refractive power to the plane parallel plate C1, at least one optical surface is to be changed from a flat surface to a spherical surface.

In the objective optical system of each example and the objective optical system of the reference example, the planoconvex positive lens L2 and the prism P are cemented. However, the planoconvex positive lens L2 and the prism P may be separated apart. Moreover, a flat surface of the object side of the planoconvex positive lens may be made a spherical surface or an aspherical surface. The planoconvex lens L2 may be a cemented lens.

In the objective optical system of each example and the objective optical system of the reference example, it is possible to use the prism P as a direct vision prism, an oblique-viewing prism, or a side-viewing prism. In the lens cross-sectional views, the prism P being drawn to be unfolded, only an object-side surface and an image-side surface are shown. In a case in which the prism P is an oblique-viewing prism or a side-viewing prism, in the real prim, there is at least one reflecting surface between the object-side surface and the image-side surface.

Figure 36:
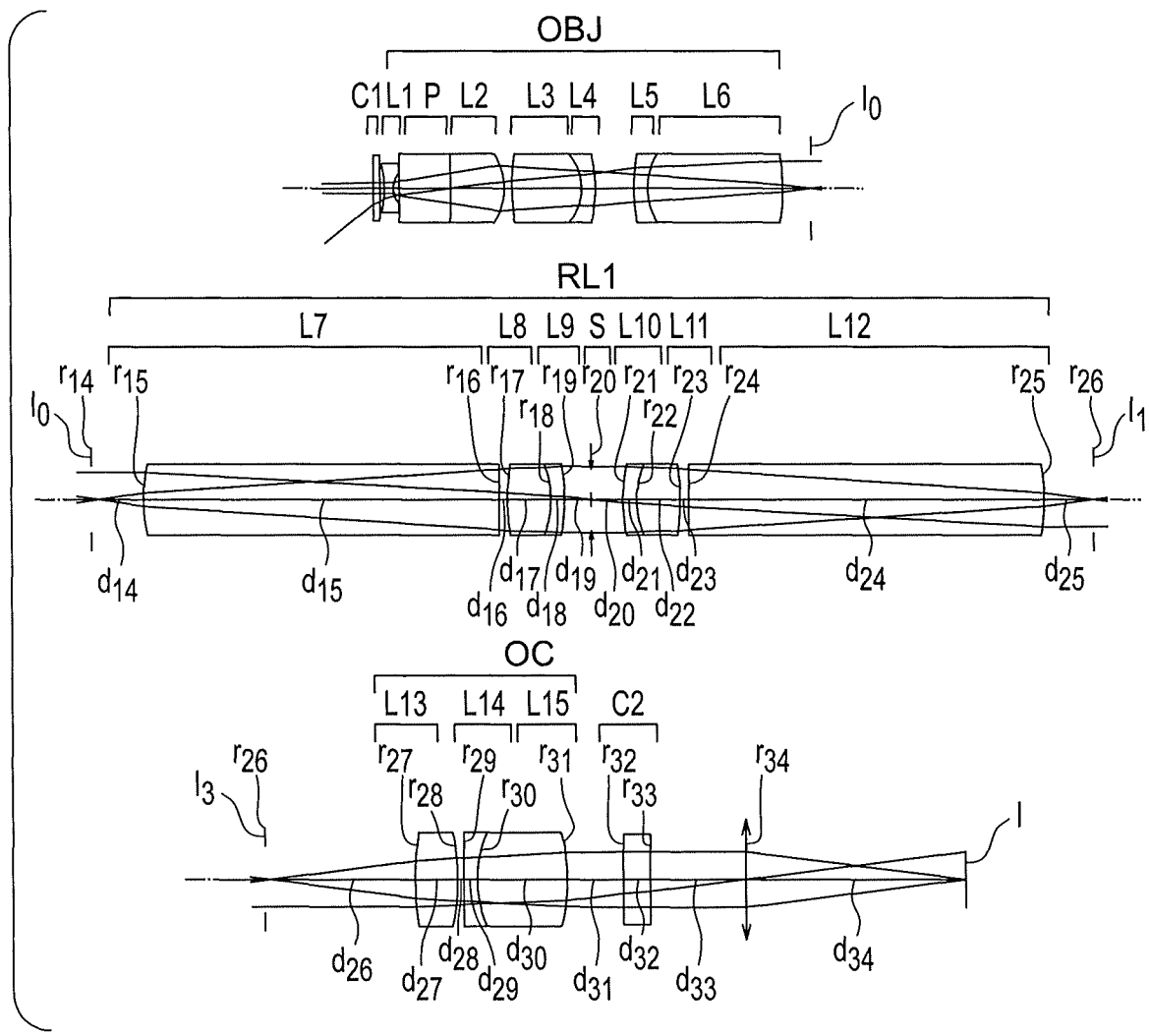
FIG. 36 is a lens cross-sectional view of an optical system for rigid endoscope of a reference example.
Figures 37A, 37B, 37C, 37D:
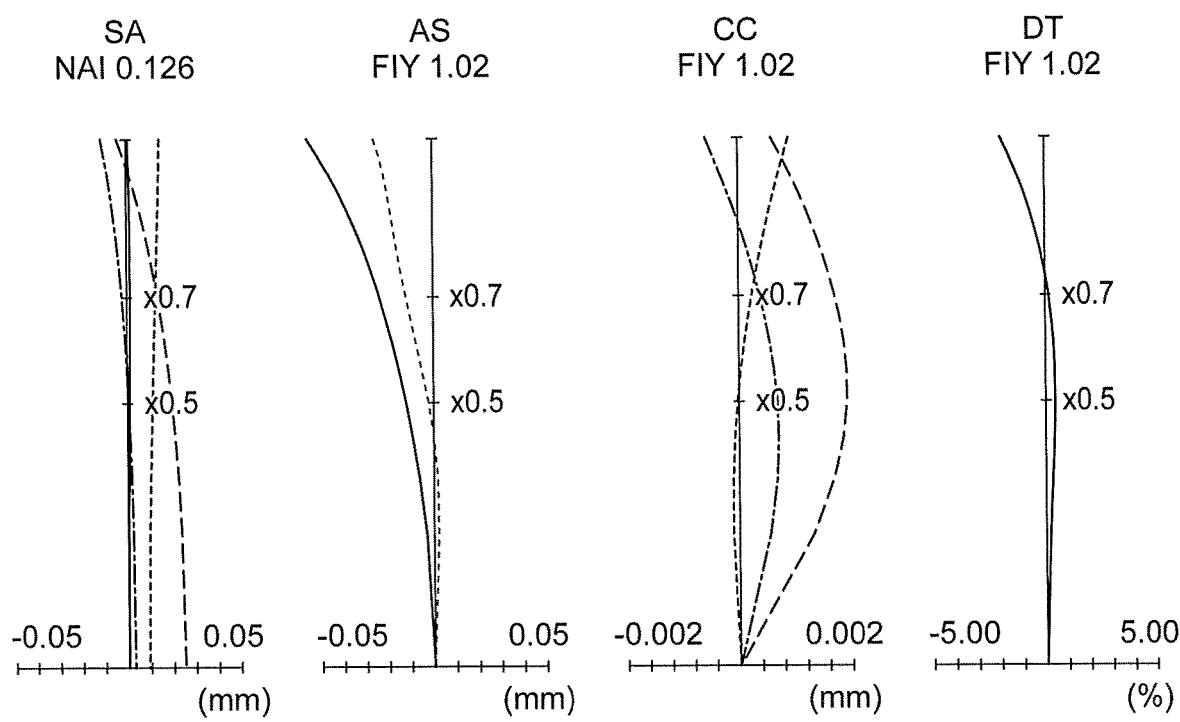
FIG. 37A, FIG. 37B, FIG. 37C, and FIG. 37D are aberration diagrams of the optical system for rigid endoscope of the example 1.
Figure 47:
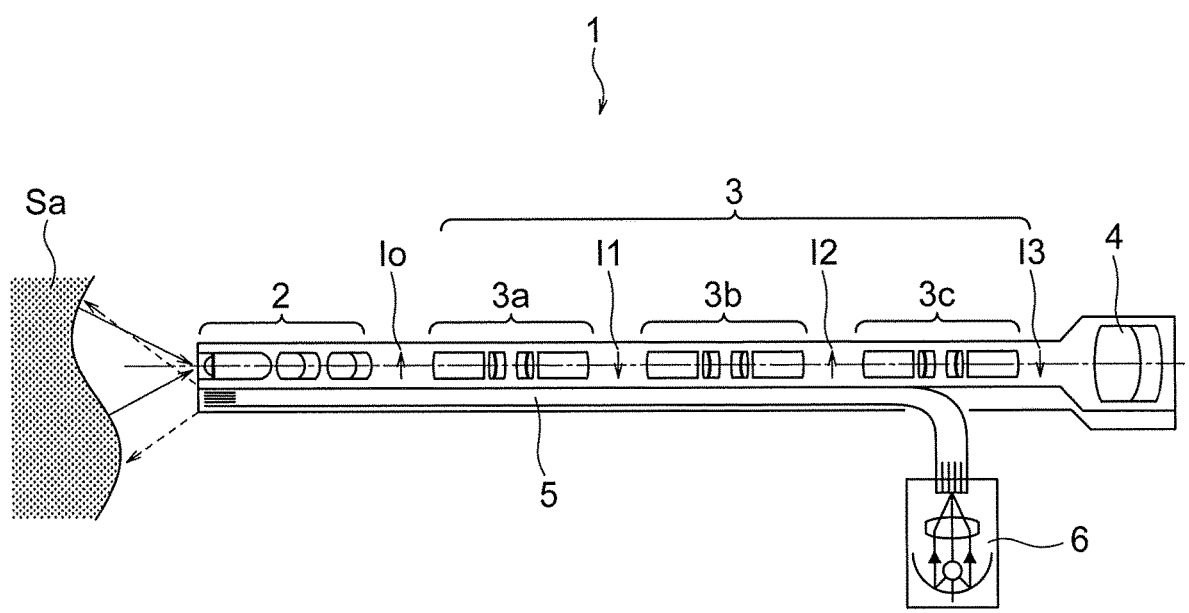
FIG. 47 is a schematic block diagram of a rigid endoscope.

Examples of the optical system for rigid endoscope will be described below. FIG. 27, FIG. 28, FIG. 29, FIG. 30, FIG. 31, FIG. 32, FIG. 33, FIG. 34, and FIG. 35 are lens cross-sectional views of the optical systems for rigid endoscope of the examples. FIG. 36 is a lens cross-sectional view of an optical system for rigid endoscope of a reference example.

In the lens cross-sectional views of the examples and the lens cross-sectional view of the reference example, an axial marginal light ray and a principal light ray of the maximum image height are shown.

Aberration diagrams of the optical system for rigid endoscope of each example will be described below.

FIG. 37A, FIG. 38A, FIG. 39A, FIG. 40A, FIG. 41A, FIG. 42A, FIG. 43A, FIG. 44A, and FIG. 45A show a spherical aberration (SA) of the optical systems for rigid endoscope of the respective examples.

FIG. 37B, FIG. 38B, FIG. 39B, FIG. 40B, FIG. 41B, FIG. 42B, FIG. 43B, FIG. 44B, and FIG. 45B show an astigmatism (AS) of the optical systems for rigid endoscope of the respective examples.

FIG. 37C, FIG. 38C, FIG. 39C, FIG. 40C, FIG. 41C, FIG. 42C, FIG. 43C, FIG. 44C, and FIG. 45C show a chromatic aberration of magnification (CC) of the optical systems for rigid endoscope of the respective examples.

FIG. 37D, FIG. 38D, FIG. 39D, FIG. 40D, FIG. 41D, FIG. 42D, FIG. 43D, FIG. 44D, and FIG. 45D show a distortion (DT) of the optical systems for rigid endoscope of the respective examples.

FIG. 46A, FIG. 46B, FIG. 46C, and FIG. 46D are aberration diagrams of the optical system for rigid endoscope of the reference example. In the aberration diagrams of the reference example, FIG. 46A shows a spherical aberration (SA), FIG. 46B shows an astigmatism (AS), FIG. 46C shows a chromatic aberration of magnification (CC), and FIG. 46D shows a distortion (DT).

The optical system for rigid endoscope of each example and the optical system for rigid endoscope of the reference examples include an objective optical system OBJ, an image relay unit, and an eyepiece optical system OC.

In the optical system for rigid endoscope of each example and the optical system for rigid endoscope of the reference example, a primary image Io is formed by the objective optical system OBJ. The primary image Io is relayed to a first relay optical system RL1. Accordingly, a first relay image I1 is formed.

In the optical system for rigid endoscope of each example, the image relay unit includes three relay optical systems. The first relay image I1 is relayed by a second relay optical system RL2. Accordingly, a second relay image I2 is formed. The second relay image I2 is relayed by a third relay optical system RL3. Accordingly, a third relay image I3 is formed. It is possible to observe the third relay image I3 by the eyepiece optical system OC.

In the optical system for rigid endoscope of the reference example, the image relay unit includes one relay optical system. A first relay image I1 is observed by the eyepiece optical system OC.

The optical system for rigid endoscope of each example and the optical system for rigid endoscope of the reference example are optical systems in which a relay image is observed by the eyepiece optical system OC. Since a real image is not formed independently by the optical system for rigid endoscope, it is not possible to indicate an appearance of aberration. For such reason, an ideal lens is disposed at a pupil position of the eyepiece optical system OC, and a final image I is formed. Aberrations at the final image I are indicated in the aberration diagrams. The pupil position of the eyepiece optical system OC is indicated by a two-way arrow in the lens cross-sectional views.

An image forming magnification by the eyepiece optical system OC and the ideal lens is −1 times. A value of an image height in the aberration diagrams is a value when a height of a primary image Io is 1. The distortion of the eyepiece optical system OC being approximately 2%, the image height at the final image is 1.02.

An optical system for rigid endoscope of an example 1 includes in order from an object side, an objective optical system OBJ, an image relay unit, and an eyepiece optical system OC. The objective optical system of the example 1 is used for the objective optical system OBJ. Therefore, description of a specific arrangement (such as shapes of lenses, refractive power, and the number of aspherical surfaces) of the objective optical system OBJ is omitted here. Similar is a case for the other examples and the reference example.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a positive meniscus lens L9 having a convex surface directed toward an image side, a negative meniscus lens L10 having a convex surface directed toward the image side, a negative meniscus lens L11 having a convex surface directed toward the object side, a positive meniscus lens L12 having a convex surface directed toward the object side, a biconvex positive lens L13, and a planoconvex positive lens L14 of which an image-side surface is a convex surface.

The biconvex positive lens L8, the positive meniscus lens L9, and the negative meniscus lens L10 are cemented. The negative meniscus lens L11, the positive meniscus lens L12, and the biconvex positive lens L13 are cemented.

The second relay optical system RL2 includes a planoconvex positive lens L15 of which an object-side surface is a convex surface, a biconvex positive lens L16, a positive meniscus lens L17 having a convex surface directed toward the image side, a negative meniscus lens L18 having a convex surface directed toward the image side, a negative meniscus lens L19 having a convex surface directed toward the object side, a positive meniscus lens L20 having a convex surface directed toward the object side, a biconvex positive lens L21, and a planoconvex positive lens L22 of which an image-side surface is a convex surface.

The biconvex positive lens L16, the positive meniscus lens L17, and the negative meniscus lens L18 are cemented. The negative meniscus lens L19, the positive meniscus lens L20, and the biconvex positive lens L21 are cemented.

The third relay optical system RL3 includes a planoconvex positive lens L23 of which an object-side surface is a convex surface, a biconvex positive lens L24, a positive meniscus lens L25 having a convex surface directed toward the image side, a negative meniscus lens L26 having a convex surface directed toward the image side, a negative meniscus lens L27 having a convex surface directed toward the object side, a positive meniscus lens L28 having a convex surface directed toward the object side, a biconvex positive lens L29, and a planoconvex positive lens L30 of which an image-side surface is a convex surface.

The biconvex positive lens L24, the positive meniscus lens L25, and the negative meniscus lens L26 are cemented. The negative meniscus lens L27, the positive meniscus lens L28, and the biconvex positive lens L29 are cemented.

A stop S is disposed between the negative meniscus lens L26 and the negative meniscus lens L27.

The eyepiece optical system OC includes a biconvex positive lens L31, a planoconcave negative lens L32, and a biconvex positive lens L33. The planoconcave negative lens L32 and the biconvex positive lens L33 are cemented. A plane parallel plate C2 is disposed on the image side of the eyepiece optical system OC.

An aspherical surface is provided to a total of six surfaces, which are an object-side surface of the negative meniscus lens L10, an image-side surface of the negative meniscus lens L11, an object-side surface of the negative meniscus lens L18, an image-side surface of the negative meniscus lens L19, an object-side surface of the negative meniscus lens L26, and an image-side surface of the negative meniscus lens L27.

An optical system for rigid endoscope of an example 2 includes an objective optical system OBJ, an image relay unit, and an eyepiece optical system OC. The objective optical system of the example 2 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a positive meniscus lens L9 having a convex surface directed toward an image side, a negative meniscus lens L10 having a convex surface directed toward the image side, a negative meniscus lens L11 having a convex surface directed toward the object side, a positive meniscus lens L12 having a convex surface directed toward the object side, a biconvex positive lens L13, and a planoconvex positive lens L14 of which an image-side surface is a convex surface.

The biconvex positive lens L8, the positive meniscus lens L9, and the negative meniscus lens L10 are cemented. The negative meniscus lens L11, the positive meniscus lens L12, and the biconvex positive lens L13 are cemented.

The second relay optical system RL2 includes a planoconvex positive lens L15 of which an object-side surface is a convex surface, a biconvex positive lens L16, a positive meniscus lens L17 having a convex surface directed toward the image side, a negative meniscus lens L18 having a convex surface directed toward the image side, a negative meniscus lens L19 having a convex surface directed toward the object side, a positive meniscus lens L20 having a convex surface directed toward the object side, a biconvex positive lens L21, and a planoconvex positive lens L22 of which an image-side surface is a convex surface.

The biconvex positive lens L16, the positive meniscus lens L17, and the negative meniscus lens L18 are cemented. The negative meniscus lens L19, the positive meniscus lens L20, and the biconvex positive lens L21 are cemented.

The third relay optical system RL3 includes a planoconvex positive lens L23 of which an object-side surface is a convex surface, a biconvex positive lens L24, a positive meniscus lens L25 having a convex surface directed toward the image side, a negative meniscus lens L26 having a convex surface directed toward the image side, a negative meniscus lens L27 having a convex surface directed toward the object side, a positive meniscus lens L28 having a convex surface directed toward the object side, a biconvex positive lens L29, and a planoconvex positive lens L30 of which an image-side surface is a convex surface.

The biconvex positive lens L24, the positive meniscus lens L25, and the negative meniscus lens L26 are cemented. The negative meniscus lens L27, the positive meniscus lens L28, and the biconvex positive lens L29 are cemented.

A stop S is disposed between the negative meniscus lens L26 and the negative meniscus lens L27.

The eyepiece optical system OC includes a biconvex positive lens L31, a negative meniscus lens L32 having a convex surface directed toward the object side, and a biconvex positive lens L33. The negative meniscus lens L32 and the biconvex positive lens L33 are cemented. A plane parallel plate C2 is disposed on the image side of the eyepiece optical system OC.

An aspherical surface is provided to a total of six surfaces, which are an object-side surface of the negative meniscus lens L10, an image-side surface of the negative meniscus lens L11, an object-side surface of the negative meniscus lens L18, an image-side surface of the negative meniscus lens L19, an object-side surface of the negative meniscus lens L26, and an image-side surface of the negative meniscus lens L27.

An optical system for rigid endoscope of an example 3 includes in order from an object side, an objective optical system OBJ, an image relay unit, and an eyepiece optical system OC. The objective optical system of the example 3 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a positive meniscus lens L9 having a convex surface directed toward an image side, a negative meniscus lens L10 having a convex surface directed toward the image side, a negative meniscus lens L11 having a convex surface directed toward the object side, a positive meniscus lens L12 having a convex surface directed toward the object side, a biconvex positive lens L13, and a planoconvex positive lens L14 of which an image-side surface is a convex surface.

The biconvex positive lens L8, the positive meniscus lens L9, and the negative meniscus lens L10 are cemented. The negative meniscus lens L11, the positive meniscus lens L12, and the biconvex positive lens L13 are cemented.

The second relay optical system RL2 includes a planoconvex positive lens L15 of which an object-side surface is a convex surface, a biconvex positive lens L16, a positive meniscus lens L17 having a convex surface directed toward the image side, a negative meniscus lens L18 having a convex surface directed toward the image side, a negative meniscus lens L19 having a convex surface directed toward the object side, a positive meniscus lens L20 having a convex surface directed toward the object side, a biconvex positive lens L21, and a planoconvex positive lens L22 of which an image-side surface is a convex surface.

The biconvex positive lens L16, the positive meniscus lens L17, and the negative meniscus lens L18 are cemented. The negative meniscus lens L19, the positive meniscus lens L20, and the biconvex positive lens L21 are cemented.

The third relay optical system RL3 includes a planoconvex positive lens L23 of which an object-side surface is a convex surface, a biconvex positive lens L24, a positive meniscus lens L25 having a convex surface directed toward the image side, a negative meniscus lens L26 having a convex surface directed toward the image side, a negative meniscus lens L27 having a convex surface directed toward the object side, a positive meniscus lens L28 having a convex surface directed toward the object side, a biconvex positive lens L29, and a planoconvex positive lens L30 of which an image-side surface is a convex surface.

The biconvex positive lens L24, the positive meniscus lens L25, and the negative meniscus lens L26 are cemented. The negative meniscus lens L27, the positive meniscus lens L28, and the biconvex positive lens L29 are cemented.

The eyepiece optical system OC includes a biconvex positive lens L31, a negative meniscus lens L32 having a convex surface directed toward the object side, a positive meniscus lens L33 having a convex surface directed toward the object side, and a biconvex positive lens L34. The negative meniscus lens L32, the positive meniscus lens L33, and the biconvex positive lens L34 are cemented. A plane parallel plate C2 is disposed on the image side of the eyepiece optical system OC.

An aspherical surface is provided to a total of six surfaces, which are an object-side surface of the negative meniscus lens L10, an image-side surface of the negative meniscus lens L11, an object-side surface of the negative meniscus lens L18, an image-side surface of the negative meniscus lens L19, an object-side surface of the negative meniscus lens L26, and an image-side surface of the negative meniscus lens L27.

An optical system for rigid endoscope of an example 4 includes in order from an object side, an objective optical system OBJ, an image relay unit, and an eyepiece optical system OC. The objective optical system of the example 4 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a negative meniscus lens L9 having a convex surface directed toward an image side, a diffractive optical element DOE, a negative meniscus lens L10 having a convex surface directed toward the object side, a biconvex positive lens L11, and a planoconvex positive lens L12 of which an image-side surface is a convex surface.

The biconvex positive lens L8 and the negative meniscus lens L9 are cemented. The negative meniscus lens L10 and the biconvex positive lens L11 are cemented. The diffractive optical element DOE includes two plane parallel plates. An optical surface of one of the plane parallel plates is provided with a diffractive surface.

The second relay optical system RL2 includes a planoconvex positive lens L13 of which an object side is a convex surface, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18 of which an image-side surface is a convex surface.

The biconvex positive lens L14 and the negative meniscus lens L15 are cemented. The negative meniscus lens L16 and the biconvex positive lens L17 are cemented.

The third relay optical system RL3 includes a planoconvex positive lens L19 of which an object-side surface is a convex surface, a biconvex positive lens L20, a negative meniscus lens L21 having a convex surface directed toward the image side, a negative meniscus lens L22 having a convex surface directed toward the object side, a biconvex positive lens L23, and a planoconvex positive lens L24 of which an image-side surface is a convex surface.

The biconvex positive lens L20 and the negative meniscus lens L21 are cemented. The negative meniscus lens L22 and the biconvex positive lens L23 are cemented.

A stop S is disposed between the negative meniscus lens L21 and the negative meniscus lens L22.

The eyepiece optical system OC includes a biconvex positive lens L25, a negative meniscus lens L26 having a convex surface directed toward the object side, and a biconvex positive lens L27. The negative meniscus lens L26 and the biconvex positive lens L27 are cemented. A plane parallel plate C2 is disposed on the image side of the eyepiece optical system OC.

An optical system for rigid endoscope of an example 5 includes in order from an object side, an objective optical system OBJ, an image relay unit, and an eyepiece optical system OC. The objective optical system of the example 5 is used for the objective optical system OBJ.

The image relay unit includes a first relay optical system RL1, a second relay optical system RL2, and a third relay optical system RL3.

The first relay optical system RL1 includes a planoconvex positive lens L8 of which an object-side surface is a convex surface, a biconvex positive lens L9, a negative meniscus lens L10 having a convex surface directed toward an image side, a diffractive optical element DOE, a negative meniscus lens L11 having a convex surface directed toward the object side, a biconvex positive lens L12, and a planoconvex positive lens L13 of which an image-side surface is a convex surface.

The biconvex positive lens L9 and the negative meniscus lens L10 are cemented. The negative meniscus lens L11 and the biconvex positive lens L12 are cemented. The diffractive optical element DOE includes two plane parallel plates. An optical surface of one of the plane parallel plates is provided with a diffractive surface.

The second relay optical system RL2 includes a planoconvex positive lens L14 of which an object-side surface is a convex surface, a biconvex positive lens L15, a negative meniscus lens L16 having a convex surface directed toward the image side, a negative meniscus lens L17 having a convex surface directed toward the object side, a biconvex positive lens L18, and a planoconvex positive lens L19 of which an image-side surface is a convex surface.

The biconvex positive lens L15 and the negative meniscus lens L16 are cemented. The negative meniscus lens L17 and the biconvex positive lens L18 are cemented.

The third relay optical system RL3 includes a planoconvex positive lens L20 of which an object-side surface is a convex surface, a biconvex positive lens L21, a negative meniscus lens L22 having a convex surface directed toward the image side, a negative meniscus lens L23 having a convex surface directed toward the object side, a biconvex positive lens L24, and a planoconvex positive lens L25 of which an image-side surface is a convex surface.

The biconvex positive lens L21 and the negative meniscus lens L22 are cemented. The negative meniscus lens L23 and the biconvex positive lens L24 are cemented.

A stop S is disposed between the negative meniscus lens L22 and the negative meniscus lens L23.

The eyepiece optical system OC includes a biconvex positive lens L26, a negative meniscus lens L27 having a convex surface directed toward the object side, and a biconvex positive lens L28. The negative meniscus lens L27 and the biconvex positive lens L28 are cemented. A plane parallel plate C2 is disposed on the image side of the eyepiece optical system OC.

An optical system for rigid endoscope of an example 6 includes in order from an object side, an objective optical system OBJ, an image relay unit, and an eyepiece optical system OC. The objective optical system of the example 6 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a negative meniscus lens L9 having a convex surface directed toward an image side, a negative meniscus lens L10 having a convex surface directed toward the object side, a biconvex positive lens L11, and a planoconvex positive lens L12 of which an image-side surface is a convex surface.

The biconvex positive lens L8 and the negative meniscus lens L9 are cemented. The negative meniscus lens L10 and the biconvex positive lens L11 are cemented.

The second relay optical system RL2 includes a planoconvex positive lens L13 of which an object-side surface is a convex surface, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18 of which an image-side surface is a convex surface.

The biconvex positive lens L14 and the negative meniscus lens L15 are cemented. The negative meniscus lens L16 and the biconvex positive lens L17 are cemented.

The third relay optical system RL3 includes a planoconvex positive lens L19 of which an object-side surface is a convex surface, a biconvex positive lens L20, a negative meniscus lens L21 having a convex surface directed toward the image side, a negative meniscus lens L22 having a convex surface directed toward the object side, a biconvex positive lens L23, and a planoconvex positive lens L24 of which an image-side surface is a convex surface.

The biconvex positive lens L20 and the negative meniscus lens L21 are cemented. The negative meniscus lens L22 and the biconvex positive lens L23 are cemented.

A stop S is disposed between the negative meniscus lens L21 and the negative meniscus lens L22.

The eyepiece optical system OC includes a negative meniscus lens L25 having a convex surface directed toward the object side, a positive meniscus lens L26 having a convex surface directed toward the object side, and a biconvex positive lens L27. The negative meniscus lens L25, the positive meniscus lens L26, and the biconvex positive lens L27 are cemented. A plane parallel plate C2 is disposed on the image side of the eyepiece optical system OC.

An optical system for rigid endoscope of an example 7 includes in order from an object side, an objective optical system OBJ, an image relay unit, and an eyepiece optical system OC. The objective optical system of the example 7 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a negative meniscus lens L9 having a convex surface directed toward an image side, a negative meniscus lens L10 having a convex surface directed toward the object side, a biconvex positive lens L11, and a planoconvex positive lens L12 of which an image-side surface is a convex surface.

The biconvex positive lens L8 and the negative meniscus lens L9 are cemented. The negative meniscus lens L10 and the biconvex positive lens L11 are cemented.

The second relay optical system RL2 includes a planoconvex positive lens L13 of which an object-side surface is a convex surface, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18 of which an image-side surface is a convex surface.

The biconvex positive lens L14 and the negative meniscus lens L15 are cemented. The negative meniscus lens L16 and the biconvex positive lens L17 are cemented.

The third relay optical system RL3 includes a planoconvex positive lens L19 of which an object-side surface is a convex surface, a biconvex positive lens L20, a negative meniscus lens L21 having a convex surface directed toward the image side, a negative meniscus lens L22 having a convex surface directed toward the object side, a biconvex positive lens L23, and a planoconvex positive lens L24 of which an image-side surface is a convex surface.

The biconvex positive lens L20 and the negative meniscus lens L21 are cemented. The negative meniscus lens L22 and the biconvex positive lens L23 are cemented.

A stop S is disposed between the negative meniscus lens L21 and the negative meniscus lens L22.

An eyepiece optical system OC includes a biconvex positive lens L25, a planoconcave negative lens L26, and a biconvex positive lens L27. The planoconcave negative lens L26 and the biconvex positive lens L27 are cemented. A plane parallel plate C2 is disposed on the image side of the eyepiece optical system OC.

An optical system for rigid endoscope of an example 8 includes in order from an object side, an objective optical system OBJ, an image relay unit, and an eyepiece optical system OC. The objective optical system of the example 8 is used for the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a negative meniscus lens L9 having a convex surface directed toward an image side, a negative meniscus lens L10 having a convex surface directed toward the object side, a biconvex positive lens L11, and a planoconvex positive lens L12 of which an image-side surface is a convex surface.

The biconvex positive lens L8 and the negative meniscus lens L9 are cemented. The negative meniscus lens L10 and the biconvex positive lens L11 are cemented.

The second relay optical system RL2 includes a planoconvex positive lens L13 of which an object-side surface is a convex surface, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18 of which an image-side surface is a convex surface.

The biconvex positive lens L14 and the negative meniscus lens L15 are cemented. The negative meniscus lens L16 and the biconvex positive lens L17 are cemented.

The third relay optical system RL3 includes a planoconvex positive lens L19 of which an object-side surface is a convex surface, a biconvex positive lens L20, a negative meniscus lens L21 having a convex surface directed toward the image side, a negative meniscus lens L22 having a convex surface directed toward the object side, a biconvex positive lens L23, and a planoconvex positive lens L24 of which an image-side surface is a convex surface.

The biconvex positive lens L20 and the negative meniscus lens L21 are cemented. The negative meniscus lens L22 and the biconvex positive lens L23 are cemented.

A stop S is disposed between the negative meniscus lens L21 and the negative meniscus lens L22.

The eyepiece optical system OC includes a biconvex positive lens L25, a planoconcave negative lens L26, and a biconvex positive lens L27. The planoconcave negative lens L26 and the biconvex positive lens L27 are cemented. A plane parallel plate C2 is disposed on the image side of the eyepiece optical system OC.

An optical system for rigid endoscope of an example 9 includes in order from an object side, an objective optical system OBJ, an image relay unit, and an eyepiece optical system OC. The objective optical system of the example 9 is used as the objective optical system OBJ.

The image relay unit includes a first relay optical system RL1, a second relay optical system RL2, and a third relay optical system RL3.

The first relay optical system RL1 includes a planoconvex positive lens L7 of which an object-side surface is a convex surface, a biconvex positive lens L8, a negative meniscus lens L9 having a convex surface directed toward an image side, a negative meniscus lens L10 having a convex surface directed toward the object side, a biconvex positive lens L11, and a planoconvex positive lens L12 of which an image-side surface is a convex surface.

The biconvex positive lens L8 and the negative meniscus lens L9 are cemented. The negative meniscus lens L10 and the biconvex positive lens L11 are cemented.

The second relay optical system RL2 includes a planoconvex positive lens L13 of which an object-side surface is a convex surface, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18 of which an image-side surface is a convex surface.

The biconvex positive lens L14 and the negative meniscus lens L15 are cemented. The negative meniscus lens L16 and the biconvex positive lens L17 are cemented.

The third relay optical system RL3 includes a planoconvex positive lens L19 of which an object-side surface is a convex surface, a biconvex positive lens L20, a negative meniscus lens L21 having a convex surface directed toward the image side, a negative meniscus lens L22 having a convex surface directed toward the object side, a biconvex positive lens L23, and a planoconvex positive lens L24 of which an image-side surface is a convex surface.

The biconvex positive lens L20 and the negative meniscus lens L21 are cemented. The negative meniscus lens L22 and the biconvex positive lens L23 are cemented.

A stop S is disposed between the negative meniscus lens L21 and the negative meniscus lens L22.

The eyepiece optical system OC includes a biconvex positive lens L25, a planoconcave negative lens L26, and a biconvex positive lens L27. The planoconcave negative lens L26 and the biconvex positive lens L27 are cemented. A plane parallel plate C2 is disposed on the image side of the eyepiece optical system OC.

The optical system for rigid endoscope of the reference example includes in order from an object side, an objective optical system OBJ, an image relay unit, and an eyepiece optical system OC. The objective optical system of the reference example is the objective optical system OBJ.

The image relay unit includes a first relay optical system RL1.

The first relay optical system RL1 includes a planoconvex positive lens L7 of which an object-side surface is a convex surface, a biconvex positive lens L8, a negative meniscus lens L9 having a convex surface directed toward an image side, a negative meniscus lens L10 having a convex surface directed toward the object side, a biconvex positive lens L11, and a planoconvex positive lens L12 of which an image-side surface is a convex surface.

A stop S is disposed between the negative meniscus lens L9 and the negative meniscus lens L10.

The biconvex positive lens L8 and the negative meniscus lens L9 are cemented. The negative meniscus lens L10 and the biconvex positive lens L11 are cemented.

The eyepiece optical system OC includes a biconvex positive lens L13, a planoconcave negative lens L14, and a biconvex positive lens L15. The planoconcave negative lens L14 and the biconvex positive lens L15 are cemented. A plane parallel plate C2 is disposed on the image side of the eyepiece optical system OC.

In the optical system for rigid endoscope of each example and the optical system for rigid endoscope of the reference example, the plane parallel plate C2 is used as a cover glass. It is possible to use sapphire for the plane parallel plate C2. Moreover, the plane parallel plate C2 may be imparted a refractive power. By making such arrangement, it is possible to use the plane parallel plate C2 as an auxiliary lens. For imparting a refractive power to the plane parallel plate C2, at least one surface is to be changed from a flat surface to a spherical surface.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, * denotes an aspherical surface, and # denotes a diffractive surface.

In Various data, OB denotes an object distance, FOV denotes an angle of view (2ω: unit °), NAI denotes an image-side numerical aperture of the objective lens, IH denotes the maximum height of the primary image Io, and IHtotal denotes the maximum image height of the final image I.

In Numerical data and Glass material data, a name of glass material is mentioned specifically in a column of GLA. However, C1, C2, Resin A, Resin B, and Resin C are not specific names of glass material. A glass material for which a specific name is mentioned is a glass material by Ohara Corporation.

In Glass material data, five numerical values mentioned on a right side of GLA are a wavelength for a d-line, a wavelength for a C-line, a wavelength for an F-line, a wavelength for a g-line, and a wavelength for an e-line. Each of the five numerical values mentioned on the right side of each glass material name is a refractive index for each wavelength.

Moreover, a shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . .

$$Z = (y^2/r) / \left[1 + \{1 - (1+k)(y/r)^2\}^{1/2}\right] + A_4 y^4 + A_6 y^6 + A_8 y^8 + A_{10} y^{10} + A_{12} y^{12} + \ldots$$

Moreover, a diffractive surface, based on high refractive index method, is indicated as an aspheric-surface shape of an equivalent ultrahigh index lens (refracting lens having an extremely high refractive index). The following relationship is established between a pitch d of a diffraction grating formed on the diffractive surface and the aspheric-surface shape of the ultrahigh index lens.

$$d = m\lambda / [(n-1)\{ch/(1-c^2(1+k)h^2)^{1/2} + 2A_2 h + 4A_4 h^3 + 6A_6 h^5 + 8A_8 h^7 + 10A_{10} h^9 + \}]$$

Since the ideal lens is treated as a thin lens, a thickness is zero. A position of disposing the ideal lens is indicated by a surface number in Surface data of a numerical example.

Example 1

| | | | Unit mm | | | |
|---|---|---|---|---|---|---|
| | | | Surface data | | | |
| Surface no. | r | d | GLA | nd | vd | ER |
| Object plane | ∞ | 16.8350 | | 1. | | |
| 1 | ∞ | 0.2357 | C1 | 1.76900 | 64.15 | 1.178U |
| 2 | ∞ | 0.0673 | | 1. | | 1.178U |
| 3* | 1.2172 | 0.3367 | L-LAH53_O | 1.80625 | 40.91 | 0.859U |
| 4* | 0.3121 | 0.5253 | | 1. | | 0.539U |
| 5 | ∞ | 1.7677 | S-LAH53_O | 1.80610 | 40.95 | 1.229U |
| 6 | ∞ | 3.6700 | L-LAH53_O | 1.80625 | 40.91 | 1.229U |
| 7* | −2.1882 | 0.2357 | | 1. | | 1.229U |
| 8 | 11.2774 | 1.1313 | S-FPL55_O | 1.43875 | 94.66 | 1.229U |
| 9 | −1.9199 | 0.4040 | S-TIL25_O | 1.58144 | 40.75 | 1.229U |
| 10 | −3.8468 | 0.3704 | | 1. | | 1.229U |
| 11 | ∞ | 1.3468 | S-TIH53_O | 1.84666 | 23.78 | 1.229U |
| 12 | 2.1448 | 4.2761 | S-FPL55_O | 1.43875 | 94.66 | 1.229U |
| 13 | −3.4761 | 1.7306 | | 1. | | 1.229U |
| 14 | ∞ | 1.6330 | | 1. | | 1.347U |
| 15 | 5.9222 | 10.7744 | S-BAL35_O | 1.58913 | 61.14 | 1.263U |
| 16 | ∞ | 0.7003 | | 1. | | 1.263U |
| 17 | 6.4246 | 1.6330 | S-FPL51_O | 1.49700 | 81.54 | 1.263U |
| 18 | −3.4761 | 0.1414 | Resin A | 1.60397 | 28.60 | 1.263U |
| 19* | −2.9175 | 1.3131 | L-LAH53_O | 1.80625 | 40.91 | 1.263U |
| 20 | −6.9037 | 0.5050 | | 1. | | 1.263U |
| 21 | 6.9037 | 1.3131 | L-LAH53_O | 1.80625 | 40.91 | 1.263U |
| 22* | 2.9175 | 0.1414 | Resin A | 1.60397 | 28.60 | 1.263U |
| 23 | 3.4761 | 1.6330 | S-FPL51_O | 1.49700 | 81.54 | 1.263U |
| 24 | −6.4246 | 0.7003 | | 1. | | 1.263U |
| 25 | ∞ | 10.7744 | S-BAL35_O | 1.58913 | 61.14 | 1.263U |
| 26 | −5.9222 | 1.6330 | | 1. | | 1.263U |
| 27 | ∞ | 1.6330 | | 1. | | 1.347U |
| 28 | 5.9222 | 10.7744 | S-BAL35_O | 1.58913 | 61.14 | 1.263U |
| 29 | ∞ | 0.7003 | | 1. | | 1.263U |
| 30 | 6.4246 | 1.6330 | S-FPL51_O | 1.49700 | 81.54 | 1.263U |
| 31 | −3.4761 | 0.1414 | Resin A | 1.60397 | 28.60 | 1.263U |
| 32* | −2.9175 | 1.3131 | L-LAH53_O | 1.80625 | 40.91 | 1.263U |
| 33 | −6.9037 | 0.5050 | | 1. | | 1.263U |
| 34 | 6.9037 | 1.3131 | L-LAH53_O | 1.80625 | 40.91 | 1.263U |
| 35* | 2.9175 | 0.1414 | Resin A | 1.60397 | 28.60 | 1.263U |
| 36 | 3.4761 | 1.6330 | S-FPL51_O | 1.49700 | 81.54 | 1.263U |
| 37 | −6.4246 | 0.7003 | | 1. | | 1.263U |
| 38 | ∞ | 10.7744 | S-BAL35_O | 1.58913 | 61.14 | 1.263U |
| 39 | −5.9222 | 1.6330 | | 1. | | 1.263U |
| 40 | ∞ | 1.6330 | | 1. | | 1.347U |
| 41 | 5.9222 | 10.7744 | S-BAL35_O | 1.58913 | 61.14 | 1.263U |
| 42 | ∞ | 0.7003 | | 1. | | 1.263U |
| 43 | 6.4246 | 1.6330 | S-FPL51_O | 1.49700 | 81.54 | 1.263U |
| 44 | −3.4761 | 0.1414 | Resin A | 1.60397 | 28.60 | 1.263U |
| 45* | −2.9175 | 1.3131 | L-LAH53_O | 1.80625 | 40.91 | 1.263U |
| 46 | −6.9037 | 0.2525 | | 1. | | 1.263U |
| 47 (Stop) | ∞ | 0.2525 | | 1. | | 1.133U |
| 48 | 6.9037 | 1.3131 | L-LAH53_O | 1.80625 | 40.91 | 1.263U |
| 49* | 2.9175 | 0.1414 | Resin A | 1.60397 | 28.60 | 1.263U |
| 50 | 3.4761 | 1.6330 | S-FPL51_O | 1.49700 | 81.54 | 1.263U |
| 51 | −6.4246 | 0.7003 | | 1. | | 1.263U |
| 52 | ∞ | 10.7744 | S-BAL35_O | 1.58913 | 61.14 | 1.263U |
| 53 | −5.9222 | 1.6330 | | 1. | | 1.263U |
| 54 | ∞ | 5.4983 | | 1. | | 1.684U |
| 55 | 11.4101 | 1.5825 | S-FPL51_O | 1.49700 | 81.54 | 1.684U |
| 56 | −7.8761 | 0.2357 | | 1. | | 1.684U |
| 57 | ∞ | 0.5051 | S-LAH60_O | 1.83400 | 37.16 | 1.684U |
| 58 | 4.4690 | 3.3670 | S-BAL35_O | 1.58913 | 61.14 | 1.684U |
| 59 | −6.8024 | 2.0875 | | 1. | | 1.684U |

-continued

| Unit mm | | | | | | |
|---|---|---|---|---|---|---|
| 60 | ∞ | 1.0101 | C2 | 1.76819 | 71.70 | 1.515U |
| 61 | ∞ | 3.5354 | | 1. | | 1.515U |
| 62 (Pupil) | ∞ | 8.1621 | | 1. | | 1.025 |
| Image plane | ∞ | 0. | | | | |

Aspherical surface data

3rd surface

K = −0.7490
AC2 = 0.0000E+00, AC4 = −2.4988E−01, AC6 = 7.7207E−02,
AC8 = 0.0000E+00, AC10 = 0.0000E+00
4th surface K = −0.8100
AC2 = 0.0000E+00, AC4 = −1.4912E−01, AC6 = −1.7424E+00,
AC8 = 0.0000E+00, AC10 = 0.0000E+00
7th surface K = −0.3490
AC2 = 0.0000E+00, AC4 = 5.4623E−03, AC6 = 0.0000E+00,
AC8 = 0.0000E+00, AC10 = 0.0000E+00
19th surface K = −0.2320
AC2 = 0.0000E+00, AC4 = −1.6581E−03, AC6 = 0.0000E+00,
AC8 = 0.0000E+00, AC10 = 0.0000E+00
22nd surface K = −0.2320
AC2 = 0.0000E+00, AC4 = 1.6581E−03, AC6 = 0.0000E+00,
AC8 = 0.0000E+00, AC10 = 0.0000E+00
32nd surface K = −0.2320
AC2 = 0.0000E+00, AC4 = −1.6581E−03, AC6 = 0.0000E+00,
AC8 = 0.0000E+00, AC10 = 0.0000E+00
35th surface K = −0.2320
AC2 = 0.0000E+00, AC4 = 1.6581E−03, AC6 = 0.0000E+00,
AC8 = 0.0000E+00, AC10 = 0.0000E+00
45th surface K = −0.2320
AC2 = 0.0000E+00, AC4 = −1.6581E−03, AC6 = 0.0000E+00,
AC8 = 0.0000E+00, AC10 = 0.0000E+00
49th surface K = −0.2320
AC2 = 0.0000E+00, AC4 = 1.6581E−03, AC6 = 0.0000E+00,
AC8 = 0.0000E+00, AC10 = 0.0000E+00

Various data

| | | |
|---|---|---|
| OB | | 16.8350 |
| FOV | | 88.7 |
| NAI | | 0.1257 |
| IH | | 1 |
| IHtotal | | 1.022 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53_O_3 | 1.806250 | 1.800394 | 1.820103 | 1.831320 | 1.810931 |
| Resin A | 1.603970 | 1.597970 | 1.619090 | 1.632280 | 1.608930 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-FPL55_O_1 | 1.438750 | 1.437328 | 1.441963 | 1.444438 | 1.439857 |
| S-LAH53_O_1 | 1.806098 | 1.800251 | 1.819937 | 1.831152 | 1.810773 |

-continued

| Unit mm | | | | | |
|---|---|---|---|---|---|
| S-LAH60_O_3 | 1.834000 | 1.827376 | 1.849819 | 1.862781 | 1.839323 |
| S-TIH53_O_3 | 1.846660 | 1.836488 | 1.872096 | 1.894189 | 1.855041 |
| S-TIL25_O_3 | 1.581439 | 1.577216 | 1.591486 | 1.599726 | 1.584822 |

| Ideal lens | |
|---|---|
| Displacement position | 62 (Pupil) |
| Focal length | 7.9694 |

Example 2

| Unit mm | | | | | |
|---|---|---|---|---|---|
| Surface data | | | | | |
| Surface no. | r | d | GLA | nd | vd | ER |
| Object plane | ∞ | 16.7487 | | 1. | | |
| 1 | ∞ | 0.2345 | C1 | 1.76900 | 64.15 | 1.172U |
| 2 | ∞ | 0.0670 | | 1. | | 1.172U |
| 3* | 1.1498 | 0.3072 | L-LAH53_O | 1.80625 | 40.91 | 0.854U |
| 4* | 0.3068 | 0.5299 | | 1. | | 0.536U |
| 5 | ∞ | 1.7586 | S-LAH53_O | 1.80610 | 40.92 | 1.223U |
| 6 | ∞ | 3.9649 | L-LAH53_O | 1.80625 | 40.91 | 1.223U |
| 7* | −2.2266 | 0.2843 | | 1. | | 1.223U |
| 8 | 14.4427 | 1.0042 | S-FPL55_O | 1.43875 | 94.66 | 1.223U |
| 9 | −1.9952 | 0.4278 | S-TIL25_O | 1.58144 | 40.75 | 1.223U |
| 10 | −3.9063 | 0.4677 | | 1. | | 1.223U |
| 11 | −39.7623 | 1.0781 | S-TIH53_O | 1.84666 | 23.78 | 1.223U |
| 12 | 2.5175 | 4.0417 | S-FPL55_O | 1.43875 | 94.66 | 1.223U |
| 13 | −3.6497 | 2.2937 | | 1. | | 1.223U |
| 14 | ∞ | 1.6581 | | 1. | | 1.340U |
| 15 | 5.9696 | 9.9822 | S-BAL35_O | 1.58913 | 61.14 | 1.256U |
| 16 | ∞ | 0.8374 | | 1. | | 1.256U |
| 17 | 7.0864 | 2.0098 | S-FPL51_O | 1.49700 | 81.54 | 1.256U |
| 18 | −3.2184 | 0.1005 | Resin B | 1.63387 | 23.38 | 1.256U |
| 19* | −2.9863 | 1.4739 | L-LAH53_O | 1.80625 | 40.91 | 1.256U |
| 20 | −6.5189 | 0.6030 | | 1. | | 1.256U |
| 21 | 6.5189 | 1.4739 | L-LAH53_O | 1.80625 | 40.91 | 1.256U |
| 22* | 2.9863 | 0.1005 | Resin B | 1.63387 | 23.38 | 1.256U |
| 23 | 3.2184 | 2.0098 | S-FPL51_O | 1.49700 | 81.54 | 1.256U |
| 24 | −7.0864 | 0.8374 | | 1. | | 1.256U |
| 25 | ∞ | 9.9822 | S-BAL35_O | 1.58913 | 61.14 | 1.256U |
| 26 | −5.9696 | 1.6581 | | 1. | | 1.256U |
| 27 | ∞ | 1.6581 | | 1. | | 1.340U |
| 28 | 5.9696 | 9.9822 | S-BAL35_O | 1.58913 | 61.14 | 1.256U |
| 29 | ∞ | 0.8374 | | 1. | | 1.256U |
| 30 | 7.0864 | 2.0098 | S-FPL51_O | 1.49700 | 81.54 | 1.256U |
| 31 | −3.2184 | 0.1005 | Resin B | 1.63387 | 23.38 | 1.256U |
| 32* | −2.9863 | 1.4739 | L-LAH53_O | 1.80625 | 40.91 | 1.256U |
| 33 | −6.5189 | 0.6030 | | 1. | | 1.256U |
| 34 | 6.5189 | 1.4739 | L-LAH53_O | 1.80625 | 40.91 | 1.256U |
| 35* | 2.9863 | 0.1005 | Resin B | 1.63387 | 23.38 | 1.256U |
| 36 | 3.2184 | 2.0098 | S-FPL51_O | 1.49700 | 81.54 | 1.256U |
| 37 | −7.0864 | 0.8374 | | 1. | | 1.256U |
| 38 | ∞ | 9.9822 | S-BAL35_O | 1.58913 | 61.14 | 1.256U |
| 39 | −5.9696 | 1.6581 | | 1. | | 1.256U |
| 40 | ∞ | 1.6581 | | 1. | | 1.340U |
| 41 | 5.9696 | 9.9822 | S-BAL35_O | 1.58913 | 61.14 | 1.256U |
| 42 | ∞ | 0.8374 | | 1. | | 1.256U |
| 43 | 7.0864 | 2.0098 | S-FPL51_O | 1.49700 | 81.54 | 1.256U |
| 44 | −3.2184 | 0.1005 | Resin B | 1.63387 | 23.38 | 1.256U |
| 45* | −2.9863 | 1.4739 | L-LAH53_O | 1.80625 | 40.91 | 1.256U |
| 46 | −6.5189 | 0.3015 | | 1. | | 1.256U |
| 47 (Stop) | ∞ | 0.3015 | | 1. | | 1.134U |
| 48 | 6.5189 | 1.4739 | L-LAH53_O | 1.80625 | 40.91 | 1.256U |
| 49* | 2.9863 | 0.1005 | Resin B | 1.63387 | 23.38 | 1.256U |
| 50 | 3.2184 | 2.0098 | S-FPL51_O | 1.49700 | 81.54 | 1.256U |
| 51 | −7.0864 | 0.8374 | | 1. | | 1.256U |
| 52 | ∞ | 9.9822 | S-BAL35_O | 1.58913 | 61.14 | 1.256U |
| 53 | −5.9696 | 1.6581 | | 1. | | 1.256U |
| 54 | ∞ | 5.4183 | | 1. | | 1.675U |
| 55 | 11.2707 | 1.3880 | S-FPL53_O | 1.43875 | 94.93 | 1.675U |

-continued

| | | | Unit mm | | | |
|---|---|---|---|---|---|---|
| 56 | −7.9999 | 0.7267 | | 1. | | 1.675U |
| 57 | 75.1156 | 0.4977 | S-LAH60_O | 1.83400 | 37.16 | 1.675U |
| 58 | 4.6099 | 2.9726 | S-BAL35_O | 1.58913 | 61.14 | 1.675U |
| 59 | −6.6676 | 1.7952 | | 1. | | 1.675U |
| 60 | ∞ | 1.0049 | C2 | 1.76819 | 71.70 | 1.507U |
| 61 | ∞ | 3.5172 | | 1. | | 1.507U |
| 62 (Pupil) | ∞ | 8.1168 | | 1. | | 1.020 |
| Image plane | ∞ | 0. | | | | |

Aspherical surface data

3rd surface

K = −1.0661
AC2 = 0.0000E+00, AC4 = −2.4766E−01, AC6 = 7.1750E−02,
AC8 = 0.0000E+00, AC10 = 0.0000E+00

4th surface

K = −1.0010
AC2 = 0.0000E+00, AC4 = 6.8696E−01, AC6 = −1.1963E+00,
AC8 = 0.0000E+00, AC10 = 0.0000E+00

7th surface

K = −0.3709
AC2 = 0.0000E+00, AC4 = 5.4465E−03, AC6 = 0.0000E+00,
AC8 = 0.0000E+00, AC10 = 0.0000E+00

19th surface

K = −0.2430
AC2 = 0.0000E+00, AC4 = −1.7267E−03, AC6 = 0.0000E+00,
AC8 = 0.0000E+00, AC10 = 0.0000E+00

22nd surface

K = −0.2430
AC2 = 0.0000E+00, AC4 = 1.7267E−03, AC6 = 0.0000E+00,
AC8 = 0.0000E+00, AC10 = 0.0000E+00

32nd surface

K = −0.2430
AC2 = 0.0000E+00, AC4 = −1.7267E−03, AC6 = 0.0000E+00,
AC8 = 0.0000E+00, AC10 = 0.0000E+00

35th surface

K = −0.2430
AC2 = 0.0000E+00, AC4 = 1.7267E−03, AC6 = 0.0000E+00,
AC8 = 0.0000E+00, AC10 = 0.0000E+00

45th surface

K = −0.2430
AC2 = 0.0000E+00, AC4 = −1.7267E−03, AC6 = 0.0000E+00,
AC8 = 0.0000E+00, AC10 = 0.0000E+00

49th surface

K = −0.2430
AC2 = 0.0000E+00, AC4 = 1.7267E−03, AC6 = 0.0000E+00,
AC8 = 0.0000E+00, AC10 = 0.0000E+00

Various data

| | |
|---|---|
| OB | 16.7487 |
| FOV | 90.8 |
| NAI | 0.1258 |
| IH | 1 |
| IHtotal | 1.021 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53_O_3 | 1.806250 | 1.800394 | 1.820103 | 1.831320 | 1.810931 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-FPL53_O_3 | 1.438750 | 1.437333 | 1.441955 | 1.444423 | 1.439854 |
| S-FPL55_O_1 | 1.438750 | 1.437328 | 1.441963 | 1.444438 | 1.439857 |
| S-LAH53_O_3 | 1.806098 | 1.800248 | 1.819945 | 1.831174 | 1.810775 |
| S-LAH60_O_3 | 1.834000 | 1.827376 | 1.849819 | 1.862781 | 1.839323 |

-continued

| Unit mm | | | | | |
|---|---|---|---|---|---|
| S-TIH53__O__3 | 1.846660 | 1.836488 | 1.872096 | 1.894189 | 1.855041 |
| S-TIL25__O__3 | 1.581439 | 1.577216 | 1.591486 | 1.599726 | 1.584822 |
| Resin B | 1.633870 | 1.626381 | 1.653490 | 1.671615 | 1.640183 |

| Ideal lens | |
|---|---|
| Displacement position | 62 (Pupil) |
| Focal length | 7.9139 |

Example 3

| Unit mm | | | | | |
|---|---|---|---|---|---|
| Surface data | | | | | |
| Surface no. | r | d | GLA | nd | vd | ER |
| Object plane | ∞ | 16.7947 | | 1. | | |
| 1 | ∞ | 0.2351 | C1 | 1.76900 | 64.15 | 1.176U |
| 2 | ∞ | 0.0672 | | 1. | | 1.176U |
| 3* | 1.1823 | 0.3133 | S-LAH53__O | 1.80610 | 40.92 | 0.857U |
| 4* | 0.3078 | 0.5235 | | 1. | | 0.537U |
| 5 | ∞ | 1.7634 | S-LAH53__O | 1.80610 | 40.95 | 1.226U |
| 6 | ∞ | 3.6605 | S-LAH53__O | 1.80610 | 40.92 | 1.226U |
| 7* | −2.1281 | 0.2948 | | 1. | | 1.226U |
| 8 | 15.8161 | 1.0071 | S-FPL53__O | 1.43875 | 94.93 | 1.226U |
| 9 | −2.0899 | 0.4191 | S-LAH60__O | 1.83400 | 37.16 | 1.226U |
| 10 | −3.1527 | 0.5491 | | 1. | | 1.226U |
| 11 | −35.1410 | 1.0914 | S-TIH53__O | 1.84666 | 23.78 | 1.226U |
| 12 | 2.4529 | 3.9709 | S-FPL53__O | 1.43875 | 94.93 | 1.226U |
| 13 | −3.4576 | 2.2092 | | 1. | | 1.226U |
| 14 | ∞ | 1.6795 | | 1. | | 1.344U |
| 15 | 6.0237 | 10.1210 | S-BAL35__O | 1.58913 | 61.14 | 1.260U |
| 16 | ∞ | 0.9862 | | 1. | | 1.260U |
| 17 | 7.3073 | 0.9653 | S-FPL51__O | 1.49700 | 81.54 | 1.260U |
| 18 | −3.2525 | 0.1679 | Resin B | 1.63387 | 23.38 | 1.260U |
| 19* | −3.0687 | 1.5449 | L-LAH53__O | 1.80610 | 40.88 | 1.260U |
| 20 | −6.6440 | 1.8870 | | 1. | | 1.260U |
| 21 | 6.6440 | 1.5449 | L-LAH53__O | 1.80610 | 40.88 | 1.260U |
| 22* | 3.0687 | 0.1679 | Resin B | 1.63387 | 23.38 | 1.260U |
| 23 | 3.2525 | 0.9653 | S-FPL51__O | 1.49700 | 81.54 | 1.260U |
| 24 | −7.3073 | 0.9862 | | 1. | | 1.260U |
| 25 | ∞ | 10.1210 | S-BAL35__O | 1.58913 | 61.14 | 1.260U |
| 26 | −6.0237 | 1.6795 | | 1. | | 1.260U |
| 27 | ∞ | 1.6795 | | 1. | | 1.344U |
| 28 | 6.0237 | 10.1210 | S-BAL35__O | 1.58913 | 61.14 | 1.260U |
| 29 | ∞ | 0.9862 | | 1. | | 1.260U |
| 30 | 7.3073 | 0.9653 | S-FPL51__O | 1.49700 | 81.54 | 1.260U |
| 31 | −3.2525 | 0.1679 | Resin B | 1.63387 | 23.38 | 1.260U |
| 32* | −3.0687 | 1.5449 | L-LAH53__O | 1.80610 | 40.88 | 1.260U |
| 33 | −6.6440 | 1.8870 | | 1. | | 1.260U |
| 34 | 6.6440 | 1.5449 | L-LAH53__O | 1.80610 | 40.88 | 1.260U |
| 35* | 3.0687 | 0.1679 | Resin B | 1.63387 | 23.38 | 1.260U |
| 36 | 3.2525 | 0.9653 | S-FPL51__O | 1.49700 | 81.54 | 1.260U |
| 37 | −7.3073 | 0.9862 | | 1. | | 1.260U |
| 38 | ∞ | 10.1210 | S-BAL35__O | 1.58913 | 61.14 | 1.260U |
| 39 | −6.0237 | 1.6795 | | 1. | | 1.260U |
| 40 | ∞ | 1.6795 | | 1. | | 1.344U |
| 41 | 6.0237 | 10.1210 | S-BAL35__O | 1.58913 | 61.14 | 1.260U |
| 42 | ∞ | 0.9862 | | 1. | | 1.260U |
| 43 | 7.3073 | 0.9653 | S-FPL51__O | 1.49700 | 81.54 | 1.260U |
| 44 | −3.2525 | 0.1679 | Resin B | 1.63387 | 23.38 | 1.260U |
| 45* | −3.0687 | 1.5449 | L-LAH53__O | 1.80610 | 40.88 | 1.260U |
| 46 | −6.6440 | 0.9435 | | 1. | | 1.260U |
| 47 (Stop) | ∞ | 0.9435 | | 1. | | 1.234U |
| 48 | 6.6440 | 1.5449 | L-LAH53__O | 1.80610 | 40.88 | 1.260U |
| 49* | 3.0687 | 0.1679 | Resin B | 1.63387 | 23.38 | 1.260U |
| 50 | 3.2525 | 0.9653 | S-FPL51__O | 1.49700 | 81.54 | 1.260U |
| 51 | −7.3073 | 0.9862 | | 1. | | 1.260U |
| 52 | ∞ | 10.1210 | S-BAL35__O | 1.58913 | 61.14 | 1.260U |
| 53 | −6.0237 | 1.6795 | | 1. | | 1.260U |
| 54 | ∞ | 5.9688 | | 1. | | 1.646U |
| 55 | 24.7053 | 0.9283 | S-FPL53__O | 1.43875 | 94.93 | 1.679U |

-continued

| | | | Unit mm | | | |
|---|---|---|---|---|---|---|
| 56 | −6.7559 | 0.5497 | | 1. | | 1.679U |
| 57 | 46.3270 | 0.5401 | S-TIM25_O | 1.67270 | 32.10 | 1.679U |
| 58 | 4.0212 | 0.1347 | Resin B | 1.63387 | 23.38 | 1.679U |
| 59 | 5.1273 | 2.4088 | S-FSL5_O | 1.48749 | 70.23 | 1.624 |
| 60 | −6.3689 | 2.2260 | | 1. | | 1.679U |
| 61 | ∞ | 1.0077 | CG3 | 1.76820 | 71.70 | 1.679U |
| 62 | ∞ | 3.5269 | | 1. | | 1.679U |
| 63 (Pupil) | ∞ | 8.1411 | | 1. | | 1.127U |
| Image plane | ∞ | 0. | | | | |

Aspherical surface data

3rd surface

K = −1.0660
AC2 = 0.0000E+00, AC4 = −2.5460E−01, AC6 = 8.4252E−02,
AC8 = 0.0000E+00, AC10 = 0.0000E+00
4th surface K = −0.8249
AC2 = 0.0000E+00, AC4 = −1.2575E−01, AC6 = −2.0645E+00,
AC8 = 0.0000E+00, AC10 = 0.0000E+00
7th surface K = −0.4472
AC2 = 0.0000E+00, AC4 = 5.2867E−03, AC6 = 0.0000E+00,
AC8 = 0.0000E+00, AC10 = 0.0000E+00
19th surface K = 0.
AC2 = 0.0000E+00, AC4 = −8.3572E−04, AC6 = 8.9291E−05,
AC8 = 1.4906E−05, AC10 = 0.0000E+00
22nd surface K = 0.
AC2 = 0.0000E+00, AC4 = 8.3572E−04, AC6 = −8.9291E−05,
AC8 = −1.4906E−05, AC10 = 0.0000E+00
32nd surface K = 0.
AC2 = 0.0000E+00, AC4 = −8.3572E−04, AC6 = 8.9291E−05,
AC8 = 1.4906E−05, AC10 = 0.0000E+00
35th surface K = 0.
AC2 = 0.0000E+00, AC4 = 8.3572E−04, AC6 = −8.9291E−05,
AC8 = −1.4906E−05, AC10 = 0.0000E+00
45th surface K = 0.
AC2 = 0.0000E+00, AC4 = −8.3572E−04, AC6 = 8.9291E−05,
AC8 = 1.4906E−05, AC10 = 0.0000E+00
49th surface K = 0.
AC2 = 0.0000E+00, AC4 = 8.3572E−04, AC6 = −8.9291E−05,
AC8 = −1.4906E−05, AC10 = 0.0000E+00

Various data

| OB | 16.7947 |
|---|---|
| FOV | 90.7 |
| NAI | 0.1257 |
| IH | 1 |
| IHtotal | 1.024 |

Glass material data

| GLA | 587.56 | 656.27 | 486.13 | 435.83 | 546.07 |
|---|---|---|---|---|---|
| CG3 | 1.768199 | 1.765254 | 1.775966 | 1.783513 | 1.770666 |
| C1 | 1.768999 | 1.765391 | 1.777377 | 1.784102 | 1.771846 |
| L-LAH53_O_2 | 1.806098 | 1.800238 | 1.819956 | 1.831172 | 1.810782 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-FPL53_O_3 | 1.438750 | 1.437333 | 1.441955 | 1.444423 | 1.439854 |
| S-FSL5_O_3 | 1.487490 | 1.485344 | 1.492285 | 1.495964 | 1.489147 |
| S-LAH53_O_1 | 1.806098 | 1.800251 | 1.819937 | 1.831152 | 1.810773 |

-continued

| Unit mm | | | | | |
|---|---|---|---|---|---|
| S-LAH53_O_3 | 1.806098 | 1.800248 | 1.819945 | 1.831174 | 1.810775 |
| S-LAH60_O_3 | 1.834000 | 1.827376 | 1.849819 | 1.862781 | 1.839323 |
| S-TIH53_O_3 | 1.846660 | 1.836488 | 1.872096 | 1.894189 | 1.855041 |
| S-TIM25_O_3 | 1.672700 | 1.666607 | 1.687564 | 1.700114 | 1.677651 |
| Resin B | 1.633870 | 1.626381 | 1.653490 | 1.671615 | 1.640183 |

| Ideal lens | |
|---|---|
| Displacement position | 63 (Pupil) |
| Focal length | 7.9452 |

Example 4

| Unit mm | | | | | |
|---|---|---|---|---|---|
| Surface data | | | | | |
| Surface no. | r | d | GLA | nd | vd | ER |
| Object plane | ∞ | 16.7552 | | 1. | | |
| 1 | ∞ | 0.2346 | C1 | 1.76900 | 64.15 | 1.173U |
| 2 | ∞ | 0.0670 | | 1. | | 1.173U |
| 3* | 1.4224 | 0.3128 | S-LAH53_O | 1.80610 | 40.92 | 0.855U |
| 4* | 0.3389 | 0.4895 | | 1. | | 0.536U |
| 5 | ∞ | 1.7593 | S-LAH53_O | 1.80610 | 40.95 | 1.223U |
| 6 | ∞ | 3.3532 | S-LAH53_O | 1.80610 | 40.92 | 1.223U |
| 7* | −2.0860 | 0.3233 | | 1. | | 1.223U |
| 8 | −7.0178 | 0.4501 | S-LAH60_O | 1.83400 | 37.16 | 1.223U |
| 9 | 5.1534 | 1.0057 | S-FPL51_O | 1.49700 | 81.54 | 1.223U |
| 10 | −2.6464 | 1.9507 | | 1. | | 1.223U |
| 11 | 7.4119 | 0.8901 | S-TIH53_O | 1.84666 | 23.78 | 1.223U |
| 12 | 2.1932 | 3.2295 | S-FPL51_O | 1.49700 | 81.54 | 1.223U |
| 13 | −4.8427 | 2.2379 | | 1. | | 1.223U |
| 14 | ∞ | 1.5100 | | 1. | | 1.340U |
| 15 | 6.6964 | 8.1985 | S-BAL35_O | 1.58913 | 61.14 | 1.257U |
| 16 | ∞ | 2.9407 | | 1. | | 1.257U |
| 17 | 9.9783 | 0.8588 | S-LAL7_O | 1.65160 | 58.55 | 1.257U |
| 18 | −3.5435 | 1.1200 | S-LAH58_O | 1.88300 | 40.76 | 1.257U |
| 19 | −9.5666 | 1.2704 | | 1. | | 1.257U |
| 20 | ∞ | 0.3351 | Resin B | 1.63387 | 23.38 | 1.257U |
| 21# | 1.671E+05 | 0. | DOE_P | 1.0E+03 | −3.45 | 1.232U |
| 22 | ∞ | 0.3351 | Resin C | 1.69534 | 36.44 | 1.257U |
| 23 | ∞ | 1.2704 | | 1. | | 1.257U |
| 24 | 9.5666 | 1.1200 | S-LAH58_O | 1.88300 | 40.76 | 1.257U |
| 25 | 3.5435 | 0.8588 | S-LAL7_O | 1.65160 | 58.55 | 1.257U |
| 26 | −9.9783 | 2.9407 | | 1. | | 1.257U |
| 27 | ∞ | 8.1985 | S-BAL35_O | 1.58913 | 61.14 | 1.257U |
| 28 | −6.6964 | 1.5100 | | 1. | | 1.257U |
| 29 | ∞ | 1.7562 | | 1. | | 1.340U |
| 30 | 6.6964 | 8.1985 | S-BAL35_O | 1.58913 | 61.14 | 1.257U |
| 31 | ∞ | 2.9407 | | 1. | | 1.257U |
| 32 | 9.9783 | 0.8588 | S-LAL7_O | 1.65160 | 58.55 | 1.257U |
| 33 | −3.5435 | 1.1200 | S-LAH58_O | 1.88300 | 40.76 | 1.257U |
| 34 | −9.5666 | 3.2110 | | 1. | | 1.257U |
| 35 | 9.5666 | 1.1200 | S-LAH58_O | 1.88300 | 40.76 | 1.257U |
| 36 | 3.5435 | 0.8588 | S-LAL7_O | 1.65160 | 58.55 | 1.257U |
| 37 | −9.9783 | 2.9407 | | 1. | | 1.257U |
| 38 | ∞ | 8.1985 | S-BAL35_O | 1.58913 | 61.14 | 1.257U |
| 39 | −6.6964 | 1.7562 | | 1. | | 1.257U |
| 40 | ∞ | 1.7562 | | 1. | | 1.340U |
| 41 | 6.6964 | 8.1985 | S-BAL35_O | 1.58913 | 61.14 | 1.257U |
| 42 | ∞ | 2.9407 | | 1. | | 1.257U |
| 43 | 9.9783 | 0.8588 | S-LAL7_O | 1.65160 | 58.55 | 1.257U |
| 44 | −3.5435 | 1.1200 | S-LAH58_O | 1.88300 | 40.76 | 1.257U |
| 45 | −9.5666 | 1.6055 | | 1. | | 1.257U |
| 46 (Stop) | ∞ | 1.6055 | | 1. | | 1.173U |
| 47 | 9.5666 | 1.1200 | S-LAH58_O | 1.88300 | 40.76 | 1.257U |
| 48 | 3.5435 | 0.8588 | S-LAL7_O | 1.65160 | 58.55 | 1.257U |
| 49 | −9.9783 | 2.9407 | | 1. | | 1.257U |
| 50 | ∞ | 8.1985 | S-BAL35_O | 1.58913 | 61.14 | 1.257U |
| 51 | −6.6964 | 1.7562 | | 1. | | 1.257U |
| 52 | ∞ | 5.4204 | | 1. | | 1.676U |
| 53 | 11.2751 | 1.3885 | S-FPL53_O | 1.43875 | 94.93 | 1.676U |

-continued

| | | | Unit mm | | | |
|---|---|---|---|---|---|---|
| 54 | −8.0030 | 0.7270 | | 1. | | 1.676U |
| 55 | 75.1448 | 0.4979 | S-LAH60_O | 1.83400 | 37.16 | 1.676U |
| 56 | 4.6117 | 2.9738 | S-BAL35_O | 1.58913 | 61.14 | 1.676U |
| 57 | −6.6702 | 1.7959 | | 1. | | 1.676U |
| 58 | ∞ | 1.0053 | C2 | 1.76819 | 71.70 | 1.508U |
| 59 | ∞ | 3.5186 | | 1. | | 1.508U |
| 60 (Pupil) | ∞ | 8.1203 | | 1. | | 1.020 |
| Image plane | ∞ | 0. | | | | |

Aspherical surface data

3rd surface

K = 0.1140
AC2 = 0.0000E+00, AC4 = −2.2110E−01, AC6 = 4.5240E−02,
AC8 = 0.0000E+00, AC10 = 0.0000E+00
4th surface K = −0.7518
AC2 = 0.0000E+00, AC4 = −1.7207E−01, AC6 = −1.7200E+00,
AC8 = 0.0000E+00, AC10 = 0.0000E+00
7th surface K = −0.6975
AC2 = 0.0000E+00, AC4 = 5.4384E−03, AC6 = −1.3278E−04,
AC8 = 0.0000E+00, AC10 = 0.0000E+00
Diffractive surface data
21st surface K = 0.
AC2 = 0.0000E+00, AC4 = −3.2642E−07, AC6 = 5.5723E−08,
AC8 = 0.0000E+00, AC10 = 0.0000E+00

Various data

| | | |
|---|---|---|
| OB | | 16.7552 |
| FOV | | 89.5 |
| NAI | | 0.1257 |
| IH | | 1 |
| IHtotal | | 1.021 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| DOE_P | 1.00E+03 | 1.12E+03 | 8.28E+02 | 7.43E+02 | 9.30E+02 |
| Resin C | 1.695340 | 1.689750 | 1.708830 | 1.719980 | 1.699860 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-FPL53_O_3 | 1.438750 | 1.437333 | 1.441955 | 1.444423 | 1.439854 |
| S-LAH53_O_1 | 1.806098 | 1.800251 | 1.819937 | 1.831152 | 1.810773 |
| S-LAH53_O_3 | 1.806098 | 1.800248 | 1.819945 | 1.831174 | 1.810775 |
| S-LAH58_O_3 | 1.882997 | 1.876560 | 1.898221 | 1.910497 | 1.888146 |
| S-LAH60_O_3 | 1.834000 | 1.827376 | 1.849819 | 1.862781 | 1.839323 |
| S-LAL7_O_3 | 1.651597 | 1.648207 | 1.659336 | 1.665374 | 1.654251 |
| S-TIH53_O_3 | 1.846660 | 1.836488 | 1.872096 | 1.894189 | 1.855041 |
| Resin B | 1.633870 | 1.626381 | 1.653490 | 1.671615 | 1.640183 |

Ideal lens

| | |
|---|---|
| Displacement position | 60 (Pupil) |
| Focal length | 7.9250 |

Example 5

| | | | Unit mm | | | |
|---|---|---|---|---|---|---|
| | | | Surface data | | | |
| Surface no. | r | d | GLA | nd | νd | ER |
| Object plane | ∞ | 16.7554 | | 1. | | |
| 1 | ∞ | 0.2346 | C1 | 1.76900 | 64.15 | 1.173U |
| 2 | ∞ | 0.0670 | | 1. | | 1.173U |
| 3* | 1.6016 | 0.3560 | S-LAH53_O | 1.80610 | 40.92 | 0.855U |
| 4* | 0.3494 | 0.4729 | | | | 0.536U |
| 5 | ∞ | 1.7593 | S-LAH53_O | 1.80610 | 40.95 | 1.223U |
| 6 | ∞ | 3.4856 | S-LAH53_O | 1.80610 | 40.92 | 1.223U |
| 7* | −2.1241 | 0.3256 | | 1. | | 1.223U |
| 8 | −12.2822 | 0.3512 | S-LAH60_O | 1.83400 | 37.16 | 1.223U |
| 9 | 4.8421 | 1.0832 | S-FPL53_O | 1.43875 | 94.93 | 1.223U |
| 10 | −2.3841 | 1.4761 | | 1. | | 1.223U |
| 11 | 8.5709 | 1.0559 | S-TIH53_O | 1.84666 | 23.78 | 1.223U |
| 12 | 2.0058 | 0.1731 | Resin B | 1.63387 | 23.38 | 1.223U |
| 13 | 2.2328 | 3.4056 | S-FPL53_O | 1.43875 | 94.93 | 1.223U |
| 14 | −3.6645 | 1.9473 | | 1. | | 1.223U |
| 15 | ∞ | 1.5038 | | 1. | | 1.340U |
| 16 | 6.7109 | 8.2074 | S-BAL35_O | 1.58913 | 61.14 | 1.257U |
| 17 | ∞ | 2.7639 | | 1. | | 1.257U |
| 18 | 9.5589 | 0.8673 | S-LAL7_O | 1.65160 | 58.55 | 1.257U |
| 19 | −3.4911 | 1.2200 | S-LAH58_O | 1.88300 | 40.76 | 1.257U |
| 20 | −9.6094 | 1.3423 | | 1. | | 1.257U |
| 21 | ∞ | 0.3351 | Resin B | 1.63387 | 23.38 | 1.257U |
| 22# | 1.691E+05 | 0. | DOE _P | 1.0E+03 | −3.45 | 1.232U |
| 23 | ∞ | 0.3351 | Resin C | 1.69534 | 36.44 | 1.257U |
| 24 | ∞ | 1.3423 | | 1. | | 1.257U |
| 25 | 9.6094 | 1.2200 | S-LAH58_O | 1.88300 | 40.76 | 1.257U |
| 26 | 3.4911 | 0.8673 | S-LAL7_O | 1.65160 | 58.55 | 1.257U |
| 27 | −9.5589 | 2.7639 | | 1. | | 1.257U |
| 28 | ∞ | 8.2074 | S-BAL35_O | 1.58913 | 61.14 | 1.257U |
| 29 | −6.7109 | 1.5038 | | 1. | | 1.257U |
| 30 | ∞ | 1.7411 | | 1. | | 1.340U |
| 31 | 6.7109 | 8.2074 | S-BAL35_O | 1.58913 | 61.14 | 1.257U |
| 32 | ∞ | 2.7639 | | 1. | | 1.257U |
| 33 | 9.5589 | 0.8673 | S-LAL7_O | 1.65160 | 58.55 | 1.257U |
| 34 | −3.4911 | 1.2200 | S-LAH58_O | 1.88300 | 40.76 | 1.257U |
| 35 | −9.6094 | 3.3548 | | 1. | | 1.257U |
| 36 | 9.6094 | 1.2200 | S-LAH58_O | 1.88300 | 40.76 | 1.257U |
| 37 | 3.4911 | 0.8673 | S-LAL7_O | 1.65160 | 58.55 | 1.257U |
| 38 | −9.5589 | 2.7639 | | 1. | | 1.257U |
| 39 | ∞ | 8.2074 | S-BAL35_O | 1.58913 | 61.14 | 1.257U |
| 40 | −6.7109 | 1.7411 | | 1. | | 1.257U |
| 41 | ∞ | 1.7411 | | 1. | | 1.340U |
| 42 | 6.7109 | 8.2074 | S-BAL35_O | 1.58913 | 61.14 | 1.257U |
| 43 | ∞ | 2.7639 | | 1. | | 1.257U |
| 44 | 9.5589 | 0.8673 | S-LAL7_O | 1.65160 | 58.55 | 1.257U |
| 45 | −3.4911 | 1.2200 | S-LAH58_O | 1.88300 | 40.76 | 1.257U |
| 46 | −9.6094 | 1.6774 | | 1. | | 1.257U |
| 47 (Stop) | ∞ | 1.6774 | | 1. | | 1.158U |
| 48 | 9.6094 | 1.2200 | S-LAH58_O | 1.88300 | 40.76 | 1.257U |
| 49 | 3.4911 | 0.8673 | S-LAL7_O | 1.65160 | 58.55 | 1.257U |
| 50 | −9.5589 | 2.7639 | | 1. | | 1.257U |
| 51 | ∞ | 8.2074 | S-BAL35_O | 1.58913 | 61.14 | 1.257U |
| 52 | −6.7109 | 1.7411 | | 1. | | 1.257U |
| 53 | ∞ | 5.4205 | | 1. | | 1.676U |
| 54 | 11.2752 | 1.3885 | S-FPL53_O | 1.43875 | 94.93 | 1.676U |
| 55 | −8.0031 | 0.7270 | | 1. | | 1.676U |
| 56 | 75.1455 | 0.4979 | S-LAH60_O | 1.83400 | 37.16 | 1.676U |
| 57 | 4.6117 | 2.9738 | S-BAL35_O | 1.58913 | 61.14 | 1.676U |
| 58 | −6.6703 | 1.7959 | | 1. | | 1.676U |
| 59 | ∞ | 1.0053 | C2 | 1.76819 | 71.70 | 1.508U |
| 60 | ∞ | 3.5186 | | 1. | | 1.508U |
| 61 (Pupil) | ∞ | 8.1204 | | 1. | | 1.020 |
| Image plane | ∞ | 0. | | | | |

| Aspherical surface data |
|---|
| 3rd surface |

K = 0.3843
AC2 = 0.0000E+00, AC4 = −1.5201E−01, AC6 = 3.9171E−03,
AC8 = 0.0000E+00, AC10 = 0.0000E+00

-continued

| Unit mm |
|---|

4th surface

K = −0.8382
AC2 = 0.0000E+00, AC4 = 2.1019E−01, AC6 = −9.9216E−01,
AC8 = 0.0000E+00, AC10 = 0.0000E+00

7th surface

K = −0.8573
AC2 = 0.0000E+00, AC4 = 5.3385E−03, AC6 = 2.6808E−05,
AC8 = 0.0000E+00, AC10 = 0.0000E+00

Diffractive surface data
22nd surface

K = 0.
AC2 = 0.0000E+00, AC4 = −4.0014E−07, AC6 = 6.7888E−08,
AC8 = −1.5752E−09, AC10 = 0.0000E+00

Various data

| | |
|---|---|
| OB | 16.7554 |
| FOV | 88.7 |
| NAI | 0.1257 |
| IH | 1 |
| IHtotal | 1.021 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| DOE_P | 1.00E+03 | 1.12E+03 | 8.28E+02 | 7.43E+02 | 9.30E+02 |
| Resin C | 1.695340 | 1.689750 | 1.708830 | 1.719980 | 1.699860 |
| S-BAL35_O_3 | 1.589130 | 1.586188 | 1.595824 | 1.601034 | 1.591429 |
| S-FPL53_O_3 | 1.438750 | 1.437333 | 1.441955 | 1.444423 | 1.439854 |
| S-LAH53_O_1 | 1.806098 | 1.800251 | 1.819937 | 1.831152 | 1.810773 |
| S-LAH53_O_3 | 1.806098 | 1.800248 | 1.819945 | 1.831174 | 1.810775 |
| S-LAH58_O_3 | 1.882997 | 1.876560 | 1.898221 | 1.910497 | 1.888146 |
| S-LAH60_O_3 | 1.834000 | 1.827376 | 1.849819 | 1.862781 | 1.839323 |
| S-LAL7_O_3 | 1.651597 | 1.648207 | 1.659336 | 1.665374 | 1.654251 |
| S-TIH53_O_3 | 1.846660 | 1.836488 | 1.872096 | 1.894189 | 1.855041 |
| Resin B | 1.633870 | 1.626381 | 1.653490 | 1.671615 | 1.640183 |

Ideal lens

| | |
|---|---|
| Displacement position | 61 (Pupil) |
| Focal length | 7.9254 |

Example 6

| Unit mm |
|---|

Surface data

| Surface no. | r | d | GLA | nd | vd | ER |
|---|---|---|---|---|---|---|
| Object plane | ∞ | 16.7886 | | 1. | | |
| 1 | ∞ | 0.2350 | C1 | 1.76900 | 64.15 | 1.175U |
| 2 | ∞ | 0.0672 | | 1. | | 1.175U |
| 3* | 1.1728 | 0.3541 | L-LAH86_O | 1.90270 | 31.00 | 0.856U |
| 4* | 0.3243 | 0.5096 | | 1. | | 0.537U |
| 5 | ∞ | 1.7628 | S-LAH53_O | 1.80610 | 40.95 | 1.226U |
| 6 | ∞ | 3.9654 | L-LAH53_O | 1.80625 | 40.91 | 1.226U |
| 7* | −2.2727 | 0.7512 | | 1. | | 1.226U |
| 8 | 4.9725 | 1.0926 | S-FPL55_O | 1.43875 | 94.66 | 1.226U |
| 9 | −2.5109 | 0.4090 | S-TIM28_O | 1.68893 | 31.07 | 1.226U |
| 10 | −4.4812 | 0.6178 | | 1. | | 1.226U |
| 11 | −15.1435 | 0.4045 | S-NBH56_O | 1.85478 | 24.80 | 1.226U |
| 12 | 2.0797 | 3.5206 | S-FPL55_O | 1.43875 | 94.66 | 1.226U |
| 13 | −3.0405 | 2.3561 | | 1. | | 1.226U |
| 14 | ∞ | 1.7393 | | 1. | | 1.343U |
| 15 | 6.0577 | 10.9529 | S-BAL35_O | 1.58913 | 61.14 | 1.259U |
| 16 | ∞ | 0.3190 | | 1. | | 1.259U |
| 17* | 6.4784 | 1.8803 | S-FPL55_O | 1.43875 | 94.66 | 1.259U |

-continued

| | | | Unit mm | | | |
|---|---|---|---|---|---|---|
| 18 | −3.5636 | 0.6715 | S-YGH51_O | 1.75500 | 52.32 | 1.259U |
| 19 | −6.2561 | 1.6788 | | 1. | | 1.259U |
| 20 | 6.2561 | 0.6715 | S-YGH51_O | 1.75500 | 52.32 | 1.259U |
| 21 | 3.5636 | 1.8803 | S-FPL55_O | 1.43875 | 94.66 | 1.259U |
| 22* | −6.4784 | 0.3190 | | 1. | | 1.259U |
| 23 | ∞ | 10.9529 | S-BAL35_O | 1.58913 | 61.14 | 1.259U |
| 24 | −6.0577 | 1.7393 | | 1. | | 1.259U |
| 25 | ∞ | 1.7393 | | 1. | | 1.343U |
| 26 | 6.0577 | 10.9529 | S-BAL35_O | 1.58913 | 61.14 | 1.259U |
| 27 | ∞ | 0.3190 | | 1. | | 1.259U |
| 28* | 6.4784 | 1.8803 | S-FPL55_O | 1.43875 | 94.66 | 1.259U |
| 29 | −3.5636 | 0.6715 | S-YGH51_O | 1.75500 | 52.32 | 1.259U |
| 30 | −6.2561 | 1.6788 | | 1. | | 1.259U |
| 31 | 6.2561 | 0.6715 | S-YGH51_O | 1.75500 | 52.32 | 1.259U |
| 32 | 3.5636 | 1.8803 | S-FPL55_O | 1.43875 | 94.66 | 1.259U |
| 33* | −6.4784 | 0.3190 | | 1. | | 1.259U |
| 34 | ∞ | 10.9529 | S-BAL35_O | 1.58913 | 61.14 | 1.259U |
| 35 | −6.0577 | 1.7393 | | 1. | | 1.259U |
| 36 | ∞ | 1.7393 | | 1. | | 1.343U |
| 37 | 6.0577 | 10.9529 | S-BAL35_O | 1.58913 | 61.14 | 1.259U |
| 38 | ∞ | 0.3190 | | 1. | | 1.259U |
| 39* | 6.4784 | 1.8803 | S-FPL55_O | 1.43875 | 94.66 | 1.259U |
| 40 | −3.563 | 0.6715 | S-YGH51_O | 1.75500 | 52.32 | 1.259U |
| 41 | −6.2561 | 0.8394 | | 1. | | 1.259U |
| 42 (Stop) | ∞ | 0.8394 | | 1. | | 1.078U |
| 43 | 6.2561 | 0.6715 | S-YGH51_O | 1.75500 | 52.32 | 1.259U |
| 44 | 3.5636 | 1.8803 | S-FPL55_O | 1.43875 | 94.66 | 1.259U |
| 45* | −6.4784 | 0.3190 | | 1. | | 1.259U |
| 46 | ∞ | 10.9529 | S-BAL35_O | 1.58913 | 61.14 | 1.259U |
| 47 | −6.0577 | 1.7393 | | 1. | | 1.259U |
| 48 | ∞ | 7.1654 | | 1. | | 1.679U |
| 49 | 7.5661 | 0.4972 | L-LAH86_O | 1.90270 | 31.00 | 1.679U |
| 50* | 4.3579 | 0.0976 | Resin B | 1.63387 | 23.38 | 1.679U |
| 51 | 4.5592 | 1.3361 | S-FPL51_O | 1.49700 | 81.54 | 1.679U |
| 52 | −5.0560 | 3.4864 | | 1. | | 1.679U |
| 53 | ∞ | 1.0073 | C2 | 1.76819 | 71.70 | 1.679U |
| 54 | ∞ | 3.5256 | | 1. | | 1.679U |
| 55 (Pupil) | ∞ | 8.1440 | | 1. | | 1.107U |
| Image plane | ∞ | 0. | | | | |

Aspherical surface data

3rd surface

K = −1.0661
AC2 = 0.0000E+00, AC4 = −1.6336E−01, AC6 = 3.5822E−02,
AC8 = 0.0000E+00, AC10 = 0.0000E+00

4th surface

K = −1.0366
AC2 = 0.0000E+00, AC4 = 8.1428E−01, AC6 = −5.0872E−01,
AC8 = 0.0000E+00, AC10 = 0.0000E+00

7th surface

K = −0.4754
AC2 = 0.0000E+00, AC4 = 3.0963E−03, AC6 = 0.0000E+00,
AC8 = 0.0000E+00, AC10 = 0.0000E+00

17th surface

K = 1.6990
AC2 = 0.0000E+00, AC4 = −1.7979E−03, AC6 = 0.0000E+00,
AC8 = 0.0000E+00, AC10 = 0.0000E+00

22nd surface

K = 1.6990
AC2 = 0.0000E+00, AC4 = 1.7979E−03, AC6 = 0.0000E+00,
AC8 = 0.0000E+00, AC10 = 0.0000E+00

28th surface

K = 1.6990
AC2 = 0.0000E+00, AC4 = −1.7979E−03, AC6 = 0.0000E+00,
AC8 = 0.0000E+00, AC10 = 0.0000E+00

33rd surface

K = 1.6990
AC2 = 0.0000E+00, AC4 = 1.7979E−03, AC6 = 0.0000E+00,
AC8 = 0.0000E+00, AC10 = 0.0000E+00

-continued

| Unit mm |
|---|

39th surface

K = 1.6990
AC2 = 0.0000E+00, AC4 = −1.7979E−03, AC6 = 0.0000E+00,
AC8 = 0.0000E+00, AC10 = 0.0000E+00

45th surface

K = 1.6990
AC2 = 0.0000E+00, AC4 = 1.7979E−03, AC6 = 0.0000E+00,
AC8 = 0.0000E+00, AC10 = 0.0000E+00

50th surface

K = −1.3463
AC2 = 0.0000E+00, AC4 = 3.2418E−03, AC6 = −4.1779E−05,
AC8 = 0.0000E+00, AC10 = 0.0000E+00

Various data

| | |
|---|---|
| OB | 16.7886 |
| FOV | 88.7 |
| NAI | 0.1258 |
| IH | 1 |
| IHtotal | 1.021 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53_O_3 | 1.806250 | 1.800394 | 1.820103 | 1.831320 | 1.810931 |
| L-LAH86_O_2 | 1.902700 | 1.894221 | 1.923336 | 1.940638 | 1.909585 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-FPL55_O_1 | 1.438750 | 1.437328 | 1.441963 | 1.444438 | 1.439857 |
| S-LAH53_O_1 | 1.806098 | 1.800251 | 1.819937 | 1.831152 | 1.810773 |
| S-NBH56_O_1 | 1.854780 | 1.844876 | 1.879345 | 1.900448 | 1.862904 |
| S-TIM28_O_2 | 1.688931 | 1.682495 | 1.704665 | 1.717975 | 1.694167 |
| S-YGH51_O_3 | 1.754999 | 1.750624 | 1.765055 | 1.772956 | 1.758437 |
| Resin B | 1.633870 | 1.626381 | 1.653490 | 1.671615 | 1.640183 |

Ideal lens

| | |
|---|---|
| Displacement position | 55 (Pupil) |
| Focal length | 7.9487 |

Example 7

| Unit mm | | | | | |
|---|---|---|---|---|---|
| Surface data | | | | | |
| Surface no. | r | d | GLA | nd | vd | ER |

| Surface no. | r | d | GLA | nd | vd | ER |
|---|---|---|---|---|---|---|
| Object plane | ∞ | 16.8227 | | 1. | | |
| 1 | ∞ | 0.2355 | C1 | 1.76900 | 64.15 | 1.178U |
| 2 | ∞ | 0.0673 | | 1. | | 1.178U |
| 3 | 2.0162 | 0.3622 | S-BAH11_O | 1.66672 | 48.32 | 0.858U |
| 4* | 0.3233 | 0.5265 | | 1. | | 0.538U |
| 5 | ∞ | 1.7664 | S-LAH53_O | 1.80610 | 40.95 | 1.228U |
| 6 | ∞ | 3.6679 | L-LAH53_O | 1.80625 | 40.91 | 1.228U |
| 7* | −2.1804 | 0.2267 | | 1. | | 1.228U |
| 8 | 11.8764 | 1.1219 | S-FPL55_O | 1.43875 | 94.66 | 1.228U |
| 9 | −1.8882 | 0.3996 | S-TIL25_O | 1.58144 | 40.75 | 1.228U |
| 10 | −3.7315 | 0.2883 | | 1. | | 1.228U |
| 11 | 47.7595 | 1.0444 | S-NBH56_O | 1.85478 | 24.80 | 1.228U |
| 12 | 2.1407 | 4.9142 | S-FPL55_O | 1.43875 | 94.66 | 1.228U |
| 13 | −3.8938 | 1.5120 | | 1. | | 1.228U |
| 14 | ∞ | 1.7428 | | 1. | | 1.346U |
| 15 | 6.0700 | 10.9751 | S-BAL35_O | 1.58913 | 61.14 | 1.262U |
| 16 | ∞ | 0.3196 | | 1. | | 1.262U |
| 17* | 6.4916 | 1.8841 | S-FPL55_O | 1.43875 | 94.66 | 1.262U |
| 18 | −3.5708 | 0.6729 | S-YGH51_O | 1.75500 | 52.32 | 1.262U |
| 19 | −6.2688 | 1.6822 | | 1. | | 1.262U |

-continued

| Unit mm | | | | | | |
|---|---|---|---|---|---|---|
| 20 | 6.2688 | 0.6729 | S-YGH51_O | 1.75500 | 52.32 | 1.262U |
| 21 | 3.5708 | 1.8841 | S-FPL55_O | 1.43875 | 94.66 | 1.262U |
| 22* | −6.4916 | 0.3196 | | 1. | | 1.262U |
| 23 | ∞ | 10.9751 | S-BAL35_O | 1.58913 | 61.14 | 1.262U |
| 24 | −6.0700 | 1.7428 | | 1. | | 1.262U |
| 25 | ∞ | 1.7428 | | 1. | | 1.346U |
| 26 | 6.0700 | 10.9751 | S-BAL35_O | 1.58913 | 61.14 | 1.262U |
| 27 | ∞ | 0.3196 | | 1. | | 1.262U |
| 28* | 6.4916 | 1.8841 | S-FPL55_O | 1.43875 | 94.66 | 1.262U |
| 29 | −3.5708 | 0.6729 | S-YGH51_O | 1.75500 | 52.32 | 1.262U |
| 30 | −6.2688 | 1.6822 | | 1. | | 1.262U |
| 31 | 6.2688 | 0.6729 | S-YGH51_O | 1.75500 | 52.32 | 1.262U |
| 32 | 3.5708 | 1.8841 | S-FPL55_O | 1.43875 | 94.66 | 1.262U |
| 33* | −6.4916 | 0.3196 | | 1. | | 1.262U |
| 34 | ∞ | 10.9751 | S-BAL35_O | 1.58913 | 61.14 | 1.262U |
| 35 | −6.0700 | 1.7428 | | 1. | | 1.262U |
| 36 | ∞ | 1.7428 | | 1. | | 1.346U |
| 37 | 6.0700 | 10.9751 | S-BAL35_O | 1.58913 | 61.14 | 1.262U |
| 38 | ∞ | 0.3196 | | 1. | | 1.262U |
| 39* | 6.4916 | 1.8841 | S-FPL55_O | 1.43875 | 94.66 | 1.262U |
| 40 | −3.5708 | 0.6729 | S-YGH51_O | 1.75500 | 52.32 | 1.262U |
| 41 | −6.2688 | 0.8411 | | 1. | | 1.262U |
| 42 (Stop) | ∞ | 0.8411 | | 1. | | 1.080U |
| 43 | 6.2688 | 0.6729 | S-YGH51_O | 1.75500 | 52.32 | 1.262U |
| 44 | 3.5708 | 1.8841 | S-FPL55_O | 1.43875 | 94.66 | 1.262U |
| 45* | −6.4916 | 0.3196 | | 1. | | 1.262U |
| 46 | ∞ | 10.9751 | S-BAL35_O | 1.58913 | 61.14 | 1.262U |
| 47 | −6.0700 | 1.7428 | | 1. | | 1.262U |
| 48 | ∞ | 5.4943 | | 1. | | 1.682U |
| 49 | 11.4018 | 1.5813 | S-FPL51_O | 1.49700 | 81.54 | 1.682U |
| 50 | −7.8703 | 0.2355 | | 1. | | 1.682U |
| 51 | ∞ | 0.5047 | S-LAH60_O | 1.83400 | 37.16 | 1.682U |
| 52 | 4.4658 | 3.3645 | S-BAL35_O | 1.58913 | 61.14 | 1.682U |
| 53 | −6.7974 | 2.0860 | | 1. | | 1.682U |
| 54 | ∞ | 1.0094 | C2 | 1.76819 | 71.70 | 1.514U |
| 55 | ∞ | 3.5328 | | 1. | | 1.514U |
| 56 (Pupil) | ∞ | 8.1561 | | 1. | | 1.024 |
| Image plane | ∞ | 0. | | | | |

Aspherical surface data

3rd surface $K = -1.3693$
$AC2 = 0.0000E+00, AC4 = -1.1888E-01, AC6 = 3.3289E-02,$
$AC8 = 0.0000E+00, AC10 = 0.0000E+00$ 4th surface $K = -0.8584$
$AC2 = 0.0000E+00, AC4 = 2.8527E-01, AC6 = -8.4177E-01,$
$AC8 = 0.0000E+00, AC10 = 0.0000E+00$ 7th surface $K = -0.3311$
$AC2 = 0.0000E+00, AC4 = 6.0438E-03, AC6 = 0.0000E+00,$
$AC8 = 0.0000E+00, AC10 = 0.0000E+00$ 17th surface $K = 1.6990$
$AC2 = 0.0000E+00, AC4 = -1.7870E-03, AC6 = 0.0000E+00,$
$AC8 = 0.0000E+00, AC10 = 0.0000E+00$ 22nd surface $K = 1.6990$
$AC2 = 0.0000E+00, AC4 = 1.7870E-03, AC6 = 0.0000E+00,$
$AC8 = 0.0000E+00, AC10 = 0.0000E+00$ 28th surface $K = 1.6990$
$AC2 = 0.0000E+00, AC4 = -1.7870E-03, AC6 = 0.0000E+00,$
$AC8 = 0.0000E+00, AC10 = 0.0000E+00$ 33rd surface $K = 1.6990$
$AC2 = 0.0000E+00, AC4 = 1.7870E-03, AC6 = 0.0000E+00,$
$AC8 = 0.0000E+00, AC10 = 0.0000E+00$ -continued

| Unit mm |
|---|

39th surface

K = 1.6990
AC2 = 0.0000E+00, AC4 = −1.7870E−03, AC6 = 0.0000E+00,
AC8 = 0.0000E+00, AC10 = 0.0000E+00

45th surface

K = 1.6990
AC2 = 0.0000E+00, AC4 = 1.7870E−03, AC6 = 0.0000E+00,
AC8 = 0.0000E+00, AC10 = 0.0000E+00

Various data

| | |
|---|---|
| OB | 16.8227 |
| FOV | 88.8 |
| NAI | 0.1258 |
| IH | 1 |
| IHtotal | 1.022 |

Glass material data

| GLA | 587.56 | 656.27 | 486.13 | 435.83 | 546.07 |
|---|---|---|---|---|---|
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53__O__3 | 1.806250 | 1.800394 | 1.820103 | 1.831320 | 1.810931 |
| S-BAH11__O__3 | 1.666718 | 1.662589 | 1.676386 | 1.684125 | 1.670000 |
| S-BAL35__O__3 | 1.589130 | 1.586188 | 1.595824 | 1.601034 | 1.591429 |
| S-FPL51__O__3 | 1.496999 | 1.495136 | 1.501231 | 1.504507 | 1.498455 |
| S-FPL55__O__1 | 1.438750 | 1.437328 | 1.441963 | 1.444438 | 1.439857 |
| S-LAH53__O__1 | 1.806098 | 1.800251 | 1.819937 | 1.831152 | 1.810773 |
| S-LAH60__O__3 | 1.834000 | 1.827376 | 1.849819 | 1.862781 | 1.839323 |
| S-NBH56__O__1 | 1.854780 | 1.844876 | 1.879345 | 1.900448 | 1.862904 |
| S-TIL25__O__3 | 1.581439 | 1.577216 | 1.591486 | 1.599726 | 1.584822 |
| S-YGH51__O__3 | 1.754999 | 1.750624 | 1.765055 | 1.772956 | 1.758437 |

Ideal lens

| | |
|---|---|
| Displacement position | 56 (Pupil) |
| Focal length | 7.9590 |

Example 8

| Unit mm | | | | | |
|---|---|---|---|---|---|
| Surface data | | | | | |
| Surface no. | r | d | GLA | nd | vd | ER |
| Object plane | ∞ | 16.8224 | | 1. | | |
| 1 | ∞ | 0.2355 | C1 | 1.76900 | 64.15 | 1.178U |
| 2 | ∞ | 0.0673 | | 1. | | 1.178U |
| 3 | 0.8171 | 0.3548 | S-LAH58__O | 1.88300 | 40.76 | 0.858U |
| 4* | 0.2865 | 0.5569 | | 1. | | 0.538U |
| 5 | ∞ | 1.7664 | S-LAH53__O | 1.80610 | 40.95 | 1.228U |
| 6 | ∞ | 3.7975 | L-LAH53__O | 1.80625 | 40.91 | 1.228U |
| 7* | −2.0914 | 0.2108 | | 1. | | 1.228U |
| 8 | 3.2838 | 1.0463 | S-FPL55__O | 1.43875 | 94.66 | 1.228U |
| 9 | −3.1988 | 0.3926 | S-TIL25__O | 1.58144 | 40.75 | 1.228U |
| 10 | −24.6797 | 0.1824 | | 1. | | 1.228U |
| 11 | −14.2786 | 0.3693 | S-NBH56__O | 1.85478 | 24.80 | 1.228U |
| 12 | 2.2230 | 3.8235 | S-FPL55__O | 1.43875 | 94.66 | 1.228U |
| 13 | −2.9956 | 2.2270 | | 1. | | 1.228U |
| 14 | ∞ | 1.7428 | | 1. | | 1.346U |
| 15 | 6.0699 | 10.9750 | S-BAL35__O | 1.58913 | 61.14 | 1.262U |
| 16 | ∞ | 0.3196 | | 1. | | 1.262U |
| 17* | 6.4914 | 1.8841 | S-FPL55__O | 1.43875 | 94.66 | 1.262U |
| 18 | −3.5707 | 0.6729 | S-YGH51__O | 1.75500 | 52.32 | 1.262U |
| 19 | −6.2687 | 1.6822 | | 1. | | 1.262U |
| 20 | 6.2687 | 0.6729 | S-YGH51__O | 1.75500 | 52.32 | 1.262U |
| 21 | 3.5707 | 1.8841 | S-FPL55__O | 1.43875 | 94.66 | 1.262U |
| 22* | −6.4914 | 0.3196 | | 1. | | 1.262U |
| 23 | ∞ | 10.9750 | S-BAL35__O | 1.58913 | 61.14 | 1.262U |
| 24 | −6.0699 | 1.7428 | | 1. | | 1.262U |

-continued

| Unit mm | | | | | | |
|---|---|---|---|---|---|---|
| 25 | ∞ | 1.7428 | | 1. | | 1.346U |
| 26 | 6.0699 | 10.9750 | S-BAL35_O | 1.58913 | 61.14 | 1.262U |
| 27 | ∞ | 0.3196 | | 1. | | 1.262U |
| 28* | 6.4914 | 1.8841 | S-FPL55_O | 1.43875 | 94.66 | 1.262U |
| 29 | −3.5707 | 0.6729 | S-YGH51_O | 1.75500 | 52.32 | 1.262U |
| 30 | −6.2687 | 1.6822 | | 1. | | 1.262U |
| 31 | 6.2687 | 0.6729 | S-YGH51_O | 1.75500 | 52.32 | 1.262U |
| 32 | 3.5707 | 1.8841 | S-FPL55_O | 1.43875 | 94.66 | 1.262U |
| 33* | −6.4914 | 0.3196 | | 1. | | 1.262U |
| 34 | ∞ | 10.9750 | S-BAL35_O | 1.58913 | 61.14 | 1.262U |
| 35 | −6.0699 | 1.7428 | | 1. | | 1.262U |
| 36 | ∞ | 1.7428 | | 1. | | 1.346U |
| 37 | 6.0699 | 10.9750 | S-BAL35_O | 1.58913 | 61.14 | 1.262U |
| 38 | ∞ | 0.3196 | | 1. | | 1.262U |
| 39* | 6.4914 | 1.8841 | S-FPL55_O | 1.43875 | 94.66 | 1.262U |
| 40 | −3.5707 | 0.6729 | S-YGH51_O | 1.75500 | 52.32 | 1.262U |
| 41 | −6.2687 | 0.8411 | | 1. | | 1.262U |
| 42 (Stop) | ∞ | 0.8411 | | 1. | | 1.080U |
| 43 | 6.2687 | 0.6729 | S-YGH51_O | 1.75500 | 52.32 | 1.262U |
| 44 | 3.5707 | 1.8841 | S-FPL55_O | 1.43875 | 94.66 | 1.262U |
| 45* | −6.4914 | 0.3196 | | 1. | | 1.262U |
| 46 | ∞ | 10.9750 | S-BAL35_O | 1.58913 | 61.14 | 1.262U |
| 47 | −6.0699 | 1.7428 | | 1. | | 1.262U |
| 48 | ∞ | 5.4942 | | 1. | | 1.682U |
| 49 | 11.4016 | 1.5813 | S-FPL51_O | 1.49700 | 81.54 | 1.682U |
| 50 | −7.8702 | 0.2355 | | 1. | | 1.682U |
| 51 | ∞ | 0.5047 | S-LAH60_O | 1.83400 | 37.16 | 1.682U |
| 52 | 4.4657 | 3.3645 | S-BAL35_O | 1.58913 | 61.14 | 1.682U |
| 53 | −6.7973 | 2.0860 | | 1. | | 1.682U |
| 54 | ∞ | 1.0093 | C2 | 1.76819 | 71.70 | 1.514U |
| 55 | ∞ | 3.5327 | | 1. | | 1.514U |
| 56 (Pupil) | ∞ | 8.1559 | | 1. | | 1.024 |
| Image plane | ∞ | 0. | | | | |

| Aspherical surface data |
|---|

3rd surface

K = −0.7305
AC2 = 0.0000E+00, AC4 = −3.3444E−01, AC6 = 3.1901E−02,
AC8 = 0.0000E+00, AC10 = 0.0000E+00
4th surface K = −1.2851
AC2 = 0.0000E+00, AC4 = 1.8355E+00, AC6 = −2.0877E+00,
AC8 = 0.0000E+00, AC10 = 0.0000E+00
7th surface K = −0.6198
AC2 = 0.0000E+00, AC4 = 1.9588E−03, AC6 = 0.0000E+00,
AC8 = 0.0000E+00, AC10 = 0.0000E+00
17th surface K = 1.6990
AC2 = 0.0000E+00, AC4 = −1.7870E−03, AC6 = 0.0000E+00,
AC8 = 0.0000E+00, AC10 = 0.0000E+00
22nd surface K = 1.6990
AC2 = 0.0000E+00, AC4 = 1.7870E−03, AC6 = 0.0000E+00,
AC8 = 0.0000E+00, AC10 = 0.0000E+00
28th surface K = 1.6990
AC2 = 0.0000E+00, AC4 = −1.7870E−03, AC6 = 0.0000E+00,
AC8 = 0.0000E+00, AC10 = 0.0000E+00
33rd surface K = 1.6990
AC2 = 0.0000E+00, AC4 = 1.7870E−03, AC6 = 0.0000E+00,
AC8 = 0.0000E+00, AC10 = 0.0000E+00
39th surface K = 1.6990
AC2 = 0.0000E+00, AC4 = −1.7870E−03, AC6 = 0.0000E+00,
AC8 = 0.0000E+00, AC10 = 0.0000E+00

-continued

| Unit mm |
|---|

| 45th surface |
|---|
| K = 1.6990 |
| AC2 = 0.0000E+00, AC4 = 1.7870E−03, AC6 = 0.0000E+00, |
| AC8 = 0.0000E+00, AC10 = 0.0000E+00 |

| Various data | |
|---|---|
| OB | 16.8224 |
| FOV | 85.5 |
| NAI | 0.1259 |
| IH | 1 |
| IHtotal | 1.022 |

| Glass material data | | | | | |
|---|---|---|---|---|---|
| GLA | 587.56 | 656.27 | 486.13 | 435.83 | 546.07 |
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53__O_3 | 1.806250 | 1.800394 | 1.820103 | 1.831320 | 1.810931 |
| S-BAL35__O_3 | 1.589130 | 1.586188 | 1.595824 | 1.601034 | 1.591429 |
| S-FPL51__O_3 | 1.496999 | 1.495136 | 1.501231 | 1.504507 | 1.498455 |
| S-FPL55__O_1 | 1.438750 | 1.437328 | 1.441963 | 1.444438 | 1.439857 |
| S-LAH53__O_1 | 1.806098 | 1.800251 | 1.819937 | 1.831152 | 1.810770 |
| S-LAH58__O_3 | 1.882997 | 1.876560 | 1.898221 | 1.910497 | 1.888146 |
| S-LAH60__O_3 | 1.834000 | 1.827376 | 1.849819 | 1.862781 | 1.839323 |
| S-NBH56__O_1 | 1.854780 | 1.844876 | 1.879345 | 1.900448 | 1.862904 |
| S-TIL25__O_3 | 1.581439 | 1.577216 | 1.591486 | 1.599726 | 1.584822 |
| S-YGH51__O_3 | 1.754999 | 1.750624 | 1.765055 | 1.772956 | 1.758437 |

| Ideal lens | |
|---|---|
| Displacement position | 56 (Pupil) |
| Focal length | 7.9575 |

Example 9

| Unit mm |
|---|

| Surface data | | | | | | |
|---|---|---|---|---|---|---|
| Surface no. | r | d | GLA | nd | vd | ER |
| Object plane | ∞ | 16.8241 | | 1. | | |
| 1 | ∞ | 0.2355 | C1 | 1.76900 | 64.15 | 1.178U |
| 2 | ∞ | 0.0673 | | 1. | | 1.178U |
| 3* | 1.2164 | 0.3365 | L-LAH53__O | 1.80625 | 40.91 | 0.858U |
| 4* | 0.3119 | 0.5249 | | 1. | | 0.538U |
| 5 | ∞ | 1.7665 | S-LAH53__O | 1.80610 | 40.95 | 1.228U |
| 6 | ∞ | 3.6677 | L-LAH53__O | 1.80625 | 40.91 | 1.228U |
| 7* | −2.1868 | 0.2355 | | 1. | | 1.228U |
| 8 | 11.2702 | 1.1306 | S-FPL55__O | 1.43875 | 94.66 | 1.228U |
| 9 | −1.9186 | 0.4038 | S-TIL25__O | 1.58144 | 40.75 | 1.228U |
| 10 | −3.8443 | 0.3701 | | 1. | | 1.228U |
| 11 | ∞ | 1.3459 | S-TIH53__O | 1.84666 | 23.78 | 1.228U |
| 12 | 2.1434 | 4.2733 | S-FPL55__O | 1.43875 | 94.66 | 1.228U |
| 13 | −3.4738 | 1.7295 | | 1. | | 1.228U |
| 14 | ∞ | 1.8534 | | 1. | | 1.346U |
| 15 | 5.7548 | 11.1067 | S-BAL35__O | 1.58913 | 61.14 | 1.262U |
| 16 | ∞ | 0.3222 | | 1. | | 1.262U |
| 17* | 6.3660 | 1.0786 | S-FPL55__O | 1.43875 | 94.66 | 1.262U |
| 18 | −3.2871 | 1.4781 | S-YGH51__O | 1.75500 | 52.32 | 1.262U |
| 19 | −6.4189 | 1.1964 | | 1. | | 1.262U |
| 20 | 6.4189 | 1.4781 | S-YGH51__O | 1.75500 | 52.32 | 1.262U |
| 21 | 3.2871 | 1.0786 | S-FPL55__O | 1.43875 | 94.66 | 1.262U |
| 22* | −6.3660 | 0.3222 | | 1. | | 1.262U |
| 23 | ∞ | 11.1067 | S-BAL35__O | 1.58913 | 61.14 | 1.262U |
| 24 | −5.7548 | 1.8534 | | 1. | | 1.262U |
| 25 | ∞ | 1.8534 | | 1. | | 1.346U |
| 26 | 5.7548 | 11.1067 | S-BAL35__O | 1.58913 | 61.14 | 1.262U |
| 27 | ∞ | 0.3222 | | 1. | | 1.262U |
| 28* | 6.3660 | 1.0786 | S-FPL55__O | 1.43875 | 94.66 | 1.262U |
| 29 | −3.2871 | 1.4781 | S-YGH51__O | 1.75500 | 52.32 | 1.262U |

-continued

| | | | Unit mm | | | |
|---|---|---|---|---|---|---|
| 30 | −6.4189 | 1.1964 | | 1. | | 1.262U |
| 31 | 6.4189 | 1.4781 | S-YGH51_O | 1.75500 | 52.32 | 1.262U |
| 32 | 3.2871 | 1.0786 | S-FPL55_O | 1.43875 | 94.66 | 1.262U |
| 33* | −6.3660 | 0.3222 | | 1. | | 1.262U |
| 34 | ∞ | 11.1067 | S-BAL35_O | 1.58913 | 61.14 | 1.262U |
| 35 | −5.7548 | 1.8534 | | 1. | | 1.262U |
| 36 | ∞ | 1.8534 | | 1. | | 1.346U |
| 37 | 5.7548 | 11.1067 | S-BAL35_O | 1.58913 | 61.14 | 1.262U |
| 38 | ∞ | 0.3222 | | 1. | | 1.262U |
| 39* | 6.3660 | 1.0786 | S-FPL55_O | 1.43875 | 94.66 | 1.262U |
| 40 | −3.2871 | 1.4781 | S-YGH51_O | 1.75500 | 52.32 | 1.262U |
| 41 | −6.4189 | 0.5982 | | 1. | | 1.262U |
| 42 (Stop) | ∞ | 0.5982 | | 1. | | 1.120U |
| 43 | 6.4189 | 1.4781 | S-YGH51_O | 1.75500 | 52.32 | 1.262U |
| 44 | 3.2871 | 1.0786 | S-FPL55_O | 1.43875 | 94.66 | 1.262U |
| 45* | −6.3660 | 0.3222 | | 1. | | 1.262U |
| 46 | ∞ | 11.1067 | S-BAL35_O | 1.58913 | 61.14 | 1.262U |
| 47 | −5.7548 | 1.8534 | | 1. | | 1.262U |
| 48 | ∞ | 5.4948 | | 1. | | 1.682U |
| 49 | 11.4027 | 1.5815 | S-FPL51_O | 1.49700 | 81.54 | 1.682U |
| 50 | −7.8710 | 0.2355 | | 1. | | 1.682U |
| 51 | ∞ | 0.5047 | S-LAH60_O | 1.83400 | 37.16 | 1.682U |
| 52 | 4.4661 | 3.3648 | S-BAL35_O | 1.58913 | 61.14 | 1.682U |
| 53 | −6.7980 | 2.0862 | | 1. | | 1.682U |
| 54 | ∞ | 1.0094 | C2 | 1.76819 | 71.70 | 1.514U |
| 55 | ∞ | 3.5330 | | 1. | | 1.514U |
| 56 (Pupil) | ∞ | 8.1568 | | 1. | | 1.024 |
| Image plane | ∞ | 0. | | | | |

Aspherical surface data

3rd surface $K = -0.7490$
$AC2 = 0.0000E+00, AC4 = -2.5036E-01, AC6 = 7.7457E-02,$
$AC8 = 0.0000E+00, AC10 = 0.0000E+00$ 4th surface $K = -0.8100$
$AC2 = 0.0000E+00, AC4 = -1.4941E-01, AC6 = -1.7481E+00,$
$AC8 = 0.0000E+00, AC10 = 0.0000E+00$ 7th surface $K = -0.3490$
$AC2 = 0.0000E+00, AC4 = 5.4729E-03, AC6 = 0.0000E+00,$
$AC8 = 0.0000E+00, AC10 = 0.0000E+00$ 17th surface $K = 2.0539$
$AC2 = 0.0000E+00, AC4 = -1.7858E-03, AC6 = 0.0000E+00,$
$AC8 = 0.0000E+00, AC10 = 0.0000E+00$ 22nd surface $K = 2.0539$
$AC2 = 0.0000E+00, AC4 = 1.7858E-03, AC6 = 0.0000E+00,$
$AC8 = 0.0000E+00, AC10 = 0.0000E+00$ 28th surface $K = 2.0539$
$AC2 = 0.0000E+00, AC4 = -1.7858E-03, AC6 = 0.0000E+00,$
$AC8 = 0.0000E+00, AC10 = 0.0000E+00$ 33rd surface $K = 2.0539$
$AC2 = 0.0000E+00, AC4 = 1.7858E-03, AC6 = 0.0000E+00,$
$AC8 = 0.0000E+00, AC10 = 0.0000E+00$ 39th surface $K = 2.0539$
$AC2 = 0.0000E+00, AC4 = -1.7858E-03, AC6 = 0.0000E+00,$
$AC8 = 0.0000E+00, AC10 = 0.0000E+00$ 45th surface $K = 2.0539$
$AC2 = 0.0000E+00, AC4 = 1.7858E-03, AC6 = 0.0000E+00,$
$AC8 = 0.0000E+00, AC10 = 0.0000E+00$ -continued

| Unit mm | |
|---|---|
| Various data | |
| OB | 16.8241 |
| FOV | 88.7 |
| NAI | 0.1257 |
| IH | 1 |
| IHtotal | 1.022 |

| Glass material data | | | | | |
|---|---|---|---|---|---|
| GLA | 587.56 | 656.27 | 486.13 | 435.83 | 546.07 |
| C2 | 1.768189 | 1.765244 | 1.775956 | 1.783503 | 1.770656 |
| C1 | 1.768999 | 1.765391 | 1.777377 | 1.784102 | 1.771846 |
| L-LAH53__O__3 | 1.806250 | 1.800394 | 1.820103 | 1.831320 | 1.810931 |
| S-BAL35__O__3 | 1.589130 | 1.586188 | 1.595824 | 1.601034 | 1.591429 |
| S-FPL51__O__3 | 1.496999 | 1.495136 | 1.501231 | 1.504507 | 1.498455 |
| S-FPL55__O__1 | 1.438750 | 1.437328 | 1.441963 | 1.444438 | 1.439857 |
| S-LAH53__O__1 | 1.806098 | 1.800251 | 1.819937 | 1.831152 | 1.810773 |
| S-LAH60__O__3 | 1.834000 | 1.827376 | 1.849819 | 1.862781 | 1.839323 |
| S-TIH53__O__3 | 1.846660 | 1.836488 | 1.872096 | 1.894189 | 1.855041 |
| S-TIL25__O__3 | 1.581439 | 1.577216 | 1.591486 | 1.599726 | 1.584822 |
| S-YGH51__O__3 | 1.754999 | 1.750624 | 1.765055 | 1.772956 | 1.758437 |

| Ideal lens | |
|---|---|
| Displacement position | 56 (Pupil) |
| Focal length | 7.9621 |

Reference Example

| Unit mm | | | | | |
|---|---|---|---|---|---|
| Surface data | | | | | |
| Surface no. | r | d | GLA | nd | vd | ER |
|---|---|---|---|---|---|---|
| Object plane | ∞ | 16.7648 | | 1. | | |
| 1 | ∞ | 0.2347 | C1 | 1.76900 | 64.15 | 1.174U |
| 2 | ∞ | 0.1676 | | 1. | | 1.174U |
| 3 | −4.3196 | 0.3353 | S-LAH58__O | 1.88300 | 40.76 | 0.855U |
| 4 | 0.8493 | 0.2079 | | 1. | | 0.536U |
| 5 | ∞ | 1.8944 | S-LAH58__O | 1.88300 | 40.76 | 1.224U |
| 6 | ∞ | 2.0285 | S-LAH58__O | 1.88300 | 40.76 | 1.224U |
| 7 | −2.2770 | 0.2850 | | 1. | | 1.224U |
| 8 | 8.4749 | 2.5818 | S-FPL51__O | 1.49700 | 81.54 | 1.224U |
| 9 | −1.9551 | 0.5029 | S-TIH6__O | 1.80518 | 25.42 | 1.224U |
| 10 | −6.2472 | 1.4418 | | 1. | | 1.224U |
| 11 | 6.9423 | 0.5029 | S-NBH51__O | 1.74951 | 35.33 | 1.224U |
| 12 | 2.3437 | 4.9959 | S-LAL7__O | 1.65160 | 58.55 | 1.224U |
| 13 | −8.2211 | 1.0528 | | 1. | | 1.224U |
| 14 | ∞ | 1.8575 | | | | 1.341U |
| 15 | 6.7740 | 13.1503 | S-BAL35__O | 1.58913 | 61.14 | 1.257U |
| 16 | ∞ | 0.3185 | | 1. | | 1.257U |
| 17 | 8.9229 | 1.6094 | S-FPL51__O | 1.49700 | 81.54 | 1.257U |
| 18 | −3.4485 | 0.5029 | S-YGH51__O | 1.75500 | 52.32 | 1.257U |
| 19 | −7.0653 | 1.0897 | | 1. | | 1.257U |
| 20 (Stop) | ∞ | 1.0897 | | 1. | | 1.232U |
| 21 | 7.0653 | 0.5029 | S-YGH51__O | 1.75500 | 52.32 | 1.257U |
| 22 | 3.4485 | 1.6094 | S-FPL51__O | 1.49700 | 81.54 | 1.257U |
| 23 | −8.9229 | 0.3185 | | 1. | | 1.257U |
| 24 | ∞ | 13.1503 | S-BAL35__O | 1.58913 | 61.14 | 1.257U |
| 25 | −6.7740 | 1.8575 | | 1. | | 1.257U |
| 26 | ∞ | 5.4754 | | | | 1.676U |
| 27 | 11.3625 | 1.5759 | S-FPL51__O | 1.49700 | 81.54 | 1.676U |
| 28 | −7.8432 | 0.2347 | | 1. | | 1.676U |
| 29 | ∞ | 0.5029 | S-LAH60__O | 1.83400 | 37.16 | 1.676U |
| 30 | 4.4504 | 3.3530 | S-BAL35__O | 1.58913 | 61.14 | 1.676U |
| 31 | −6.7740 | 2.0788 | | 1. | | 1.676U |
| 32 | ∞ | 1.0059 | C2 | 1.76819 | 71.70 | 1.509U |
| 33 | ∞ | 3.5206 | | 1. | | 1.509U |
| 34 (Pupil) | ∞ | 8.1279S | | 1. | | 1.024 |
| Image plane | ∞ | 0. | | | | |

| Unit mm | |
|---|---|
| Various data | |
| OB | 16.7648 |
| FOV | 76.9 |
| NAI | 0.1259 |
| IH | 1 |
| IHtotal | 1.023 |

| Glass material data | | | | | |
|---|---|---|---|---|---|
| GLA | 587.56 | 656.27 | 486.13 | 435.83 | 546.07 |
| C2 | 1.768189 | 1.765244 | 1.775956 | 1.783503 | 1.770656 |
| C1 | 1.768999 | 1.765391 | 1.777377 | 1.784102 | 1.771846 |
| S-BAL35_O_3 | 1.589130 | 1.586188 | 1.595824 | 1.601034 | 1.591429 |
| S-FPL51_O_3 | 1.496999 | 1.495136 | 1.501231 | 1.504507 | 1.498455 |
| S-LAH58_O_3 | 1.882997 | 1.876560 | 1.898221 | 1.910497 | 1.888146 |
| S-LAH60_O_3 | 1.834000 | 1.827376 | 1.849819 | 1.862781 | 1.839323 |
| S-LAL7_O_3 | 1.651597 | 1.648207 | 1.659336 | 1.665374 | 1.654251 |
| S-NBH51_O_1 | 1.749505 | 1.743259 | 1.764473 | 1.776815 | 1.754531 |
| S-TIH6_O_3 | 1.805181 | 1.796106 | 1.827775 | 1.847286 | 1.812641 |
| S-YGH51_O_3 | 1.754999 | 1.750624 | 1.765055 | 1.772956 | 1.758437 |

| Ideal lens | |
|---|---|
| Displacement position | 34 (Pupil) |
| Focal length | 7.9299 |

Next, values of conditional expressions in each example are given below.

| | Example 1 | Example 2 | Example 3 |
|---|---|---|---|
| (1) (RL1i + RL1o)/(RL1i − RL1o) | −1.690 | −1.728 | −1.704 |
| (2) vdL1 | 40.910 | 40.910 | 40.920 |
| (3) {ΔASPL1i/(ndL1 − 1)}/IH | −0.028 | −0.031 | −0.031 |
| (4) {ΔASPL1o/(ndL1 − 1)}/IH | −0.108 | −0.125 | −0.121 |
| (5) {ΔASPL2i/(ndL2 − 1)}/IH | 0.013 | 0.013 | 0.015 |
| (6) ndL3n − ndL3p | 0.143 | 0.143 | 0.395 |
| (7) θgFL3n − θgFL3p | 0.043 | 0.043 | 0.044 |

| | Example 4 | Example 5 | Example 6 |
|---|---|---|---|
| (1) (RL1i + RL1o)/(RL1i − RL1o) | −1.626 | −1.558 | −1.764 |
| (2) vdL1 | 40.920 | 40.920 | 31.000 |
| (3) {ΔASPL1i/(ndL1 − 1)}/IH | −0.019 | −0.017 | −0.021 |
| (4) {ΔASPL1o/(ndL1 − 1)}/IH | −0.074 | −0.053 | −0.108 |
| (5) {ΔASPL2i/(ndL2 − 1)}/IH | 0.015 | 0.023 | 0.011 |
| (6) ndL3n − ndL3p | 0.337 | 0.395 | 0.250 |
| (7) θgFL3n − θgFL3p | 0.040 | 0.044 | 0.066 |

| | Example 7 | Example 8 | Example 9 |
|---|---|---|---|
| (1) (RL1i + RL1o)/(RL1i − RL1o) | −1.382 | −2.080 | −1.690 |
| (2) vdL1 | 48.320 | 40.760 | 40.910 |
| (3) {ΔASPL1i/(ndL1 − 1)}/IH | −0.028 | −0.045 | −0.028 |
| (4) {ΔASPL1o/(ndL1 − 1)}/IH | −0.048 | −0.281 | −0.108 |
| (5) {ΔASPL2i/(ndL2 − 1)}/IH | 0.013 | 0.015 | 0.013 |
| (6) ndL3n − ndL3p | 0.143 | 0.143 | 0.143 |
| (7) θgFL3n − θgFL3p | 0.043 | 0.043 | 0.043 |

In Numerical data of each example, a value of the image height is one. The value of the image height is a value which is normalized. Therefore, when Numerical data described in each example is multiplied by a coefficient, for example Numerical data is tripled, and a unit of length is millimeter, the image height is 3 mm (an image circle is 6 mm). In this case, the optical system for rigid endoscope of each example is suitable for an optical system of a laparoscope having an insertion part of which a diameter is 10 mm.

Figure 27:
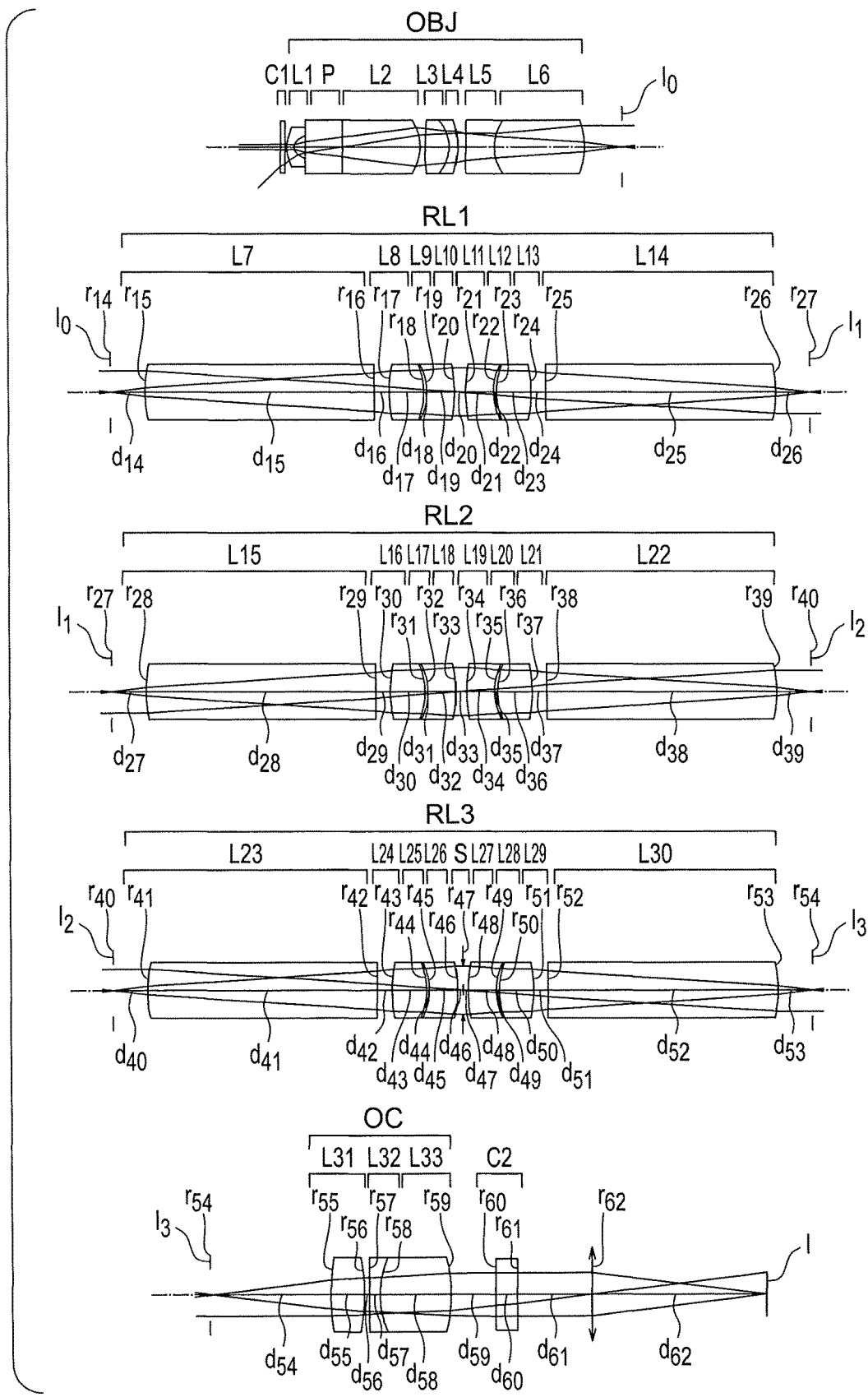
FIG. 27 is a lens cross-sectional view of an optical system for rigid endoscope of an example 1.
Figure 28:
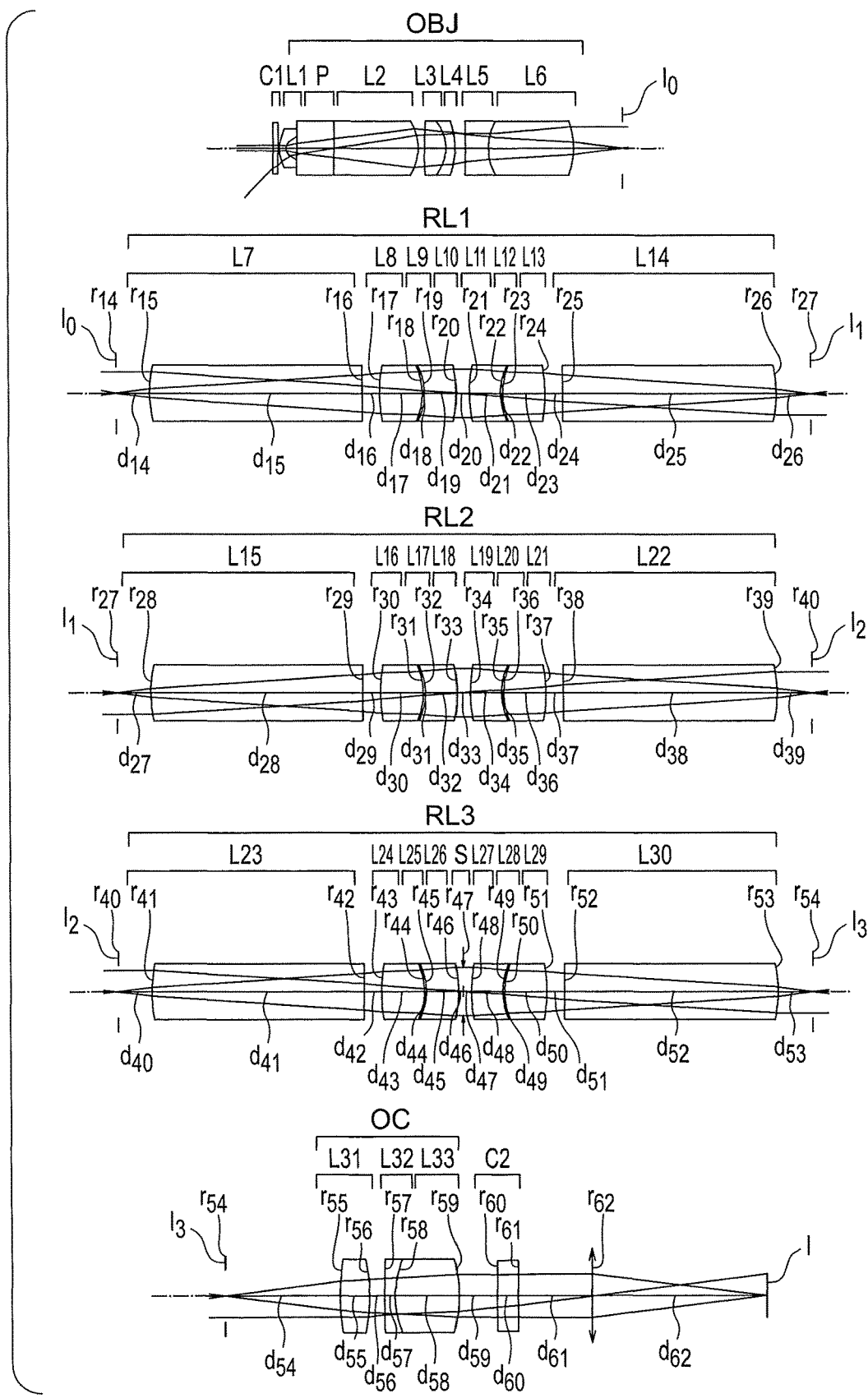
FIG. 28 is a lens cross-sectional view of an optical system for rigid endoscope of an example 2.
Figure 29:
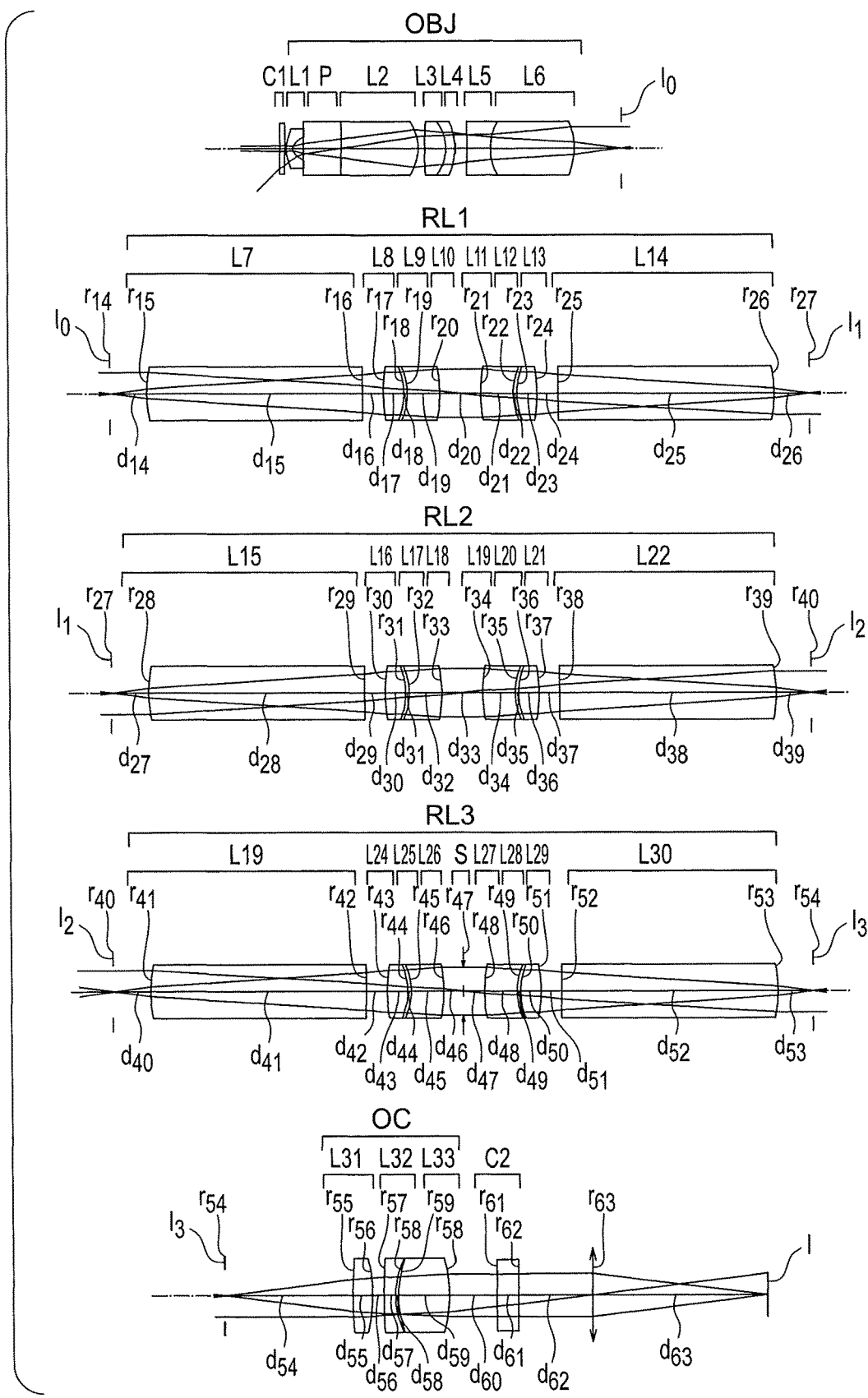
FIG. 29 is a lens cross-sectional view of an optical system for rigid endoscope of an example 3.
Figure 30:
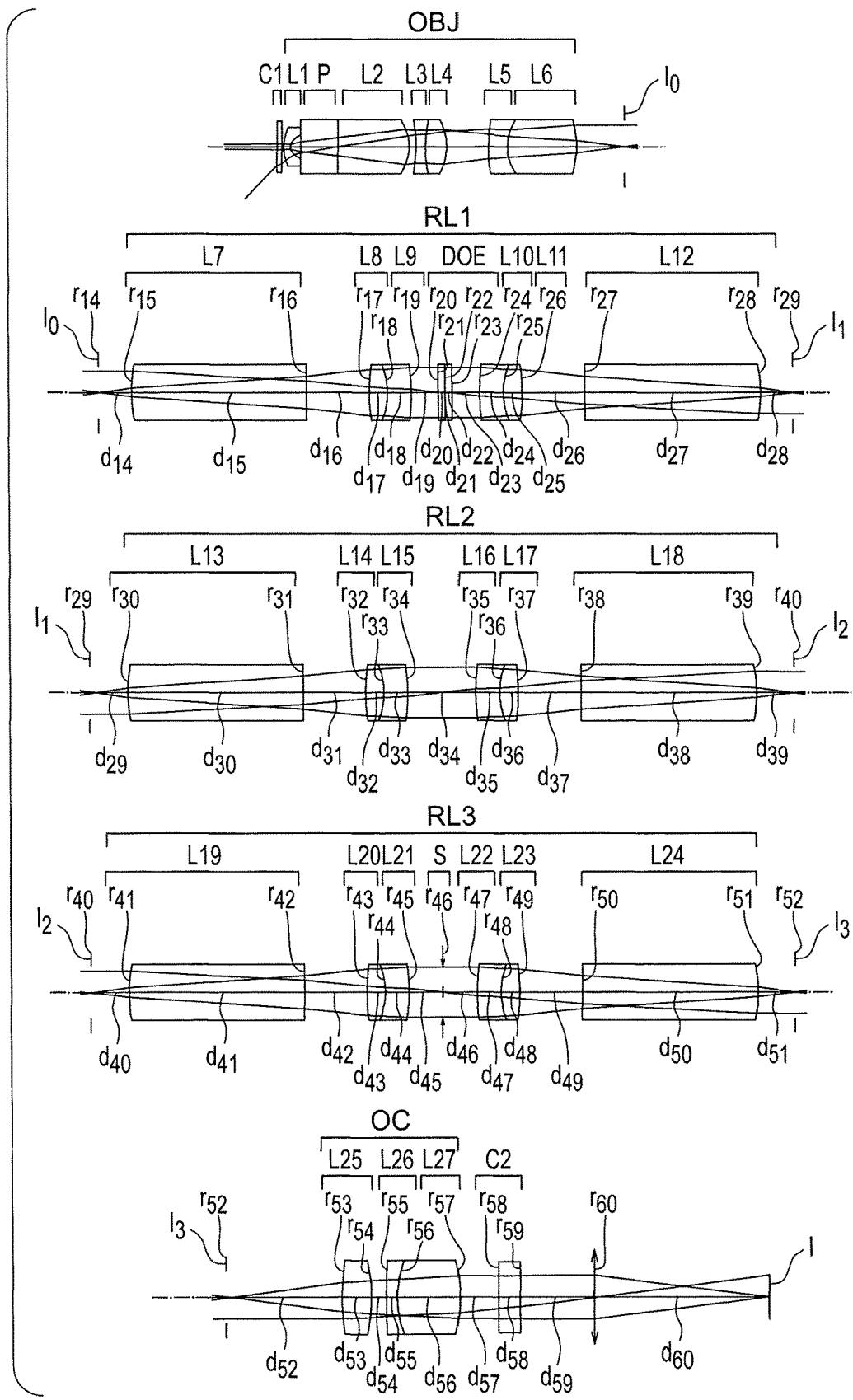
FIG. 30 is a lens cross-sectional view of an optical system for rigid endoscope of an example 4.
Figure 31:
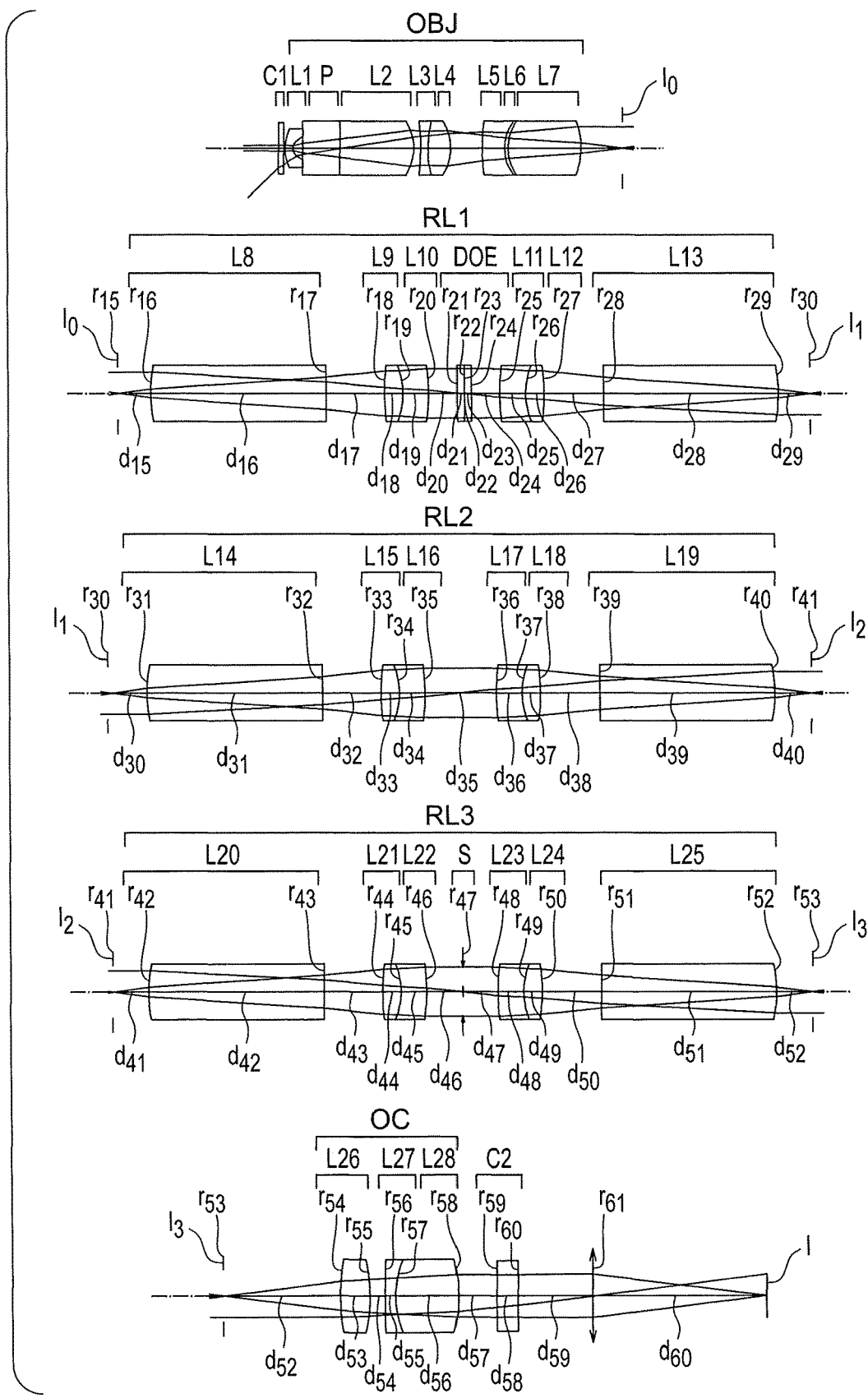
FIG. 31 is a lens cross-sectional view of an optical system for rigid endoscope of an example 5.
Figure 32:
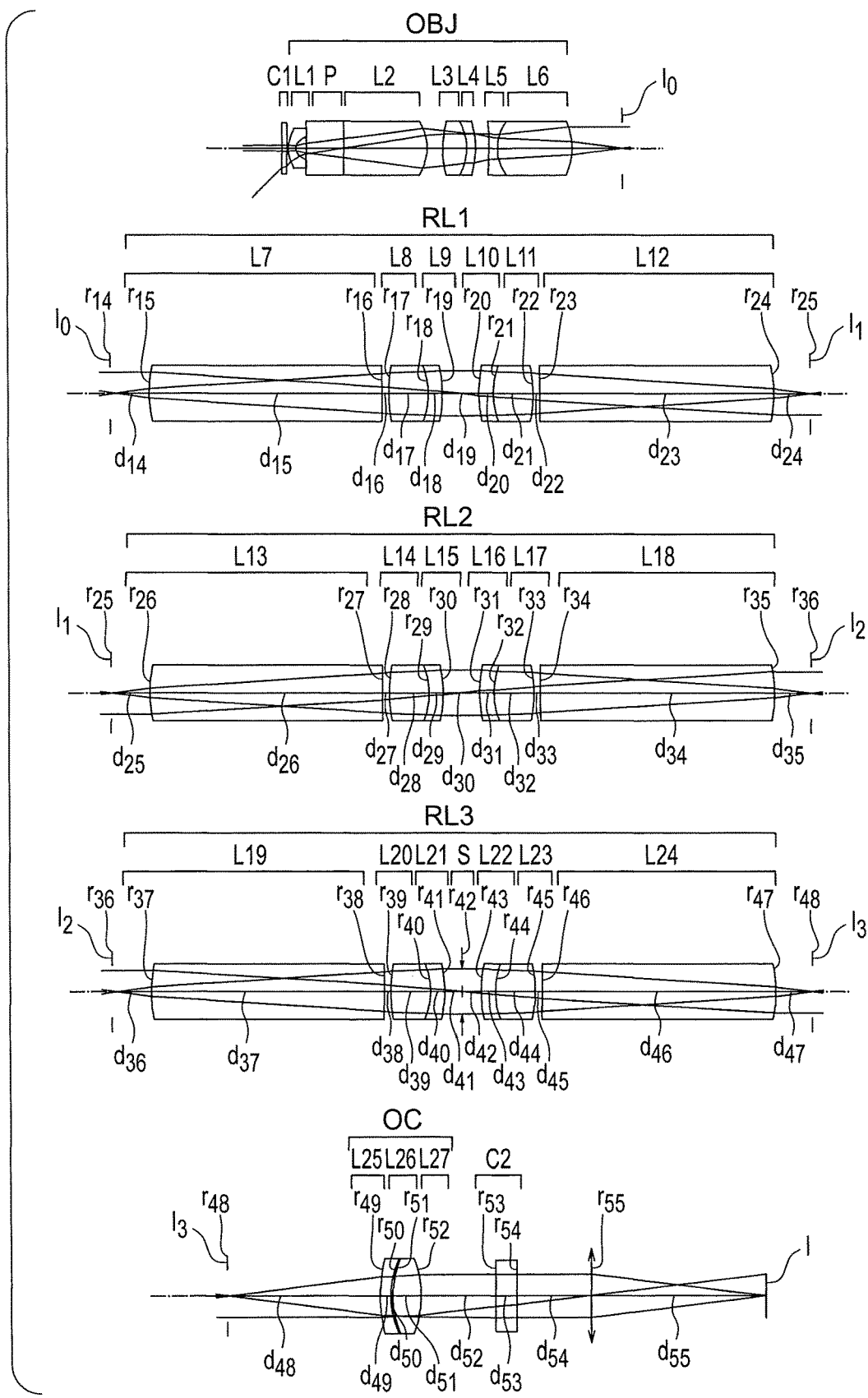
FIG. 32 is a lens cross-sectional view of an optical system for rigid endoscope of an example 6.
Figure 33:
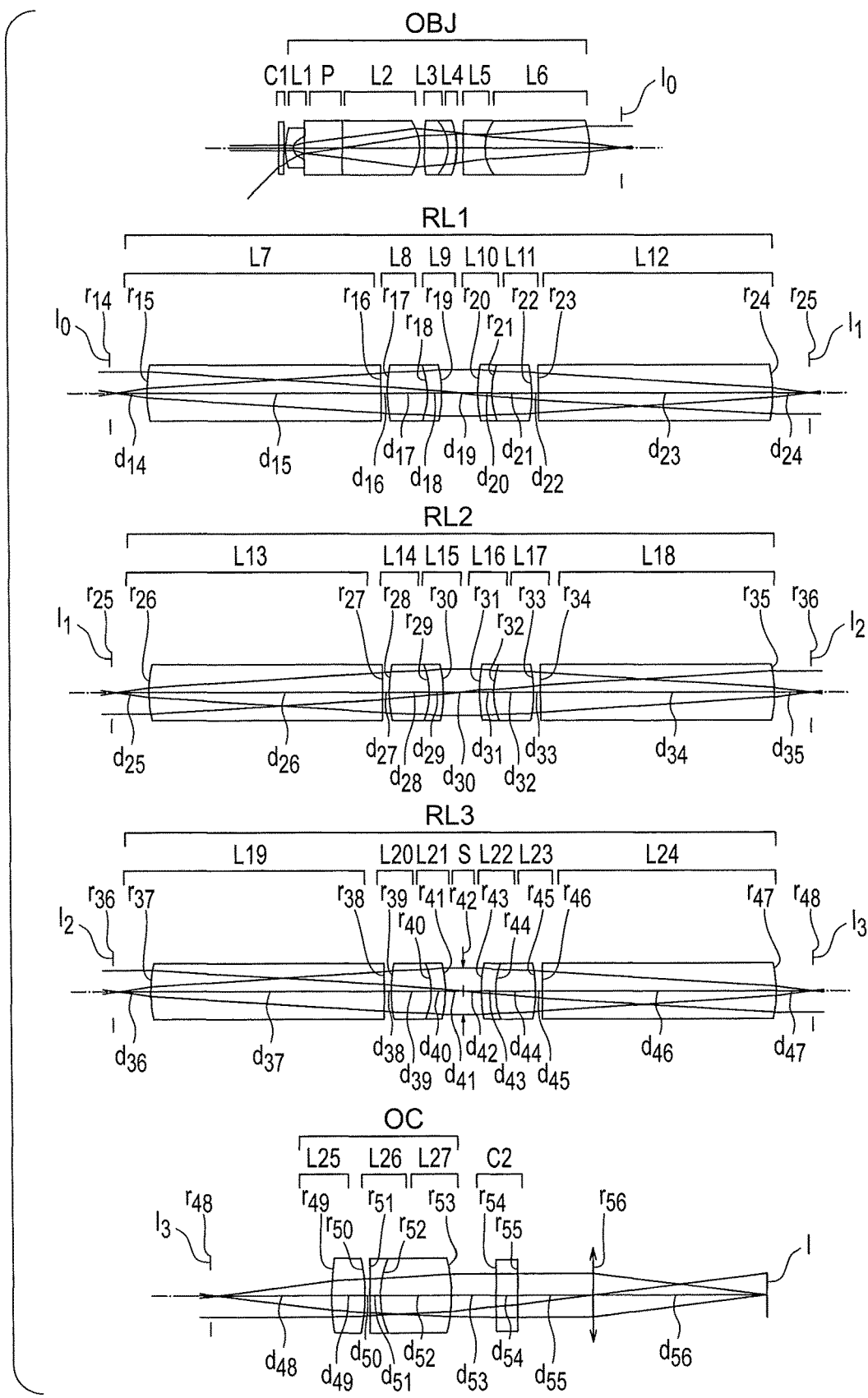
FIG. 33 is a lens cross-sectional view of an optical system for rigid endoscope of an example 7.
Figure 34:
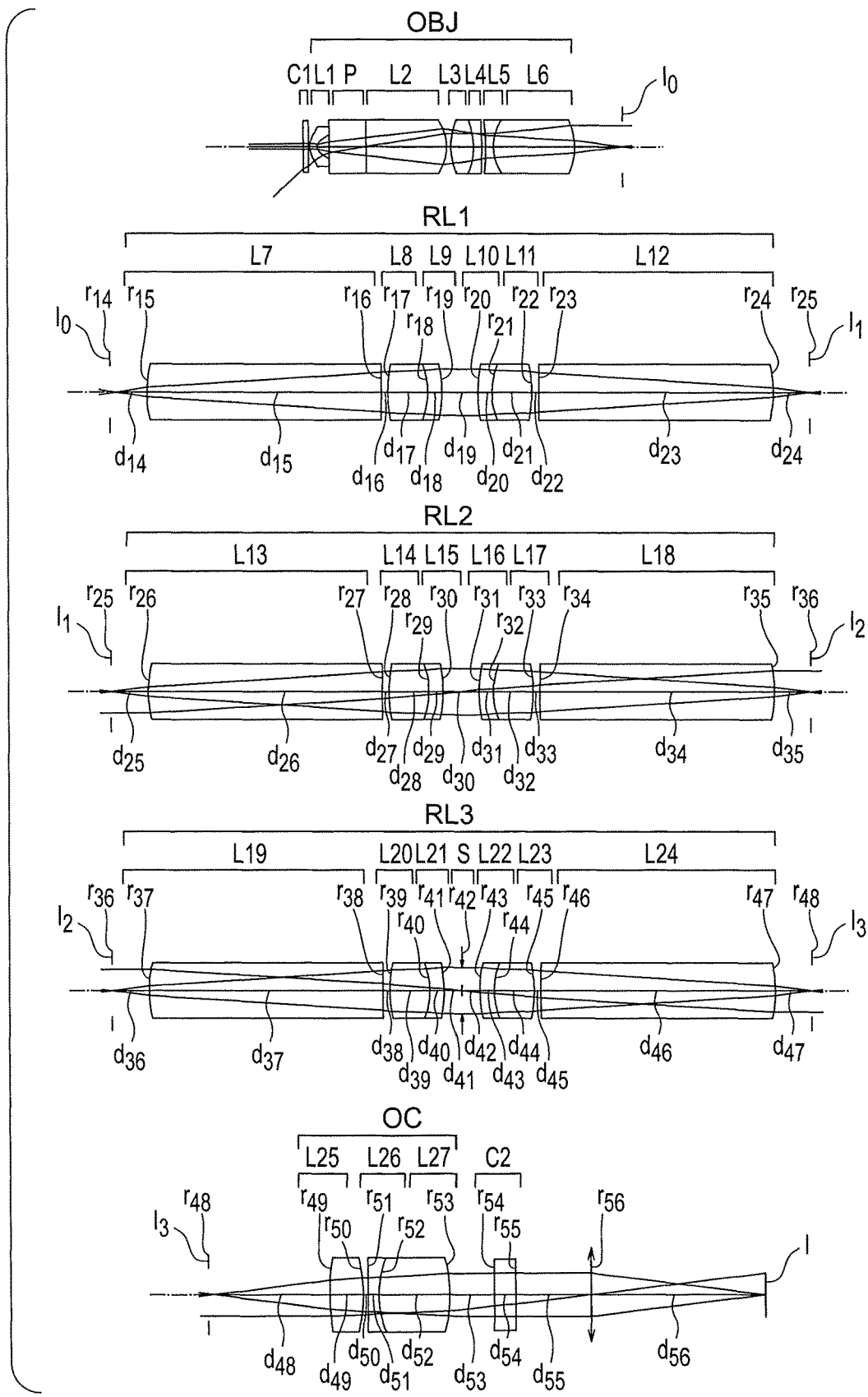
FIG. 34 is a lens cross-sectional view of an optical system for rigid endoscope of an example 8.
Figure 35:
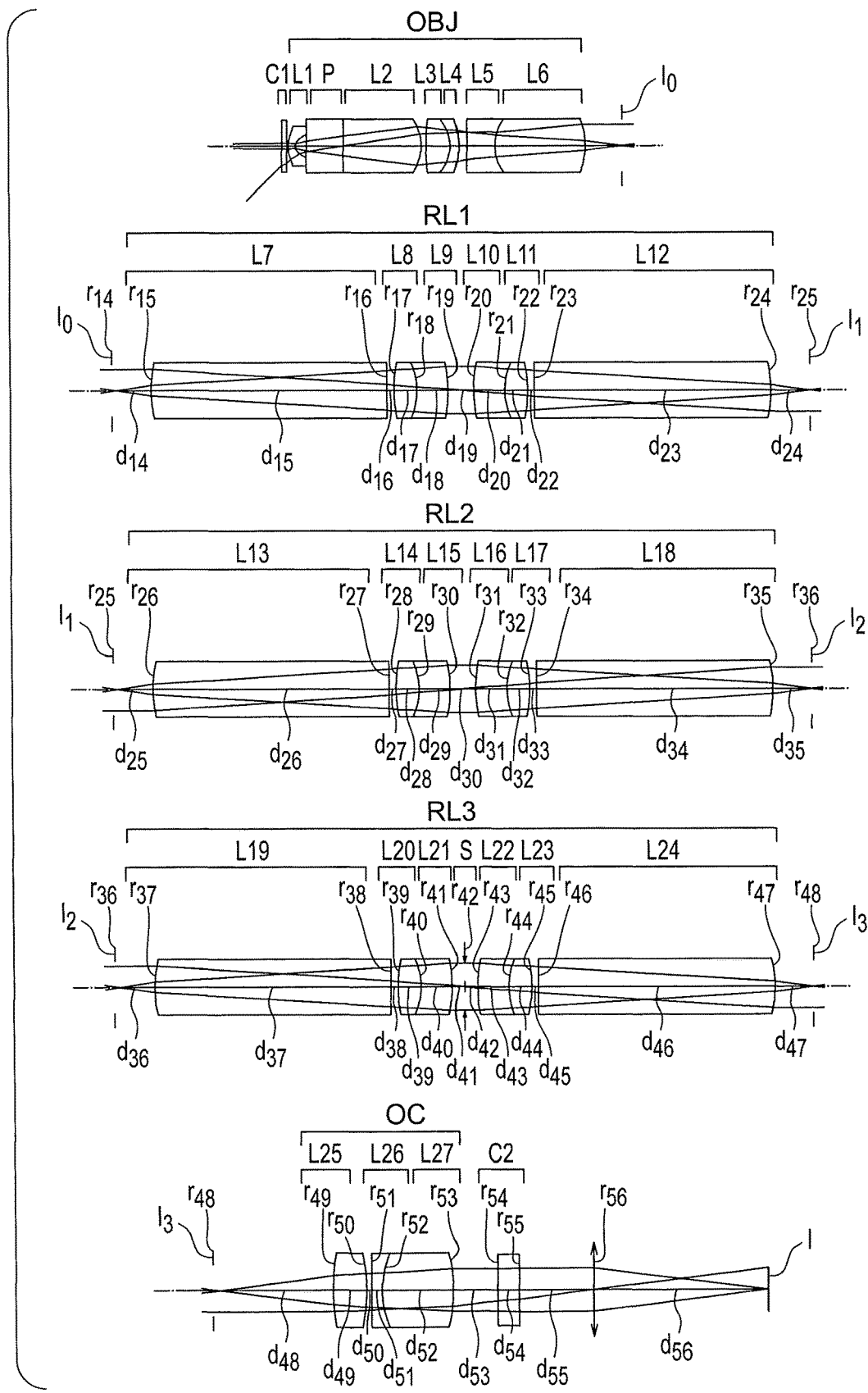
FIG. 35 is a lens cross-sectional view of an optical system for rigid endoscope of an example 9.

An example of a rigid endoscope will be described below. FIG. 27 is a schematic structural view of the rigid endoscope. A rigid endoscope 1 includes an objective optical system 2, an image relay unit 3, and an eyepiece optical system 4. Furthermore, the rigid endoscope 1 includes a light guide 5 and an illuminating-unit light source 6.

The image relay unit 3 includes a first relay optical system 3a, a second relay optical system 3b, and a third relay optical system 3c. The relay optical system of the example 1 is used for three relay optical systems.

Illuminating light is emerged from the illuminating-unit light source 6. The illuminating light, upon passing through the light guide 5, is emerged from a front end of the rigid endoscope. Accordingly, the illuminating light is irradiated to an observation object Sa.

A primary image Io of the observation object Sa is formed by the objective optical system 1. The primary image Io is relayed by the first relay optical system 3a. Accordingly, a first relay image I1 is formed. The first relay image I1 is relayed by the second relay optical system 3b. Accordingly, a second relay image I2 is formed. The second relay image I2 is relayed by the third relay optical system 3c. Accordingly, a third relay image I3 is formed. It is possible to observe the third relay image I3 by the eyepiece optical system OC.

According to the present embodiment, it is possible to provide an objective optical system in which both the distortion and the chromatic aberration are corrected favorably, while being small-sized and having a wide angle of view and a high resolution, and an optical system for rigid endoscope and a rigid endoscope using such objective optical system.

As described heretofore, the present invention is suitable for an objective optical system in which both the distortion and the chromatic aberration are corrected favorably, while being small-sized and having a wide angle of view and a high resolution, and an optical system for rigid endoscope and a rigid endoscope using such objective optical system.

What is claimed is:

1. An optical system for a rigid endoscope, comprising:
an objective optical system;
an eyepiece optical system; and
a relay optical system which is disposed between the objective optical system and the eyepiece optical system,
wherein the objective optical system includes in order from an object side:
a first lens having a negative refractive power;
a second lens having a positive refractive power;
a third lens having a positive refractive power; and
a fourth lens having a negative refractive power, and
wherein the following conditional expressions (1)-(4) are satisfied:

$$-3<(RL1i+RL1o)/(RL1i-RL1o)<-1.3 \quad (1),$$

$$30<vdL1 \quad (2),$$

$$\{\Delta ASPL1i/(ndL1-1)\}/IH<-0.005 \quad (3), \text{ and}$$

$$\{\Delta ASPL1o/(ndL1-1)\}/IH<-0.01 \quad (4),$$

where:
RL1o denotes a radius of curvature of an object-side surface of the first lens,
RL1i denotes a radius of curvature of an image-side surface of the first lens,
vdL1 denotes an Abbe number for the first lens,
ΔASPL1o denotes an amount of aspherical displacement at a first height on the object-side surface of the first lens,
ΔASPL1i denotes an amount of aspherical displacement at a second height on the image-side surface of the first lens,
the first height is a height that is 0.75 times a maximum image height,
the second height is a height that is 0.25 times the maximum image height,
ndL1 denotes a refractive index for a d-line of the first lens, and
IH denotes the maximum image height.

2. The optical system according to claim 1, wherein the following conditional expression (5) is satisfied:

$$0.005<\{\Delta ASPL2i/(ndL2-1)\}/IH \quad (5),$$

where:
ΔASPL2i denotes an amount of aspherical displacement at a third height on an image-side surface of the second lens,
the third height is a height that is 1 times the maximum image height,
ndL2 denotes a refractive index for a d-line of the second lens, and
IH denotes the maximum image height.

3. The optical system according to claim 2, wherein:
the third lens is a cemented lens having a positive lens and a negative lens, and
the following conditional expressions (6) and (7) are satisfied:

$$0<ndL3n-ndL3p<0.2 \quad (6), \text{ and}$$

$$\theta gFL3n-\theta gFL3p<0.06 \quad (7),$$

where:
ndL3p denotes a refractive index for a d-line of the positive lens,
ndL3n denotes a refractive index for a d-line of the negative lens,
θgFL3p denotes a partial dispersion ratio of the positive lens,
θgFL3n denotes a partial dispersion ratio of the negative lens, $$\theta gFL3p=(ngL3p-nFL3p)/(nFL3p-nCL3p),$$

$$\theta gFL3n=(ngL3n-nFL3n)/(nFL3n-nCL3n),$$

each of ngL3p, nFL3p, nCL3p denotes a refractive index of the positive lens for a g-line, an F-line, and a C-line respectively, and
each of ngL3n, nFL3n, and nCL3n denotes a refractive index of the negative lens for a g-line, an F-line, and a C-line respectively.

4. The optical system according to claim 1, wherein:
the third lens is a cemented lens having a positive lens and a negative lens, and
the following conditional expressions (6) and (7) are satisfied:

$$0<ndL3n-ndL3p<0.2 \quad (6), \text{ and}$$

$$\theta gFL3n-\theta gFL3p<0.06 \quad (7),$$

where:
ndL3p denotes a refractive index for a d-line of the positive lens,
ndL3n denotes a refractive index for a d-line of the negative lens,
θgFL3p denotes a partial dispersion ratio of the positive lens,
θgFL3n denotes a partial dispersion ratio of the negative lens, $$\theta gFL3_p=(ngL3p-nFL3p)/(nFL3p-nCL3p),$$

$$\theta gFL3n=(ngL3n-nFL3n)/(nFL3n-nCL3n),$$

each of ngL3p, nFL3p, nCL3p denotes a refractive index of the positive lens for a g-line, an F-line, and a C-line respectively, and
each of ngL3n, nFL3n, and nCL3n denotes a refractive index of the negative lens for a g-line, an F-line, and a C-line respectively.

5. A rigid endoscope, comprising:
the optical system according to claim 1; and
an illumination optical system.

6. An optical system for a rigid endoscope, comprising:
an objective optical system;
an eyepiece optical system; and
a relay optical system which is disposed between the objective optical system and the eyepiece optical system,
wherein the objective optical system includes in order from an object side:
a first lens having a negative refractive power;
a second lens having a positive refractive power;
a third lens having a positive refractive power; and
a fourth lens having a negative refractive power, and
wherein the following conditional expressions (1), (2), and (5) are satisfied:

$$-3<(RL1i+RL1o)/(RL1i-RL1o)<-1.3 \quad (1),$$

$$30<vdL1 \quad (2),$$

$$0.005<\{\Delta ASPL2i/(ndL2-1)\}/IH \quad (5),$$

where:
RL1o denotes a radius of curvature of an object-side surface of the first lens,
RL1i denotes a radius of curvature of an image-side surface of the first lens,
vdL1 denotes an Abbe number for the first lens,
ΔASPL2i denotes an amount of aspherical displacement at a third height on an image-side surface of the second lens,
the third height is a height that is 1 times a maximum image height,
ndL2 denotes a refractive index for a d-line of the second lens, and
IH denotes the maximum image height.

7. The optical system according to claim 6, wherein:
the third lens is a cemented lens having a positive lens and a negative lens, and
the following conditional expressions (6) and (7) are satisfied:

$$0 < ndL3n - ndL3p < 0.2 \quad (6), \text{ and}$$

$$\theta gFL3n - \theta gFL3p < 0.06 \quad (7),$$

where:
ndL3p denotes a refractive index for a d-line of the positive lens,
ndL3n denotes a refractive index for a d-line of the negative lens,
θgFL3p denotes a partial dispersion ratio of the positive lens,
θgFL3n denotes a partial dispersion ratio of the negative lens, $$\theta gFL3p = (ngL3p - nFL3p)/(nFL3p - nCL3p),$$

$$\theta gFL3n = (ngL3n - nFL3n)/(nFL3n - nCL3n),$$

each of ngL3p, nFL3p, nCL3p denotes a refractive index of the positive lens for a g-line, an F-line, and a C-line respectively, and
each of ngL3n, nFL3n, and nCL3n denotes a refractive index of the negative lens for a g-line, an F-line, and a C-line respectively.

8. An optical system for a rigid endoscope, comprising:
an objective optical system;
an eyepiece optical system; and
a relay optical system which is disposed between the objective optical system and the eyepiece optical system,
wherein:
the objective optical system includes in order from an object side:
a first lens having a negative refractive power;
a second lens having a positive refractive power;
a third lens having a positive refractive power; and
a fourth lens having a negative refractive power,
the third lens is a cemented lens having a positive lens and a negative lens, and
the following conditional expressions (1), (2), (6), and (7) are satisfied:

$$-3 < (RL1i + RL1o)/(RL1i - RL1o) < -1.3 \quad (1),$$

$$30 < vdL1 \quad (2),$$

$$0 < ndL3n - ndL3p < 0.2 \quad (6), \text{ and}$$

$$\theta gFL3n - \theta egFL3p < 0.06 \quad (7),$$

where:
RL1o denotes a radius of curvature of an object-side surface of the first lens,
RL1i denotes a radius of curvature of an image-side surface of the first lens,
vdL1 denotes an Abbe number for the first lens,
ndL3p denotes a refractive index for a d-line of the positive lens,
ndL3n denotes a refractive index for a d-line of the negative lens,
θgFL3p denotes a partial dispersion ratio of the positive lens,
θgFL3n denotes a partial dispersion ratio of the negative lens, $$\theta gFL3p = (ngL3p - nFL3p)/(nFL3p - nCL3p),$$

$$\theta gFL3n = (ngL3n - nFL3n)/(nFL3n - nCL3n),$$

each of ngL3p, nFL3p, nCL3p denotes a refractive index of the positive lens for a g-line, an F-line, and a C-line respectively, and
each of ngL3n, nFL3n, and nCL3n denotes a refractive index of the negative lens for a g-line, an F-line, and a C-line respectively.

* * * * *